(12) United States Patent
Judson et al.

(10) Patent No.: US 11,478,597 B2
(45) Date of Patent: Oct. 25, 2022

(54) NASAL ASSEMBLY

(71) Applicant: ResMed Pty Ltd, Bella Vista (AU)

(72) Inventors: Daniel Robert Judson, Blue Mountains (AU); Lee James Veliss, Rotterdam (NL); Aaron Samuel Davidson, Sydney (AU); Gregory Scott Smart, Sydney (AU); Alison Oldenburg, Sydney (AU); Susan Robyn Lynch, Maitland (AU); Philip Thomas Stallard, Sydney (AU); Daniel Joseph Kaars Sijpesteijn, Perth (AU); Gerard Michael Rummery, Woodford (AU); Eric Austin Mullins, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/537,557

(22) Filed: Nov. 30, 2021

(65) Prior Publication Data
US 2022/0080148 A1    Mar. 17, 2022

Related U.S. Application Data

(63) Continuation of application No. 15/293,694, filed on Oct. 14, 2016, now Pat. No. 11,202,877, which is a
(Continued)

(51) Int. Cl.
*A61M 16/06* (2006.01)
*A61M 16/08* (2006.01)

(52) U.S. Cl.
CPC .... *A61M 16/0683* (2013.01); *A61M 16/0605* (2014.02); *A61M 16/0633* (2014.02);
(Continued)

(58) Field of Classification Search
CPC .............. A61M 16/00; A61M 16/04; A61M 16/06–0694; A61M 16/08;
(Continued)

(56) References Cited

U.S. PATENT DOCUMENTS 2,603,215 A   7/1952  Peter
2,738,788 A   3/1956  Matheson et al.
(Continued)

FOREIGN PATENT DOCUMENTS

EP    1 163 923 A2    12/2001
GB    880824         10/1961
(Continued)

OTHER PUBLICATIONS

Apr. 24, 2015 Application under Regulation 168 for Extension of Time issued in New Zealand Application No. 611284.
(Continued)

*Primary Examiner* — Margaret M Luarca
(74) *Attorney, Agent, or Firm* — Nixon & Vanderhye P.C.

(57) ABSTRACT

A nasal assembly for delivering breathable gas to a patient includes a frame having lateral connector, a cushion with a pair of nozzles, and a clip to secure the cushion to the frame. The frame includes a vent channel and a plurality of vent holes. The frame/cushion includes structure (lugs/cut outs) to prevent the assembly of an unvented frame with an unvented cushion, for safety purposes. The frame includes cored portions that interface with corner lugs provided on the cushion. A patient interface includes a frame, a cushion (nasal mask, nasal-oro mask, nozzles, etc.) and a vent assembly including a pattern of vent holes including at least two rows.

29 Claims, 40 Drawing Sheets

Related U.S. Application Data continuation of application No. 12/084,373, filed as application No. PCT/AU2006/001507 on Oct. 13, 2006, now abandoned, which is a continuation-in-part of application No. 29/258,084, filed on Apr. 14, 2006, now Pat. No. Des. 587,800.

(60) Provisional application No. 60/838,442, filed on Aug. 18, 2006, provisional application No. 60/819,626, filed on Jul. 11, 2006, provisional application No. 60/795,615, filed on Apr. 28, 2006, provisional application No. 60/758,200, filed on Jan. 12, 2006, provisional application No. 60/734,282, filed on Nov. 8, 2005.

(52) U.S. Cl.
CPC .... *A61M 16/0666* (2013.01); *A61M 16/0816* (2013.01); *A61M 16/0825* (2014.02)

(58) Field of Classification Search
CPC .......... A61M 16/0816; A61M 16/0683; A61M 16/0605; A61M 16/0633
See application file for complete search history.

(56) References Cited

U.S. PATENT DOCUMENTS

| | | | |
|---|---|---|---|
| 2,742,821 | A | 4/1956 | Sweetman |
| 2,763,263 | A | 9/1956 | Ellman |
| 3,118,445 | A | 1/1964 | Marius |
| 3,228,610 | A | 1/1966 | Quaas et al. |
| 3,425,600 | A | 2/1969 | Abplanalp |
| 3,513,844 | A | 5/1970 | Smith |
| 3,633,575 | A | 1/1972 | Brumfield |
| 3,850,171 | A | 11/1974 | Ball et al. |
| 4,090,510 | A | 5/1978 | Segersten |
| 4,161,516 | A | 7/1979 | Bell |
| 4,328,797 | A | 5/1982 | Rollins et al. |
| 4,347,633 | A | 9/1982 | Gammos et al. |
| 4,424,106 | A | 1/1984 | Rossoshinsky et al. |
| 4,782,832 | A | 11/1988 | Trimble |
| 4,856,508 | A | 8/1989 | Tayebi |
| 4,989,596 | A | 2/1991 | Macris et al. |
| 5,042,478 | A | 8/1991 | Kopala et al. |
| 5,195,773 | A | 3/1993 | Sawada et al. |
| 5,324,295 | A | 6/1994 | Shapiro |
| 5,431,158 | A | 7/1995 | Tirotta |
| 5,533,506 | A | 7/1996 | Wood |
| 5,655,523 | A | 8/1997 | Hodson et al. |
| 5,683,293 | A | 11/1997 | Mohammed et al. |
| 5,687,746 | A | 11/1997 | Rose et al. |
| 5,709,204 | A | 1/1998 | Lester |
| 5,724,965 | A | 3/1998 | Handke et al. |
| 5,740,649 | A | 4/1998 | Fuchs et al. |
| 5,962,349 | A | 10/1999 | Mizukami et al. |
| 6,012,455 | A | 1/2000 | Goldstein |
| 6,017,315 | A | 1/2000 | Starr et al. |
| 6,044,844 | A | 4/2000 | Kwok et al. |
| 6,074,446 | A | 6/2000 | Fujino |
| 6,077,152 | A | 6/2000 | Warehime |
| 6,082,356 | A | 7/2000 | Stradella |
| 6,119,694 | A | 9/2000 | Correa |
| 6,210,806 | B1 | 4/2001 | Hidaka et al. |
| 6,241,247 | B1 | 6/2001 | Sternberg et al. |
| 6,336,455 | B1 | 1/2002 | Howlett |
| 6,378,518 | B1 | 4/2002 | Miekka et al. |
| 6,401,716 | B1 | 6/2002 | Sword et al. |
| 6,418,929 | B1 | 7/2002 | Norfleet |
| 6,431,172 | B1 | 8/2002 | Bordewick |
| 6,561,190 | B1 | 5/2003 | Kwok |
| 6,561,191 | B1 * | 5/2003 | Kwok .................... A62B 18/10 128/205.24 |
| 6,581,594 | B1 | 6/2003 | Drew et al. |
| 6,595,215 | B2 | 7/2003 | Wood |
| 6,638,588 | B1 | 10/2003 | Bowen et al. |
| 6,691,707 | B1 | 2/2004 | Gunaratnam et al. |
| 6,851,425 | B2 | 2/2005 | Jaffre et al. |
| 7,000,614 | B2 | 2/2006 | Lang et al. |
| 7,207,335 | B2 | 4/2007 | Kwok et al. |
| D557,800 | S | 12/2007 | Hitchcock et al. |
| 7,318,437 | B2 | 1/2008 | Gunaratnam et al. |
| D587,800 | S | 3/2009 | Judson et al. |
| 7,686,800 | B2 | 3/2010 | Savage et al. |
| 7,827,990 | B1 | 11/2010 | Melidis et al. |
| 7,836,884 | B2 | 11/2010 | Wright |
| 7,845,354 | B2 | 12/2010 | Kwok et al. |
| 7,934,501 | B2 | 5/2011 | Fu et al. |
| 7,942,150 | B2 | 5/2011 | Guney et al. |
| 8,042,539 | B2 | 10/2011 | Chandran et al. |
| 8,122,886 | B2 | 2/2012 | Kwok et al. |
| 8,261,746 | B2 | 9/2012 | Lynch et al. |
| 8,297,283 | B2 | 10/2012 | Hitchcock et al. |
| 8,397,728 | B2 | 3/2013 | D'Souza et al. |
| 2001/0029948 | A1 | 10/2001 | Ingle et al. |
| 2002/0108613 | A1 * | 8/2002 | Gunaratnam ..... A61M 16/0616 128/205.25 |
| 2002/0172566 | A1 | 11/2002 | Issler |
| 2003/0005931 | A1 * | 1/2003 | D. Jaffre ............. A61M 16/208 128/200.14 |
| 2003/0005935 | A1 | 1/2003 | Kwok |
| 2003/0034034 | A1 * | 2/2003 | Kwok ............... A61M 16/0816 128/207.13 |
| 2003/0075180 | A1 | 4/2003 | Raje et al. |
| 2003/0079751 | A1 | 5/2003 | Kwok |
| 2003/0196655 | A1 | 10/2003 | Ging |
| 2004/0022820 | A1 | 2/2004 | Anderson |
| 2004/0112385 | A1 | 6/2004 | Drew et al. |
| 2004/0177850 | A1 | 9/2004 | Gradon et al. |
| 2004/0226566 | A1 | 11/2004 | Gunaratnam et al. |
| 2005/0011524 | A1 | 1/2005 | Thomlinson |
| 2005/0028822 | A1 | 2/2005 | Sleeper |
| 2005/0076913 | A1 | 4/2005 | Ho et al. |
| 2005/0092326 | A1 | 5/2005 | Drew et al. |
| 2005/0126573 | A1 | 6/2005 | Jaffre et al. |
| 2005/0241644 | A1 | 11/2005 | Gunaratnam et al. |
| 2006/0042629 | A1 | 3/2006 | Geist |
| 2006/0118119 | A1 | 6/2006 | Berthon-Jones et al. |
| 2006/0174887 | A1 | 8/2006 | Chandran et al. |
| 2006/0196509 | A1 | 9/2006 | Drew et al. |
| 2006/0201514 | A1 | 9/2006 | Jones et al. |
| 2006/0237018 | A1 * | 10/2006 | McAuley ............. A61M 16/06 128/206.24 |
| 2006/0254593 | A1 | 11/2006 | Chang |
| 2006/0266361 | A1 | 11/2006 | Hernandez |
| 2007/0044804 | A1 | 3/2007 | Matula et al. |
| 2007/0062536 | A1 | 3/2007 | McAuley et al. |
| 2007/0095350 | A1 | 5/2007 | Darkin et al. |
| 2007/0175480 | A1 | 8/2007 | Gradon et al. |
| 2007/0221226 | A1 | 9/2007 | Hansen et al. |
| 2009/0044810 | A1 | 2/2009 | Kwok |
| 2009/0139526 | A1 | 6/2009 | Melidis et al. |
| 2009/0151729 | A1 | 6/2009 | Judson et al. |
| 2009/0277452 | A1 | 11/2009 | Lubke et al. |
| 2010/0051034 | A1 | 3/2010 | Lynch et al. |
| 2010/0282265 | A1 | 11/2010 | Melidis et al. |
| 2011/0180071 | A1 | 7/2011 | Veliss et al. |
| 2011/0277771 | A1 | 11/2011 | Kwok et al. |
| 2017/0028153 | A1 | 2/2017 | Judson et al. |

FOREIGN PATENT DOCUMENTS

| | | |
|---|---|---|
| WO | WO 1998/034665 | 8/1998 |
| WO | WO 00/13751 | 3/2000 |
| WO | WO 2001/062326 | 8/2001 |
| WO | WO 2002/066105 | 8/2002 |
| WO | WO 2004/030736 | 4/2004 |
| WO | WO 2004/073778 | 9/2004 |
| WO | WO 2005/021075 | 3/2005 |
| WO | WO 2005/079726 | 9/2005 |
| WO | WO 2006/069415 | 7/2006 |
| WO | WO 2006/074516 | 7/2006 |
| WO | WO 2006/074517 | 7/2006 |

(56) References Cited

FOREIGN PATENT DOCUMENTS

| WO | WO 2007/041751 | 4/2007 |
|----|----------------|--------|
| WO | WO 2007/045008 | 4/2007 |
| WO | WO 2007/048174 A1 | 5/2007 |
| WO | WO 2007/053878 | 5/2007 |

OTHER PUBLICATIONS

Apr. 24, 2015 Notice of Opposition to Grant of Patent (Section 21) issued in New Zealand Application No. 611284.
Apr. 29, 2015 Extension of Time Granted issued in New Zealand Application No. 611284.
Aug. 28, 2015 Opponent's Letter to the Applicant issued in corresponding New Zealand Application No. 611284.
Feb. 2, 2015 Office Action issued in U.S. Appl. No. 12/084,373.
Gunaratnam et al., U.S. Appl. No. 10/781,929, filed Feb. 2004.
Gunaratnam et al., U.S. Appl. No. 11/101,657, filed Apr. 2005.
Gunaratnam, U.S. Appl. No. 29/213,882, filed May 2004.
Jan. 9, 2007 International Search Report issued in International Application No. PCT/AU2006/001507.
Jan. 10, 2008 International Search Report issued in International Application No. PCT/AU2007/001749.
Jan. 11, 2011 Examination Report issued in New Zealand Application No. 590211.
Jan. 11, 2011 Examination Report issued in New Zealand Application No. 567374.
Judson et al., U.S. Appl. No. 29/258,083, filed Apr. 2006.
Judson et al., U.S. Appl. No. 29/258,084, filed Apr. 2006.
Judson et al., U.S. Appl. No. 29/258,085, filed Apr. 2006.
Judson et al., U.S. Appl. No. 60/734,282, filed Nov. 2005.
Judson et al., U.S. Appl. No. 60/758,200, filed Jan. 2006.
Judson et al., U.S. Appl. No. 60/819,626, filed Jul. 2006.
Judson et al., U.S. Application No. 60/83 8,442, filed Aug. 2006.
Jun. 20, 2014 Office Action issued in U.S. Appl. No. 12/084,373.
Jun. 24, 2015 Amended Notice of Opposition to Grant of Patent issued in corresponding New Zealand Patent Application No. 611284.
Jun. 24, 2015 Deadline for Counterstatement issued in corresponding New Zealand Patent Application No. 611284.
Jun. 24, 2015 Statement of Case issued in corresponding New Zealand Patent Application No. 611284.
Mar. 25, 2013 Amended Notice of Opposition to Grant of Patent issued in New Zealand Application No. 590211.
Mar. 25, 2013 Deadline for Counterstatement issued in New Zealand Application No. 590211.
Mar. 25, 2013 Statement of Case issued in New Zealand Application No. 590211.
Mar. 28, 2016 Office Action issued in U.S. Appl. No. 12/084,373.
Oct. 18, 2016 Amended Notice of Opposition to Grant of Patent issued in New Zealand Application No. 709729.
Oct. 29, 2012 Notice of Opposition issued in New Zealand Application No. 590211.
Oct. 29, 2012 Proceeding Correspondence issued in New Zealand Application No. 590211.
Scheiner et al., U.S. Appl. No. 60/795,562, filed Apr. 2006.
Sep. 24, 2015 Office Action issued in U.S. Appl. No. 12/084,373.
Sep. 25, 2015 Notice of Allowance issued in U.S. Appl. No. 12/312,308.
Sep. 3, 2015 Decision of Assistant Commissioner issued in corresponding New Zealand Application No. 590211.
Smart et al., U.S. Appl. No. 60/795,615, filed Apr. 2006.
May 27, 2016 Statement of Case filed in New Zealand Patent Application No. 709729 (12 pgs.).
Nov. 18, 2016 Amended Statement of Case filed in New Zealand Patent Application No. 709729 (28 pgs.).
Jan. 12, 2017 Letter to IPONZ and Marked-up Amended Statement of Case filed in New Zealand Patent Application No. 709729.
Dec. 21, 2017 Letter to IPONZ filed in New Zealand Patent Application No. 611284.
Jan. 7, 2019 Further Examination Report issued in New Zealand Patent Application No. 731139.
Nov. 30, 2018 Letter to IPONZ filed in New Zealand Patent Application No. 709729.
Nov. 30, 2018 Third Amended Notice of Opposition (marked up and clean formats) filed in New Zealand Patent Application No. 709729.
Nov. 30, 2018 Fourth Amended Statement of Case (marked up and clean formats) filed in New Zealand Patent Application No. 709729.
Request for Amendment After Acceptance dated May 29, 2020 in New Zealand Application No. 709729, 6 pages.
First Examination Report dated Sep. 15, 2020 in New Zealand Application No. 767816, 3 pages.
Request for Amendment After Acceptance dated Sep. 30, 2020 in New Zealand Application No. 709729, 6 pages.
Further Exam Report dated Jul. 20, 2021 in New Zealand Application No. 775125, 1 page.
Further Exam Report dated Aug. 12, 2021 in New Zealand Application No. 767816, 2 pages.
Judson et al., U.S. Appl. No. 15/293,694, filed Oct. 14, 2016, for "Nasal Assembly," (parent application).

\* cited by examiner

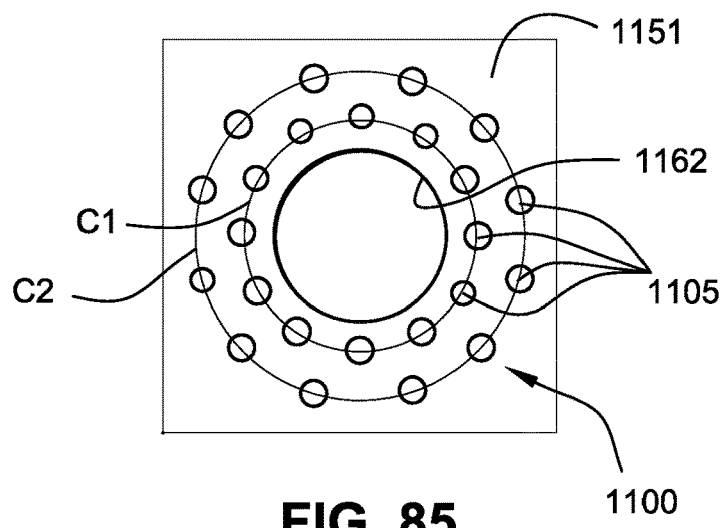
FIG. 85
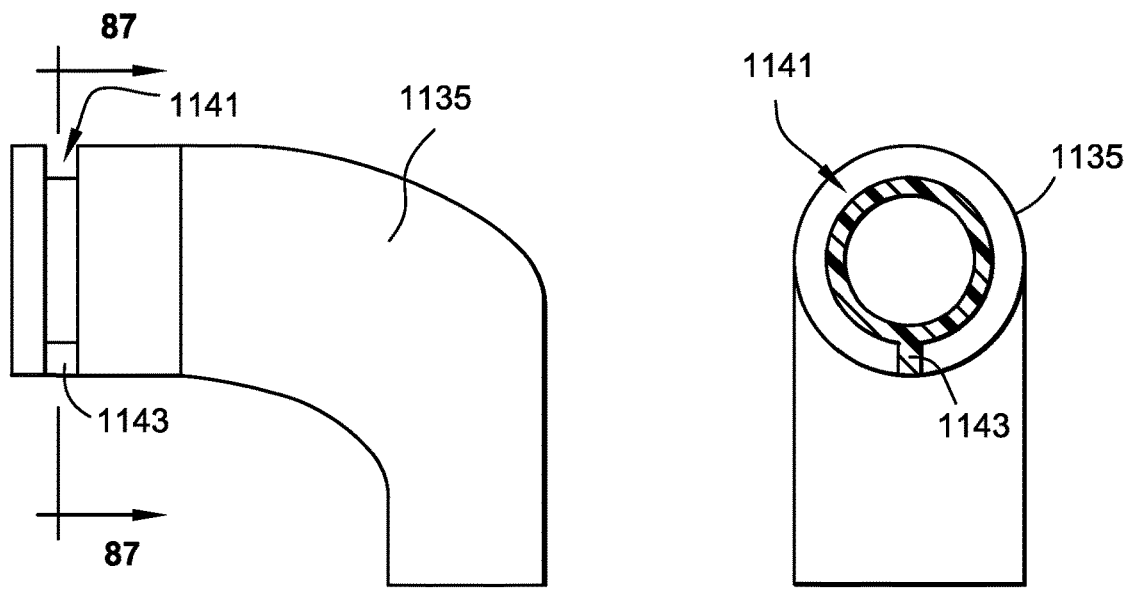
FIG. 86  FIG. 87
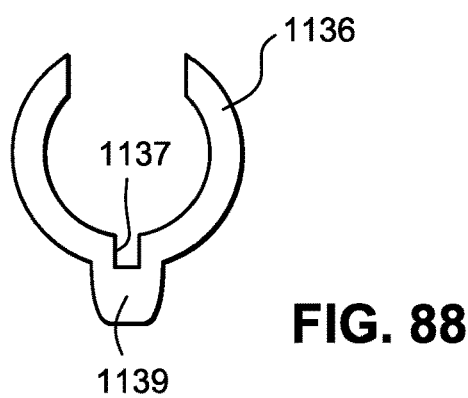
FIG. 88

NASAL ASSEMBLY

CROSS REFERENCE TO APPLICATIONS

This application is a continuation of Ser. No. 15/293,694, filed Oct. 14, 2016, which is a continuation of U.S. application Ser. No. 12/084,373, filed Apr. 30, 2008, which is the U.S. National Phase of International Application No. PCT/AU2006/001507, filed Oct. 13, 2006, which designated the U.S. PCT/AU2006/001507 is a Continuation-in-Part of U.S. Design application No. 29/258,084, filed Apr. 14, 2006, now D587,800, and PCT/AU2006/001507 claims the benefit of U.S. Design application No. 29/258,084, filed Apr. 14, 2006, and U.S. Provisional Patent Application Nos. 60/734,282, filed Nov. 8, 2005, 60/758,200, filed Jan. 12, 2006, 60/795,615, filed Apr. 28, 2006, 60/819,626, filed Jul. 11, 2006, and 60/838,442, filed Aug. 18, 2006, each of which is incorporated herein by reference in its entirety.

FIELD OF THE INVENTION

The present invention relates to a nasal assembly used for treatment, e.g., of Sleep Disordered Breathing (SDB) with Continuous Positive Airway Pressure (CPAP) or Non-invasive Positive Pressure Ventilation (NPPV).

BACKGROUND OF THE INVENTION

Some nasal assemblies used in the treatment of SDB are designed for insertion into or adjacent the nasal passages of the patient. Air or other breathable gas is supplied by a blower and passed along a flexible conduit to the nasal assembly.

The nasal assembly generally includes a relatively rigid shell, e.g., a frame, and a pair of nozzles (which may be in the form of nasal pillows, nasal prongs, cannula, or nasal puffs) that are mounted on the rigid shell and structured to be inserted into or adjacent the nasal passages of the patient. The nozzles are usually held in place using a headgear assembly, the relatively rigid shell and headgear assembly being joined using some form of connector.

One form of known nasal assembly is described in U.S. Pat. No. 4,782,832 (Trimble et al.). Trimble discloses a nasal puff assembly 20 that includes a nasal puff 22 adapted to be worn adjacent the nose of a patient, together with a harness assembly 24 adapted to be worn over the head of the patient. The harness assembly 24 is designed to operatively hold puff 22 adjacent and partially within the nasal passages of the patient.

The puff 22 is in the form of a generally Y-shaped rigid hollow plenum chamber 28 together with a pair of laterally spaced apart nares elements 30. Adjustability of the nares elements 30 may be provided by rotatably mounting the elements 30 to the plenum chamber 28 and mounting the elements 30 in slots permitting selective lateral positioning of the elements 30 with respect to each other. Also, the harness assembly 24 may be adjusted to adjust the fit and seal of the nares elements 30 during use. That is, the force required to maintain a sufficient seal is directly associated with the force required to maintain a desired fit. Thus, adjustment of the fit or stability of the nasal assembly directly affects the seal, which can adversely affect patient comfort.

Other examples of nasal pillows or cannula mounted to rigid shells are disclosed in U.S. Pat. Nos. 5,724,965 and 6,431,172.

A nasal mask assembly manufactured by Viasys, i.e., Spiritus, includes a plenum chamber with a pair of adjacent or laterally spaced nares elements. A harness assembly is engaged with the plenum chamber to adjust the fit and seal of the nares elements during use. Similar to Trimble, adjustment of the fit or stability of the nasal assembly directly affects the seal, which can adversely affect patient comfort.

A nasal mask assembly manufactured by InnoMed, i.e., Nasal Aire, includes a plenum chamber with a pair of adjacent or laterally spaced nares elements. The nares elements are structured to engage within the mucosal surfaces or internal passages of the patient's nose to maintain the nasal mask assembly on the patient's face and to provide a seal. See, e.g., U.S. Pat. No. 5,533,506.

A nasal mask assembly manufactured by Stevenson Industries (see U.S. Pat. No. 6,012,455), i.e., CPAP-Pro, includes a dental anchor, a platform, and air supply tubes having nasal pads, wherein the platform supports the air supply tubes. The dental anchor is sized to be engaged between the teeth in the patient's mouth so as to retain the assembly in place.

PCT Application Publication No. WO 00/13751 discloses a device that includes gas delivery elements positioned into engagement with the patient's nose by a mouthpiece fitted to the patient's teeth.

A common problem with known nasal assemblies, such as those discussed above, is patient comfort. For example, the prongs tend to irritate the patient's nose due to the tension applied by the headgear assembly that pulls the rigid shell and prongs towards the patient's nose.

Another problem is achievement of a sealing fit with the patient's nasal passages without sacrificing patient comfort.

Another problem is irritation of the inside of the patient's nostrils caused by contact with the prongs, e.g., an edge thereof.

Another problem is irritation of the inside of the patient's nostrils caused by air jetting (air flow irritation) from the prongs.

Another problem is adjustment of the nasal assemblies relative to the nose and/or head of the patient so as to accommodate various shapes and angles of patient's noses.

Still another problem is the direct association between sealing and stability forces that can affect patient comfort.

Still further nasal assemblies are known from the current assignee's co-pending U.S. Non-Provisional application Ser. No. 11/101,657, filed Apr. 8, 2005, and Ser. No. 10/781,929, filed Feb. 20, 2004, each incorporated herein by reference in its entirety.

A further need has developed to even further reduce the noise associated with the washout or venting of exhaled gases from the breathing chamber.

SUMMARY OF THE INVENTION

One aspect of the invention is directed towards a nasal assembly, in particular an improved cushion/frame/vent/clip assembly having an improved frame, cushion, vent and/or clip component. The assembly may effectively reduce the noise associated with gas washout or venting of the patient.

Another aspect of the invention is to prevent the use of an old-style frame (which has no vent holes) with a cushion as described herein (which also has no holes).

Another aspect of the invention is directed towards a frame that is easy and inexpensive to manufacture.

Another aspect of the invention is directed to a frame with a vent channel and a plurality of vent holes, in which case it is not necessary to provide the cushion with such gas washout vent holes.

According to another aspect of the invention, the clip may have ribs to improve strength/stiffness, and/or to allow ease of grip. The clip may also have wings with compound curvature to help improve strength/stiffness.

Another aspect of the invention provides a nasal assembly for delivering breathable gas to a patient. The assembly includes a frame having a main body and lateral sides, each lateral side including an integrally formed lateral connector; and a cushion including a pair of nozzles to communicate with nasal passages of a patient's nose in use, the cushion being coupled with the main body of the frame, wherein the frame includes a vent channel provided in the main body, the vent channel including a pair of side walls extending from the main body towards a base wall, said base wall including at least one vent hole.

According to another aspect of the invention, there is provided a nasal assembly for delivering breathable gas to a patient, comprising a frame having a main body and lateral sides, each lateral side including an integrally formed lateral connector; and a cushion including a pair of nozzles to communicate with nasal passages of a patient's nose in use, the cushion being coupled with the main body of the frame, wherein the frame includes a plurality of vent holes, said vent holes being provided in two or more rows arranged such that the vent holes are offset from one another.

According to another aspect of the invention, there is provided a nasal assembly for delivering breathable gas to a patient, comprising a frame having a main body and lateral sides, each lateral side including an integrally formed lateral connector; and a cushion including a pair of nozzles to communicate with nasal passages of a patient's nose in use, the cushion being coupled with the main body of the frame, wherein the frame includes longitudinal cushion channels to receive longitudinal edges of the cushion, at least one of said cushion channels including at least one cut out to receive a lug of the cushion upon assembly.

According to another aspect of the invention, there is provided a nasal assembly for delivering breathable gas to a patient, comprising a frame having a main body and lateral sides, each lateral side including an integrally formed lateral connector; and a cushion including a pair of nozzles to communicate with nasal passages of a patient's nose in use, the cushion being coupled with the main body of the frame, wherein the frame includes a circumferential cushion channel provided to each said lateral side of the frame, said frame including a cored portion generally aligned with each circumferential cushion channel, said cushion including a corner lug to interface with each said cored portion.

According to another aspect of the invention, there is provided a nasal assembly for delivering breathable gas to a patient, comprising a frame having a main body and lateral sides, each lateral side including an integrally formed lateral connector, the frame including at least one vent hole; a cushion including a pair of nozzles to communicate with nasal passages of a patient's nose in use, the cushion being coupled with the main body of the frame; and a clip to secure the cushion to the frame, wherein the clip includes a vent window generally aligned with the at least one vent hole.

According to still another aspect of the invention, there is provided a patient interface for delivering breathable gas to a patient, comprising a frame; a cushion to communicate with a patient's airways in use, the cushion being coupled with the frame; and a vent portion including a plurality of vent holes, said vent holes being provided in two or more rows and the rows being arranged such that the vent holes are offset from one another.

Yet another aspect of the invention relates to a full-face mask frame including a main body having a longitudinal axis and a vent assembly provided to the main body. The vent assembly includes a plurality of holes arranged in at least one column. The at least one column is aligned with or parallel to the longitudinal axis.

Yet another aspect of the invention relates to a mask frame including a main body and a side frame portion provided on each lateral side of the main body. A vent assembly is provided to each side frame portion. Each vent assembly includes a plurality of holes arranged in a multi-column pattern and each column is vertically staggered with respect to one another.

Yet another aspect of the invention relates to a nasal assembly for delivering breathable gas to a patient. The nasal assembly includes a frame and a cushion including a pair of nozzles to communicate with nasal passages of a patient's nose in use. The cushion is coupled with the frame. The cushion includes a size indicator, a series of position arrows, text, and/or a logo provided to one side of the cushion. The size indicator, series of position arrows, text, and/or logo are adapted to provide a visual cue to assist the patient in achieving correct alignment and orientation of the cushion and frame with respect to the patient in use.

Yet another aspect of the invention relates to a nasal assembly for delivering breathable gas to a patient. The nasal assembly includes a frame including a main body and a cushion including a pair of nozzles to communicate with nasal passages of a patient's nose in use. The cushion is coupled with the main body of the frame. The frame includes a vent channel provided in the main body. The vent channel includes a pair of side walls extending from the main body towards a base wall. Each of the side walls includes a variable wall thickness along its length.

Yet another aspect of the invention relates to a nasal assembly for delivering breathable gas to a patient. The nasal assembly includes a frame and a cushion coupled to the frame. The cushion includes a pair of nozzles to communicate with nasal passages of a patient's nose in use. The frame includes a vent channel that leads to at least one vent hole. The vent channel is adapted to buffer and/or separate higher velocity and more turbulent air flow into and around the frame from an entrance to the at least one vent hole.

Yet another aspect of the invention relates to a mask frame including a main body including an aperture adapted to communicate with an elbow and a vent assembly provided to the main body. The vent assembly includes a plurality of holes arranged around the aperture.

Other aspects, features and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIG. 85 is a schematic view of the vent assembly shown in FIG. 84;

FIGS. 86-87 illustrate an elbow according to an embodiment of the present invention; and FIG. 88 illustrates an elbow retaining clip according to an embodiment of the present invention, the elbow retaining clip adapted for use with the elbow shown in FIGS. 86-87.

DETAILED DESCRIPTION OF ILLUSTRATED EMBODIMENTS

The following includes a description of one or more illustrated embodiments of the present invention. Each illustrated embodiment includes features that may be used with and/or in the other embodiments, or with the embodiments and/or components described in U.S. Non-Provisional application Ser. No. 10/781,929 and/or Ser. No. 11/101,657, as would be apparent to those of ordinary skill in the art. The general operation of the embodiments described herein is substantially identical to the operation of the embodiments detailed in U.S. Ser. No. 10/781,929 and U.S. Ser. No. 11/101,557, and therefore will not be repeated.

1.0 Overall Nasal Assembly

Figure 1:
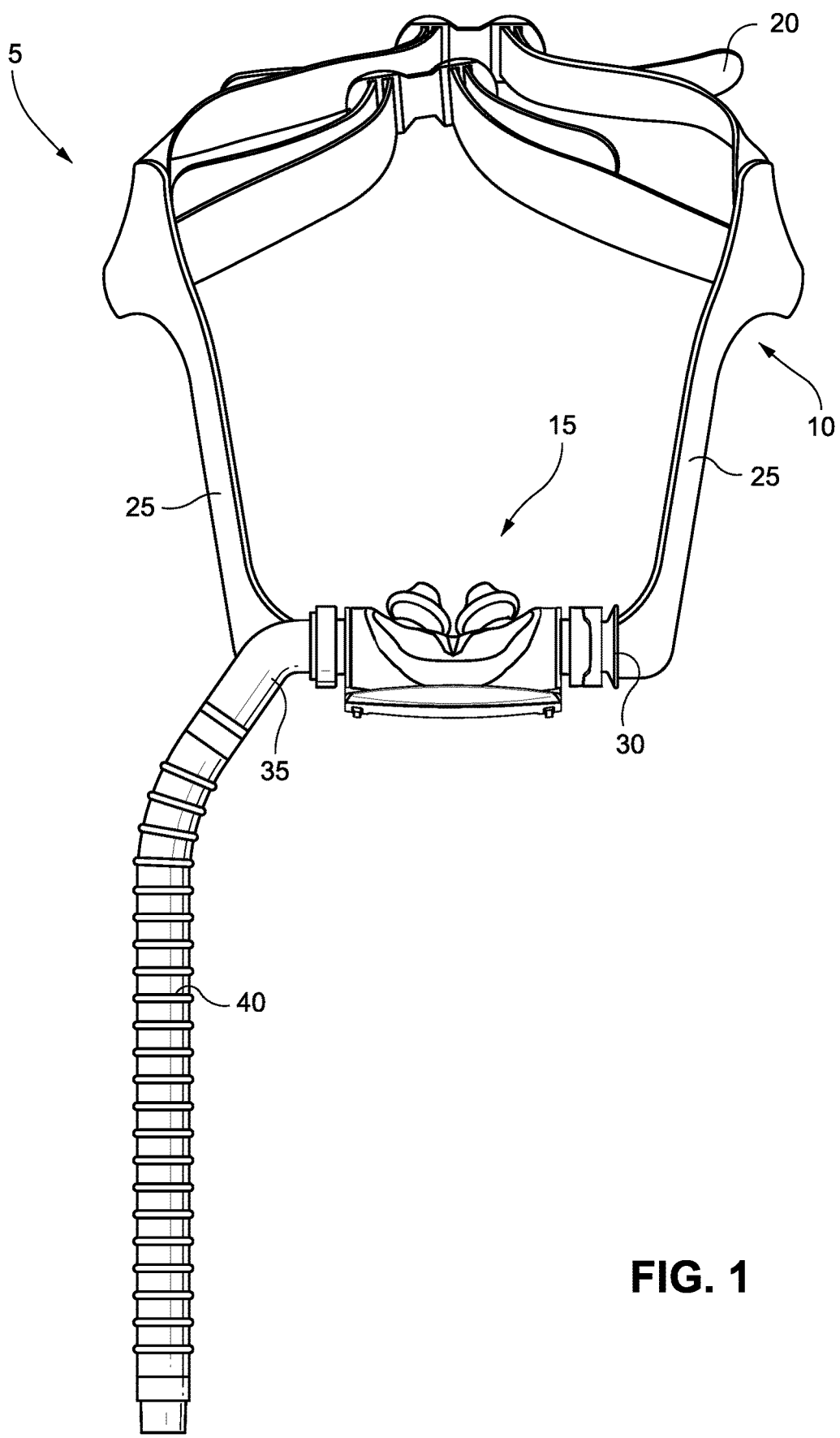
FIG. 1 is a perspective view of a nasal assembly according to an embodiment of the present invention.

FIG. 1 illustrates a nasal assembly 5 according to an embodiment of the present invention. As shown in FIG. 1, nasal assembly 5 includes headgear 10 and a cushion assembly 15. Headgear 10 is designed to capture the crown of the patient's head. Adjustment of strap tension can be accomplished by pulling loose tabs 20 on the top of the head in opposite directions. The pulling direction is not aligned with the force the nozzle assembly applies to the patient. Therefore, the patient is more isolated from the strap adjustment forces. Yokes 25 provide stability to the sides. Yokes 25 retain at least a partial portion of the basic shape of headgear, which facilitates donning of the headgear. Headgear need not include adjustability toward front of the face, as all adjustment of headgear can be effected at the back or top of the head.

In the embodiment of FIG. 1, one end of the cushion assembly 15 is provided with a plug 30 and the other end is provided with a swivel elbow 35. The positions of the swivel elbow 35 and the plug 30 may be interchanged, according to preference, e.g., the typical sleeping position of the patient. An air delivery tube 40 is joined to the swivel elbow 35. The air delivery tube 40 may include a swivel connector and includes an end which also may be provided with a swivel connector. The end is provided with a source of pressurized gas.

As shown in FIG. 1, the elbow 35 is angled about 120° from the cushion assembly 15. This helps to keep the tube out of line of sight, to minimize pressure drop and to maintain the flexion point of tube as close to the face as possible. However, the elbow may have a typical 90° bend.

Figure 2:
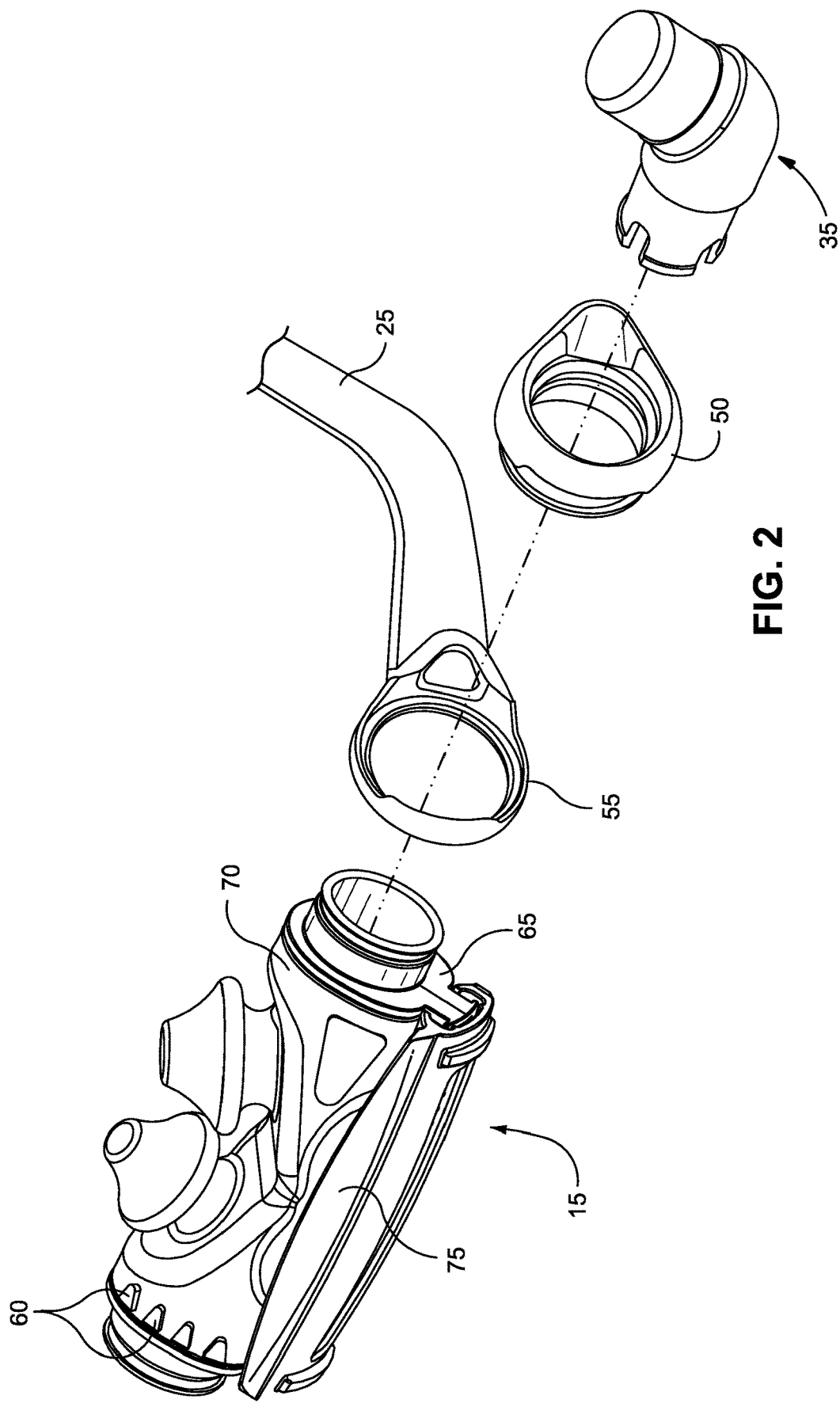
FIG. 2 is an exploded view illustrating a portion of the nasal assembly shown in FIG. 1.

FIG. 2 is an exploded view of a portion of the nasal assembly 5 shown in FIG. 1, including the cushion assembly 15, yoke 25, seal portion 50 and elbow 35 (the other side of the cushion assembly is provided with a yoke, seal portion and an elbow or plug). The yoke 25 may include a yoke ring 55. The cushion assembly 15 may be adjustably rotated with respect to headgear, to a position which best fits the patient. The ring of the yoke associated with the other side of the headgear (not shown) may include an alignment marker that can be selectively aligned with one of a plurality of alignment markers 60 provided on the cushion.

2.0 Cushion Assembly

Cushion assembly 15 includes a frame 65, a cushion 70 and a clip 75. FIGS. 3-10 show the frame in isolation, FIGS. 11-20 show the cushion in isolation, FIGS. 21-26 show the clip in isolation, and FIGS. 27-34 show the assembly of the frame, cushion and clip.

2.1.0 Frame

Figure 3:
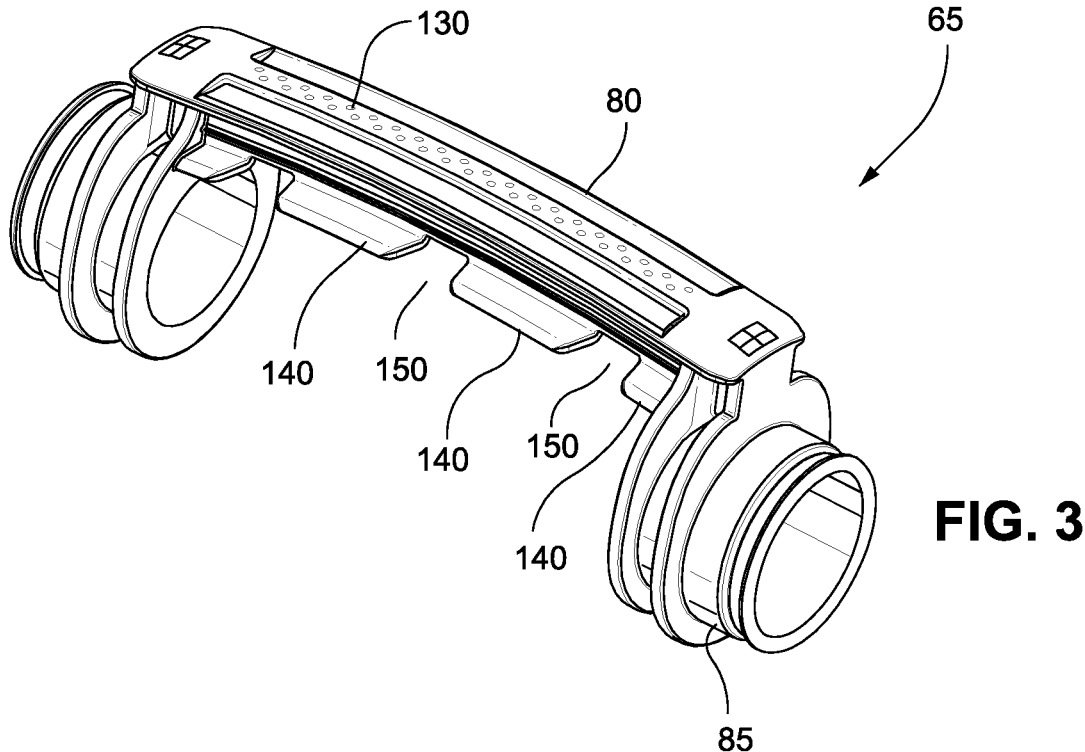
FIG. 3 is a perspective view of a frame according to an embodiment of the invention.

As shown in FIG. 3, frame 65 has a main body 80 and lateral sides. Each lateral side includes a lateral connector portion 85. Frame 65 is preferably made of molded plastic, e.g., polycarbonate and/or polypropylene.

2.1.1 Vent Channel

Main body 80 of frame is provided with a vent channel 90 defined by a base wall 92 and a pair of side walls 94. Vent channel 90 extends from an inside surface 95 of the main body toward the base wall 92. An upper portion 100 of the vent channel 90 is positioned in a plane just below the lowest point 110 of the inlet aperture 115 of lateral connector 85.

Side walls 94 converge towards one another in the direction of the base wall at a slight angle alpha ($\alpha$), e.g., about 2-5 degrees, preferably 2 degrees. Each side wall 94 has a lower portion 120 that is provided to the base wall 92 along a radius of curvature RL of about 0.2-0.4 mm, preferably about 0.3 mm, and the upper portion 100 that is curved, e.g., with a radius of curvature RU of between about 0.5 to 1.5 mm, preferably about 0.9 to 1.0 mm. The width WS between the side walls is about 2-3 mm, preferably about 2.6 mm. The width between the side walls increases in the direction of upper portion 100 due to the angle alpha ($\alpha$), described above.

2.1.2 Vent Holes

Figure 5:
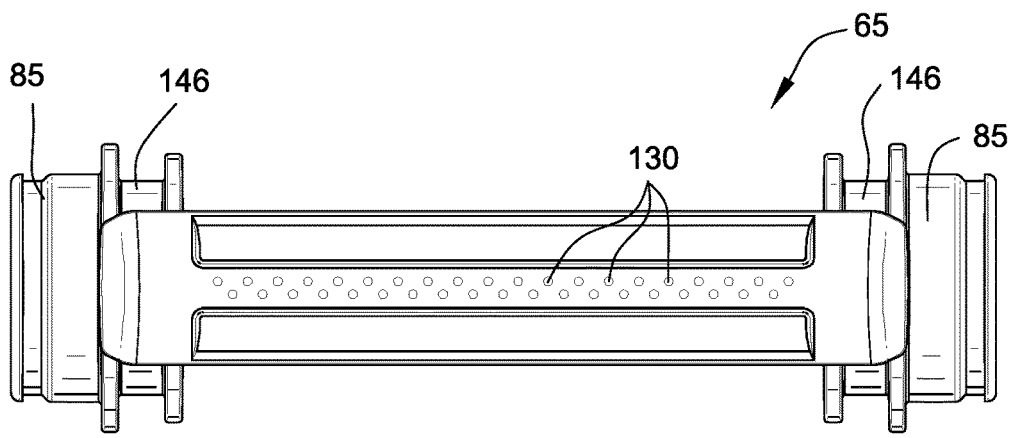
FIG. 5 is a front view thereof.

Channel 90 is in communication with a plurality of vent holes 130, e.g., 6-60 vent holes, and preferably about 35-45 vent holes, although there could be more than 60 holes or less than 6 holes, depending on application. In the example of FIG. 5, there are 39 holes. Each vent hole 130 has a generally part conic shape, including opposed walls 135 that converge from a larger diameter to a smaller diameter, as viewed in the direction of exhausted gas. The walls 135 preferably converge at an angle beta ($\beta$), i.e., an included angle, of about 1-90 degrees, and preferably 2-8 degrees, and even more preferably about 5 degrees. Each wall preferably has a radius of curvature HR of about 0.15-0.35 mm, preferably 0.25 mm.

Figure 35:
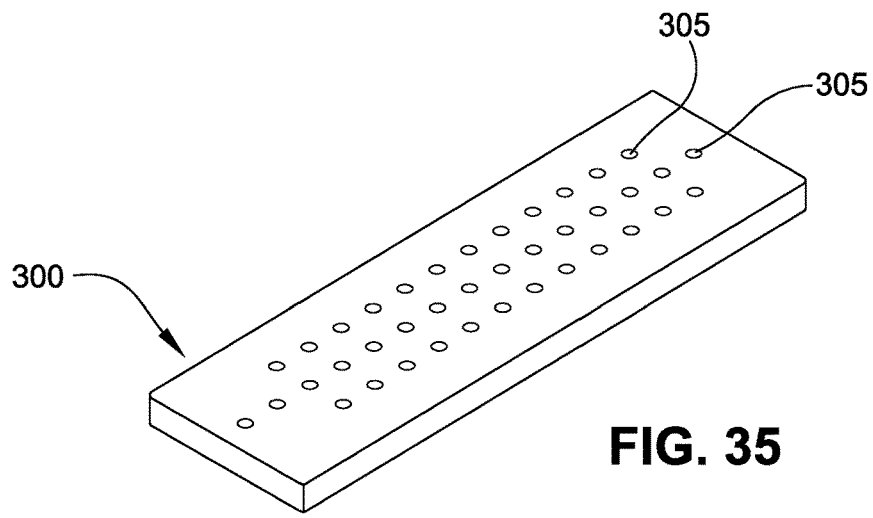
FIG. 35 illustrates a vent assembly according to another embodiment of the present invention.

FIGS. 3, 5, 6 and 9 illustrate one possible vent arrangement that includes offset rows of vent holes. However, other arrangements are possible. For example, FIG. 35 illustrates a portion of a vent assembly 300 having a plurality of holes 305, e.g., 5-10 holes or more, arranged in a pattern by three rows of holes 305. The center row includes one or more additional holes at each end thereof. The positioning of the assembly 300 is similar to that shown in FIG. 3.

Figure 36:
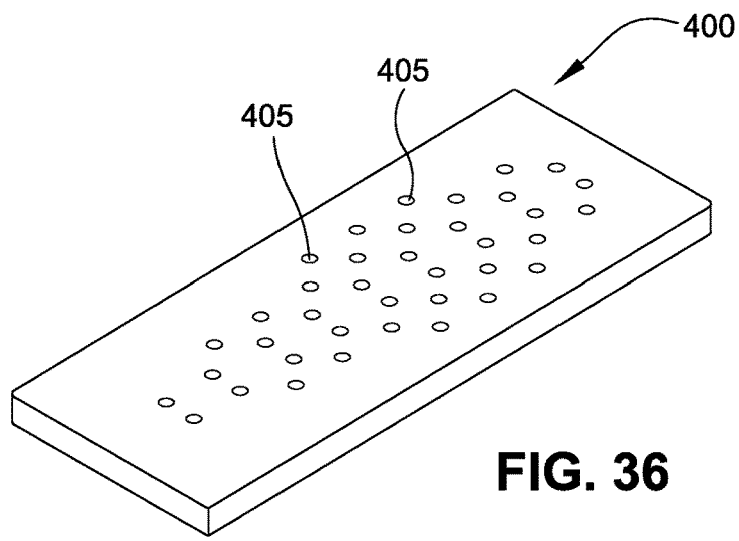
FIGS. 36 and 37 illustrate a vent assembly according to another embodiment of the present invention.
Figure 37:
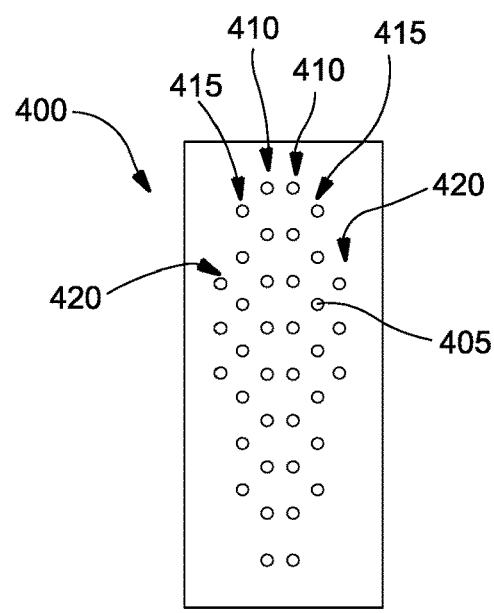
Figure 38:
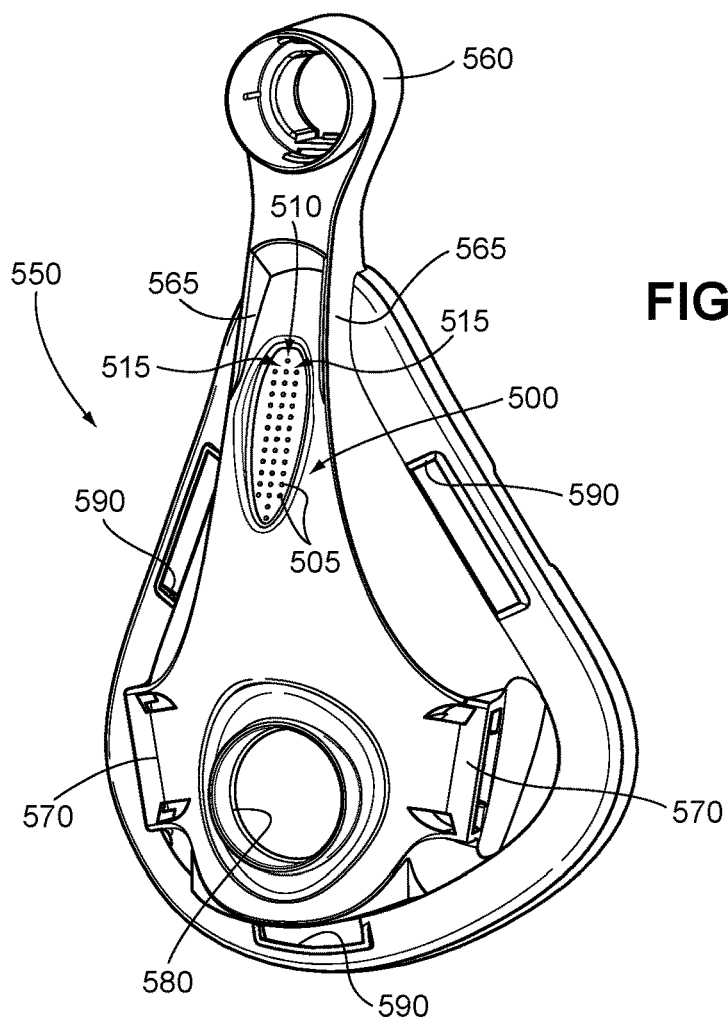
FIGS. 38-44 illustrate various views of a mask frame including a vent assembly according to another embodiment of the present invention.
Figure 39:
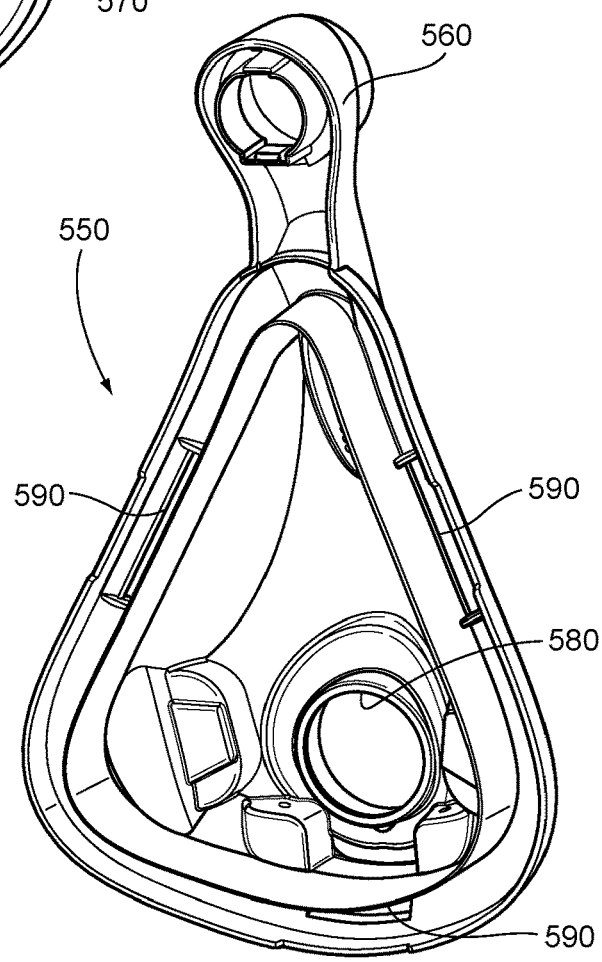
Figure 41:
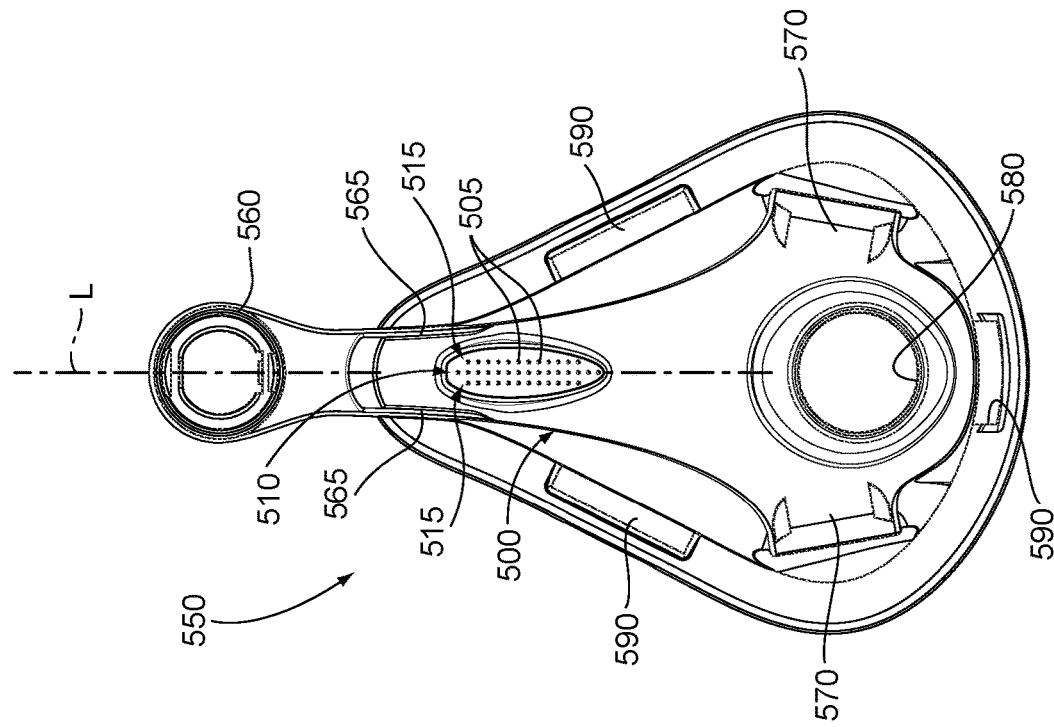
Figure 40:
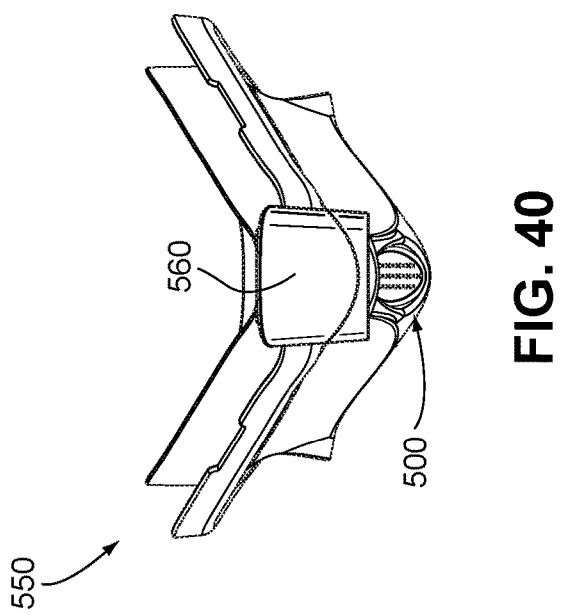
Figure 42:
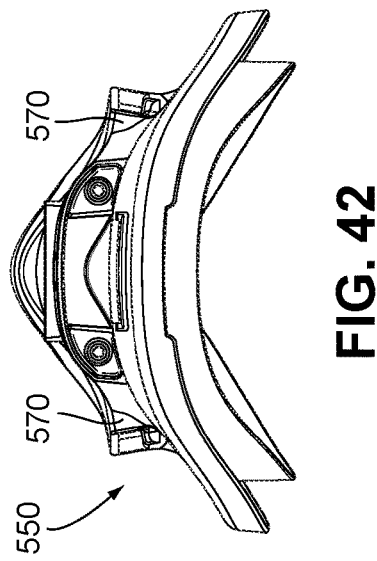
Figure 43:
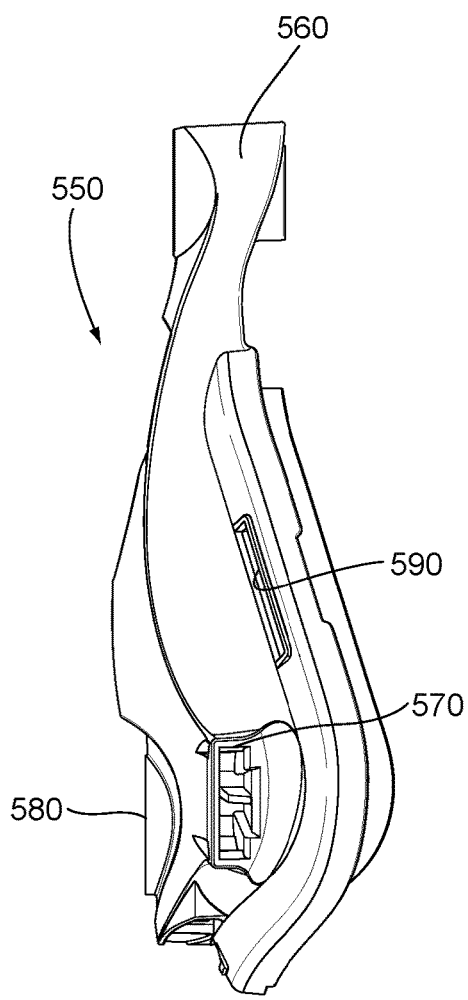
Figure 44:
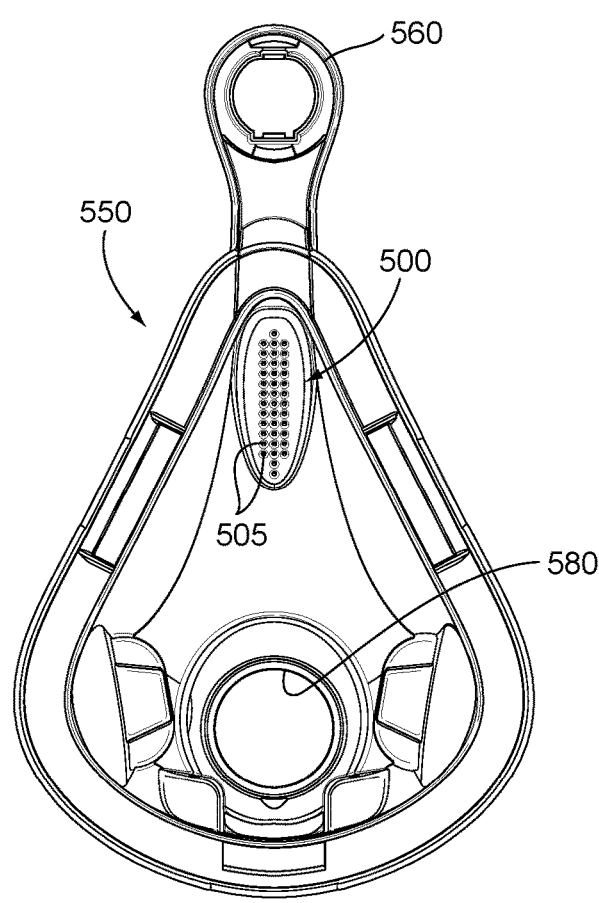
Figure 45:
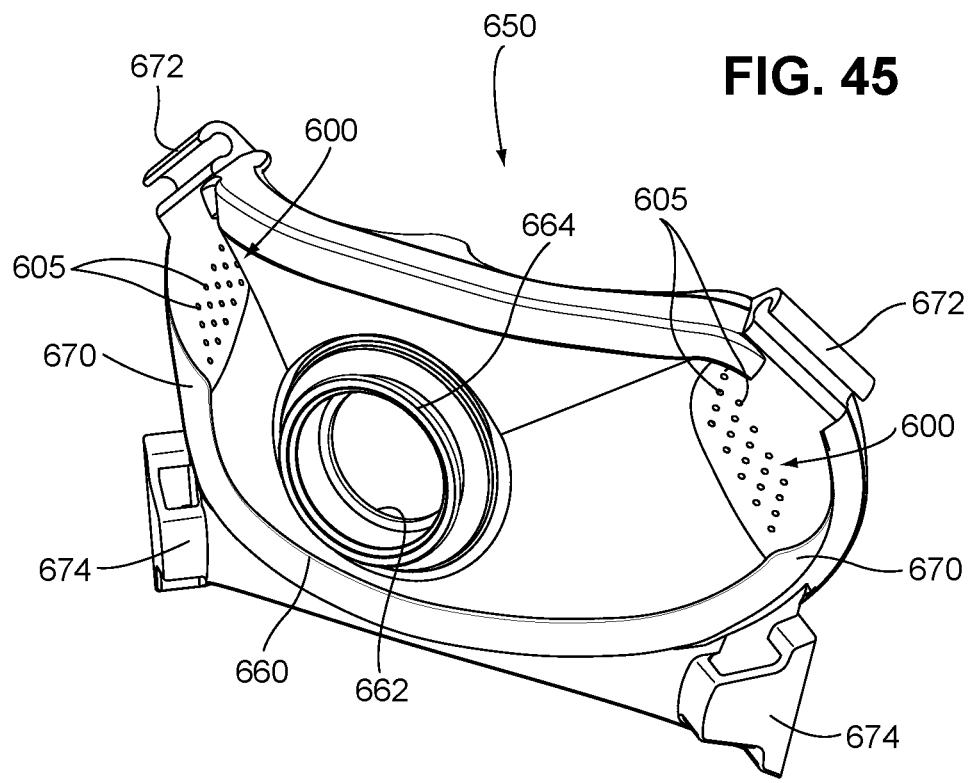
FIGS. 45-52 illustrate various views of a mask frame including a vent assembly according to another embodiment of the present invention.
Figure 46:
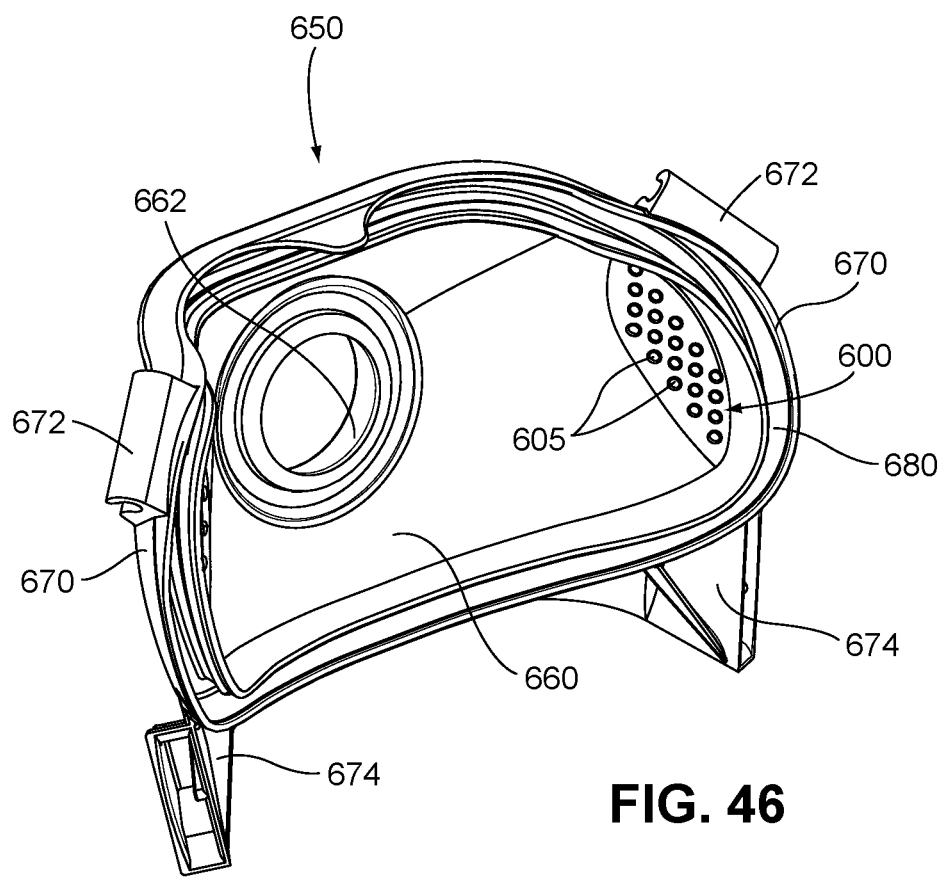
Figure 47:
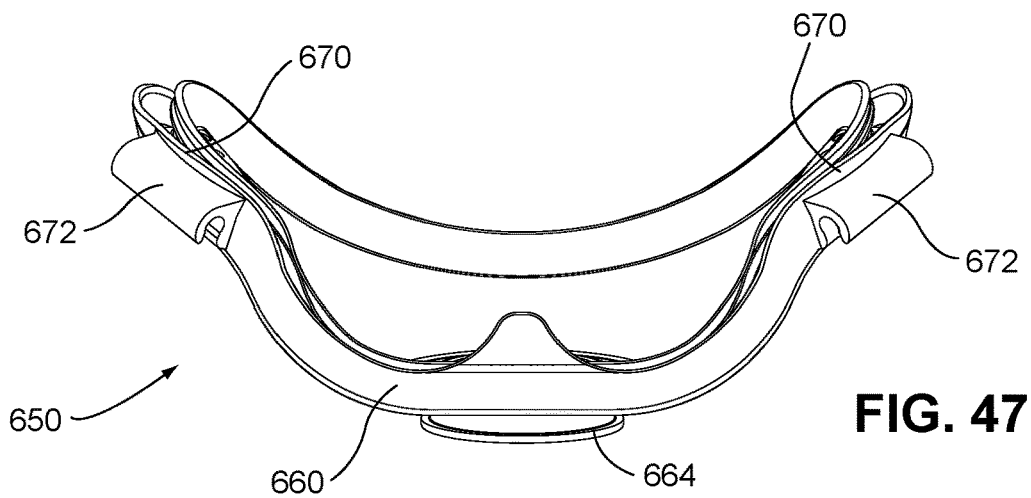

FIG. 36 illustrates a portion of a vent assembly 400 according to yet another embodiment of the invention. Vent assembly 400 includes a plurality of vent holes 405 arranged in a predetermined pattern. FIG. 37 is a plan view of the pattern which includes center rows 410 each including nine holes in side-by-side relation. Each center row 410 is flanked by an intermediate row 415, which in turn is flanked by outside rows 420. Each intermediate row 415 includes seven holes, while each outside row 420 includes three holes. The holes in outside rows 420 are aligned with holes in the center rows 410, while the holes in intermediate rows 415 are offset from both the center rows 410 and the outside rows 420. Furthermore, it should be appreciated that any of the vent configurations described above, especially the embodiments described in relation to FIGS. 35-37, could be incorporated into a nasal mask (e.g., ResMed's Mirage® nasal mask) or a full-face (nasal-oro) mask (e.g., ResMed's Ultra-Mirage® full face mask).

The vent holes in any of the above embodiments may be provided directly on the frame and/or the cushion. In an alternative, the frame, cushion and/or air delivery conduit can be provided with an aperture into which a substrate with the holes is inserted or otherwise provided. The substrate may take the form of an insert, such as disclosed in U.S. Pat. No. 6,561,190, incorporated herein by reference in its entirety. In another alternative, vent holes may be provided in headgear.

Figure 6:
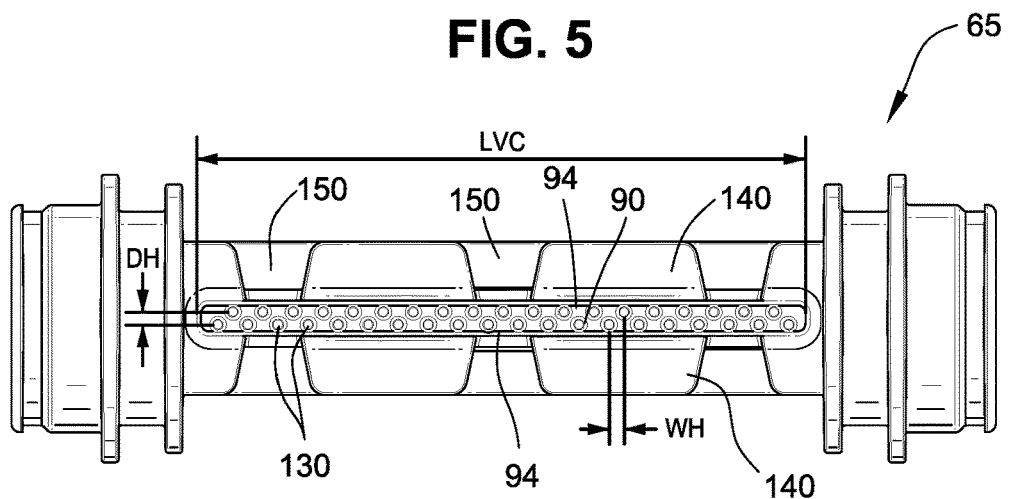
FIG. 6 is a rear view thereof.
Figure 7:
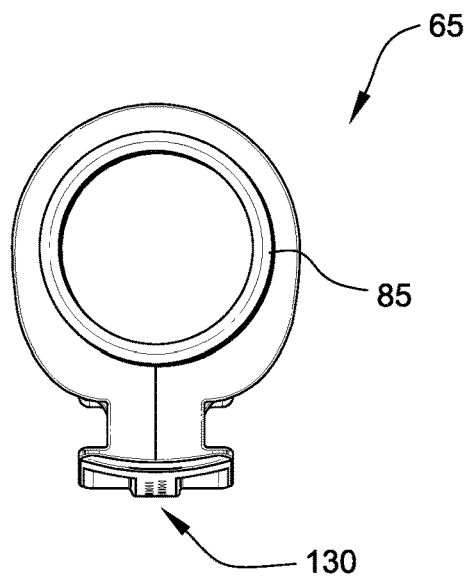
FIG. 7 is a side view thereof.
Figure 8:
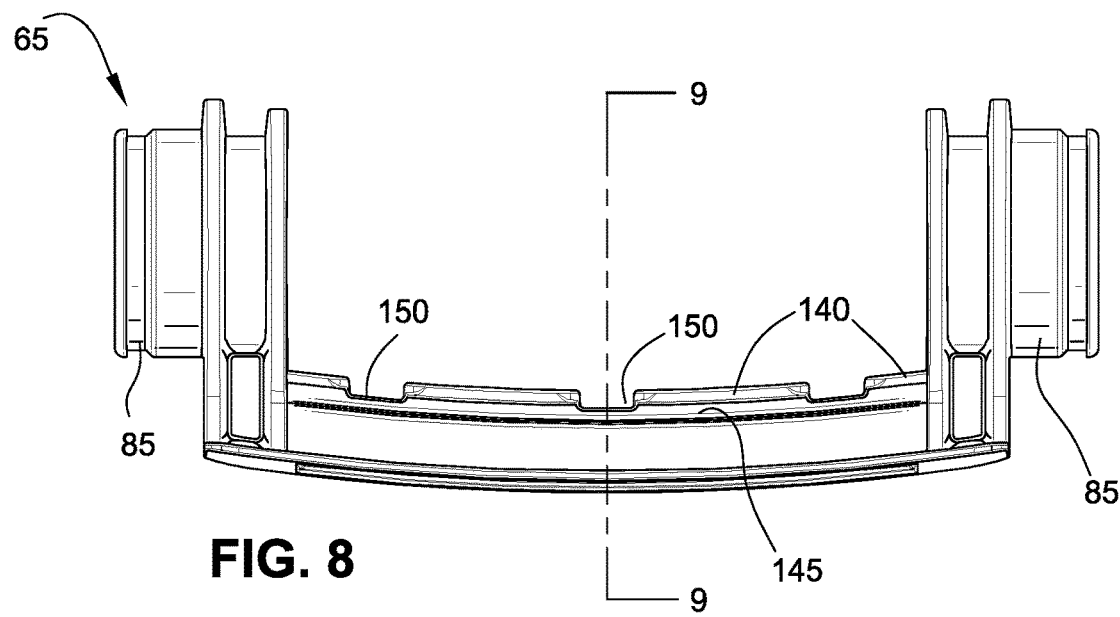
FIG. 8 is a top view thereof.
Figure 9:
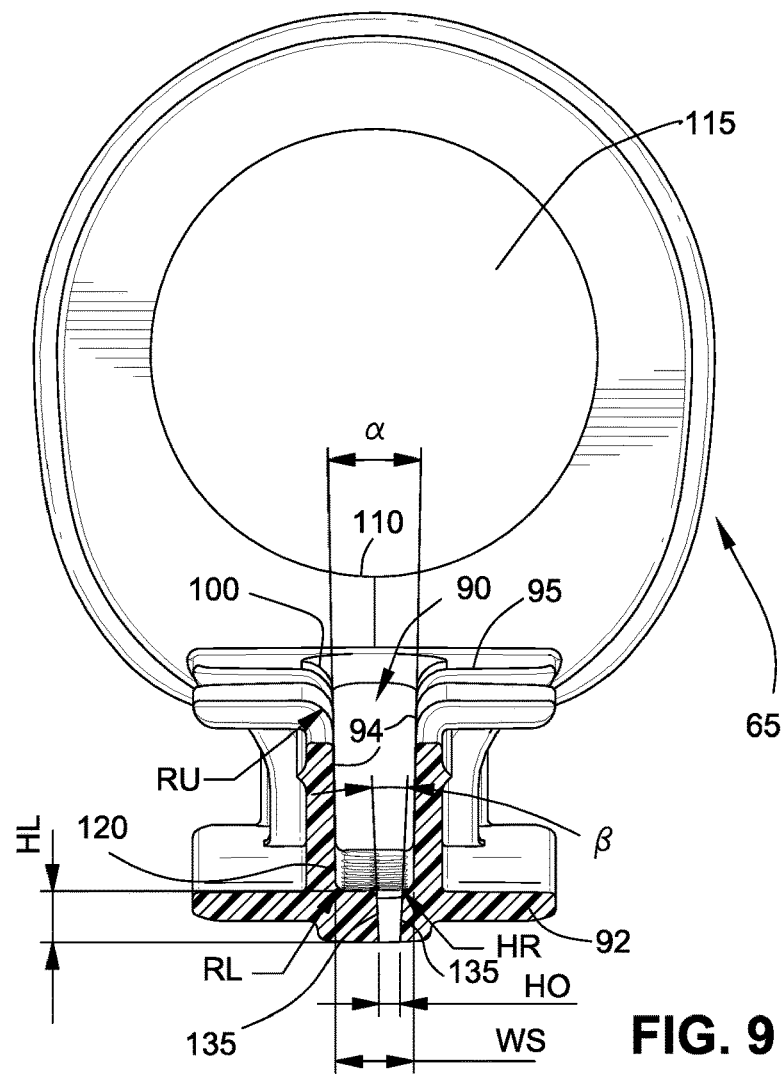
FIG. 9 is a cross-sectional view along line 9-9 of FIG. 8.
Figure 10:
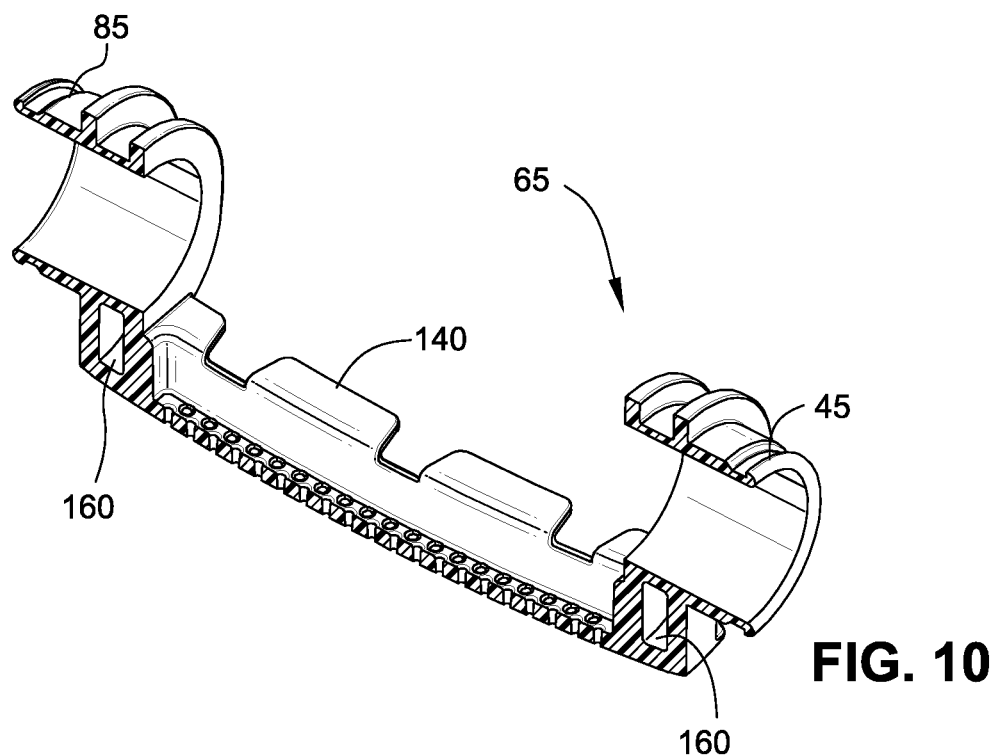
FIG. 10 is a cross-sectional view along a longitudinal axis of the frame, through one of the rows of vent holes.
Figure 11:
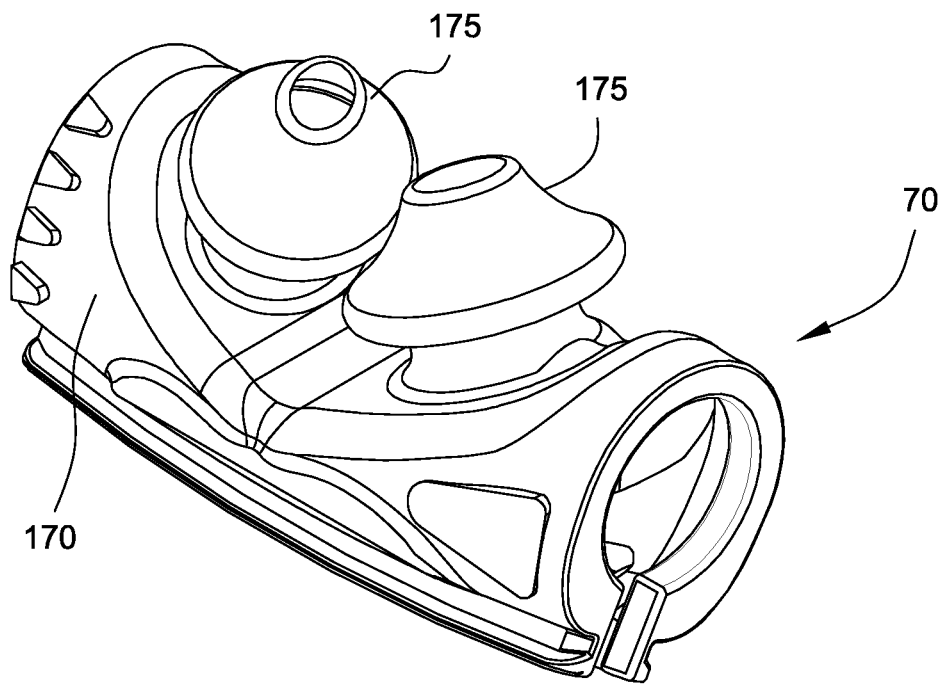
FIG. 11 is a perspective view of a cushion according to an embodiment of the present invention.
Figure 12:
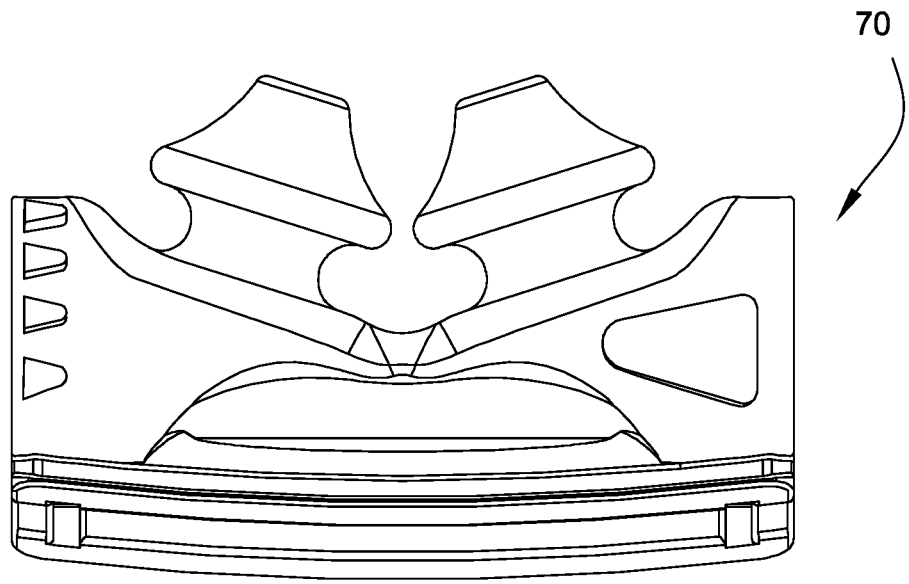
FIG. 12 is a front view thereof.
Figure 13:
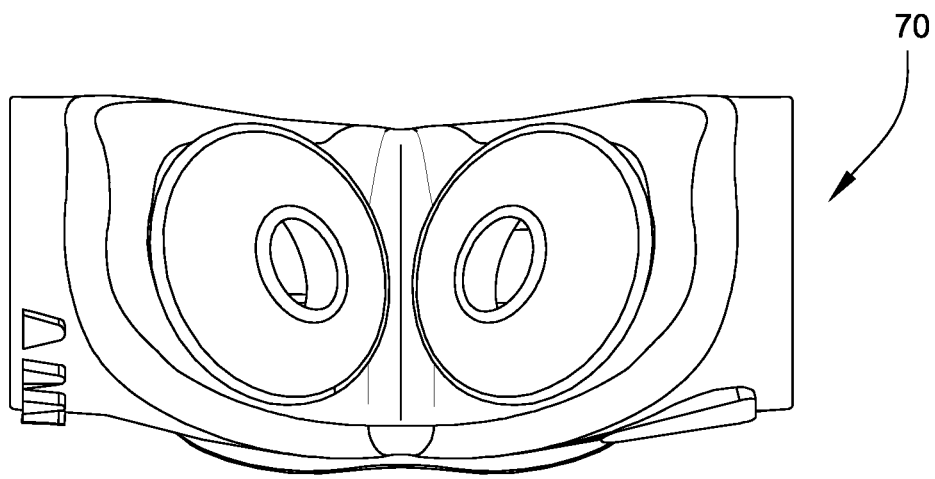
FIG. 13 is a top view thereof.
Figure 14:
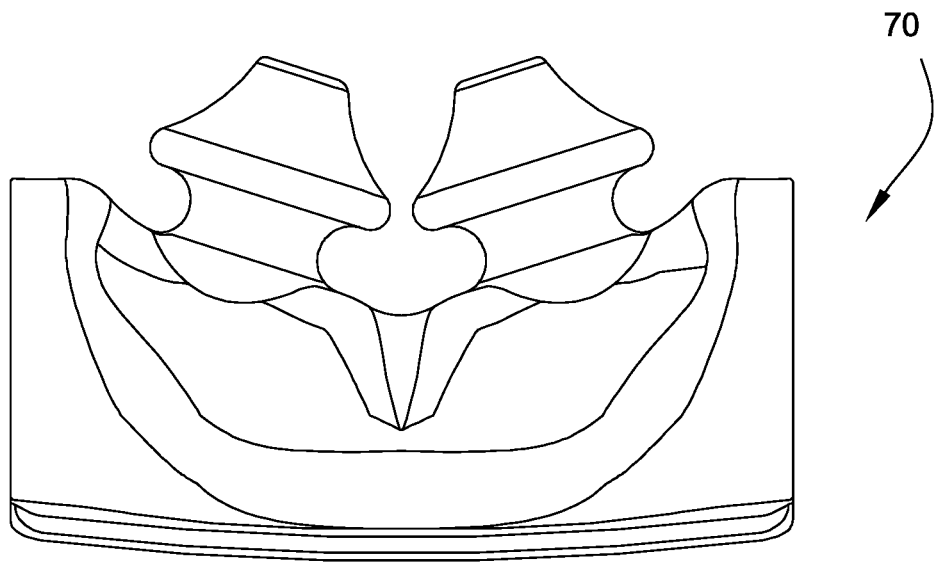
FIG. 14 is a rear view thereof.
Figure 15:
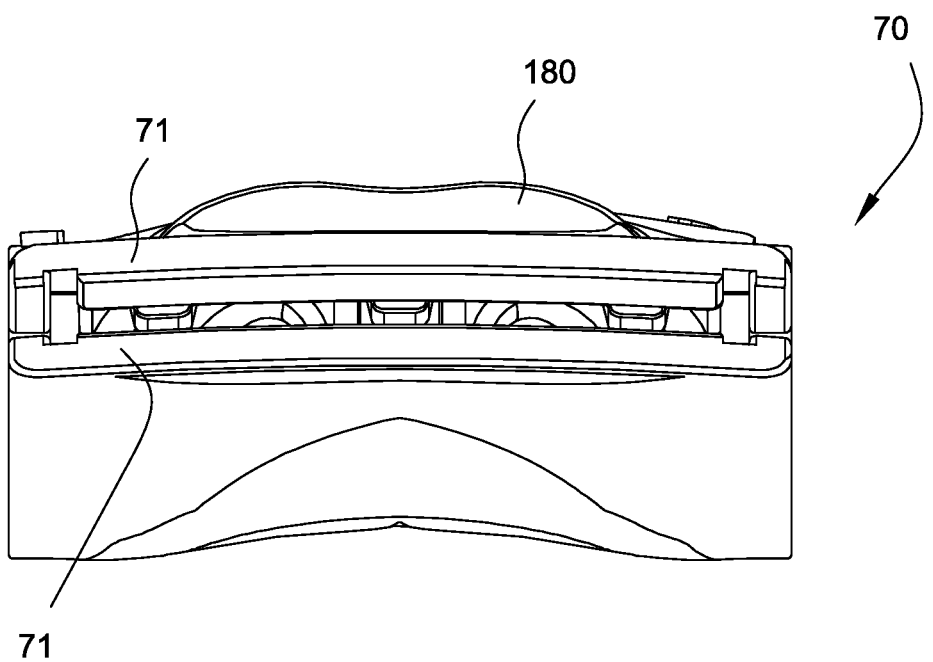
FIG. 15 is a bottom view thereof.
Figure 16:
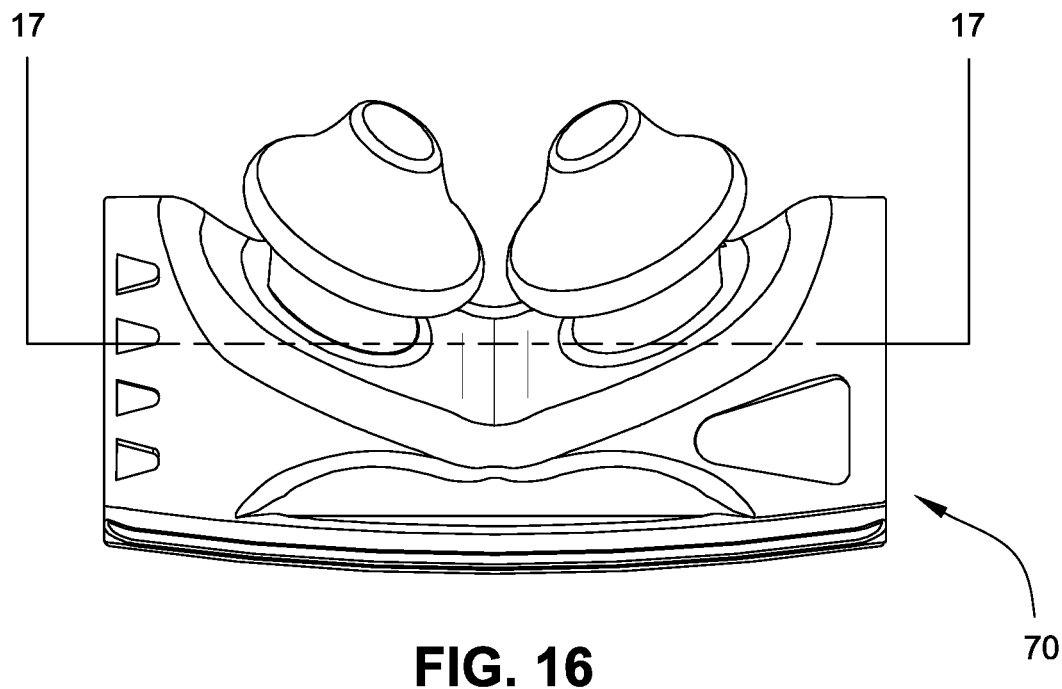
FIG. 16 is a front view similar to the front view of FIG. 12, but from slightly different orientation.

As can be seen from FIGS. 5, 6 and 9, the holes 130 are preferably arranged in two rows having a predetermined pitch. For example, the rows are offset to allow more holes to be fitted into a smaller space, thereby keeping the size of the vent channel 90 to a minimum. As seen in FIG. 6, the centers of holes in adjacent rows are spaced a depth DH of about 0.75 to 1.25 mm, preferably 1.0 mm, and a width WH of about 1.1-1.3 mm, preferably about 1.175 mm. The center-to-center distance ("true pitch") between the holes is about 1.5-1.6 mm, preferably about 1.54 mm. The length LVC of the vent channel is about 45-55 mm, preferably about 48 mm.

Each hole 130 preferably has the following dimensions: length HL: about 1.0-2.5 mm, preferably about 1.7 mm; outlet diameter HO: about 0.5-1.0 mm, preferably about 0.7 mm; radius of curvature at the upper end of the hole (HR): about 0.15-0.35 mm, preferably about 0.25 mm.

2.1.3 Cushion Channels and Cut Outs

Figure 4:
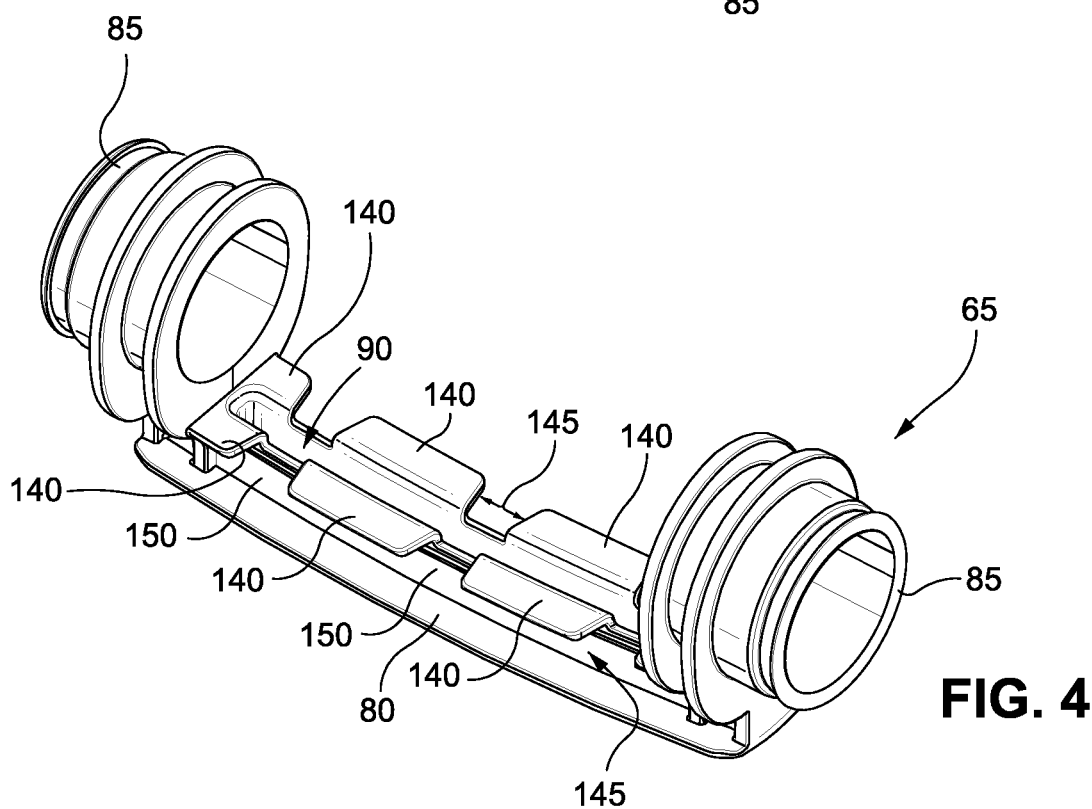
FIG. 4 is a reverse perspective view thereof.

Frame 65 includes lugs 140 (FIGS. 3, 4, 6, 8 and 10) to help form a longitudinal cushion channel 145 into which an edge portion 71 of the cushion 70 is fitted, to secure the cushion relative to the frame to form a frame/cushion subassembly prior to attachment of the clip. As shown in FIG. 4, cushion channel 145 is provided on each side of the vent channel. Cushion channel 145 is provided with structure to enhance alignment with the cushion. For example, each cushion channel 145 may include one or more cut outs 150 to receive corresponding lugs 155 (e.g., FIG. 20) of the cushion (described below). Frame also includes circumferential channels 146 (FIG. 5) to receive end portions 72 of the cushion 70.

2.1.4 Coring

Frame includes cored portions 160 (FIG. 10) adjacent to each lateral connector. Cored portions 160 help facilitate manufacturing, by thinning out the plastic section. A thickened section has a higher possibility of leaving sink marks.

2.1.5 Noise Reduction

The vent channel 90 of the frame 65 is structured to reduce vent noise generated by the vent holes. In the illustrated embodiment, the entrance to the vent holes 130 is located at the bottom of the vent channel 90. As a result, turbulent inflow is entrained into or guided within the vent channel 90 which decreases the turbulence of the flow in the mask chamber before the flow passes into the vent holes 130. Because the flow entering the vent is not highly turbulent, the noise induced by turbulent flow passing through the vent is reduced (effecting a noise reduction throughout the whole breathing cycle, not just inhalation).

The vent channel 90 also acts as a buffer between the high flow region (generally between the opposed inlet apertures 115) and the entrance to the vent holes 130. This arrangement has the effect of quieting the nasal assembly during inhalation when flow through the nasal assembly is at its highest and most turbulent.

Specifically, inflow during inhalation includes a relatively high velocity cross flow, wherein air enters the cushion assembly 15 laterally and normal to the orientation of the vent holes 130. Noise may be produced by this air flow if it encounters obstructions or irregularities, such as an array of vent holes. By providing the vent holes 130 at the bottom of the vent channel 90, the air flow does not directly encounter this irregular geometry. Therefore, noise generated from the vent holes 130 may be eliminated and/or reduced.

2.2.0 Cushion

Cushion 70 includes a main body 170 supporting a pair of nozzle members 175 that are designed to engage with a user's nares in use.

2.2.1 Lugs

Figure 17:
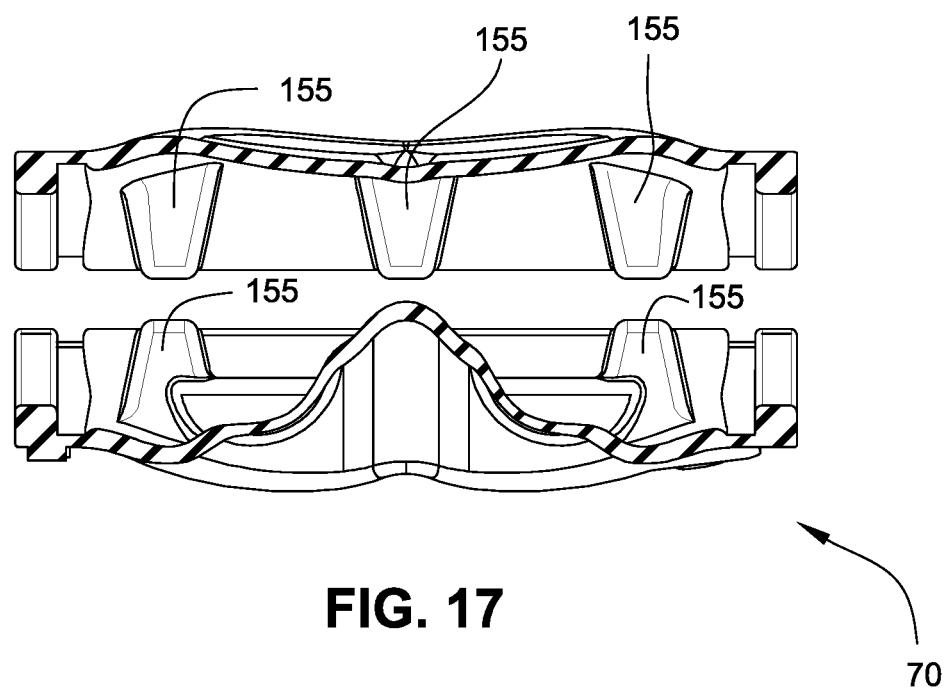
FIG. 17 is a cross-sectional view along line 17-17 in FIG. 16.
Figure 18:
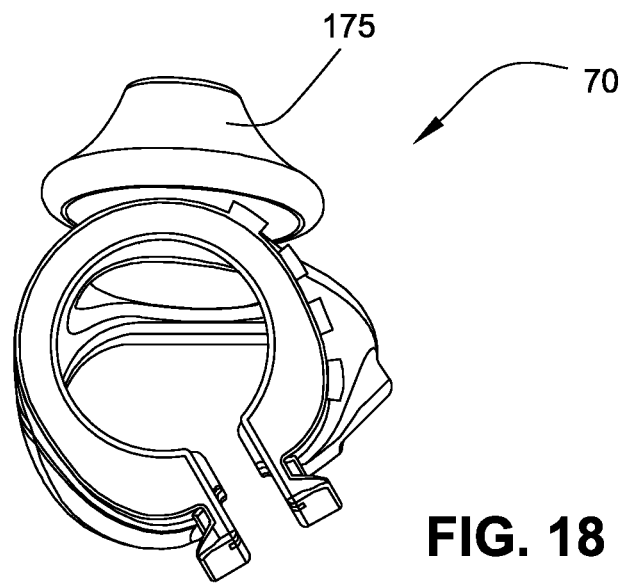
FIG. 18 is a left side view thereof.
Figure 19:
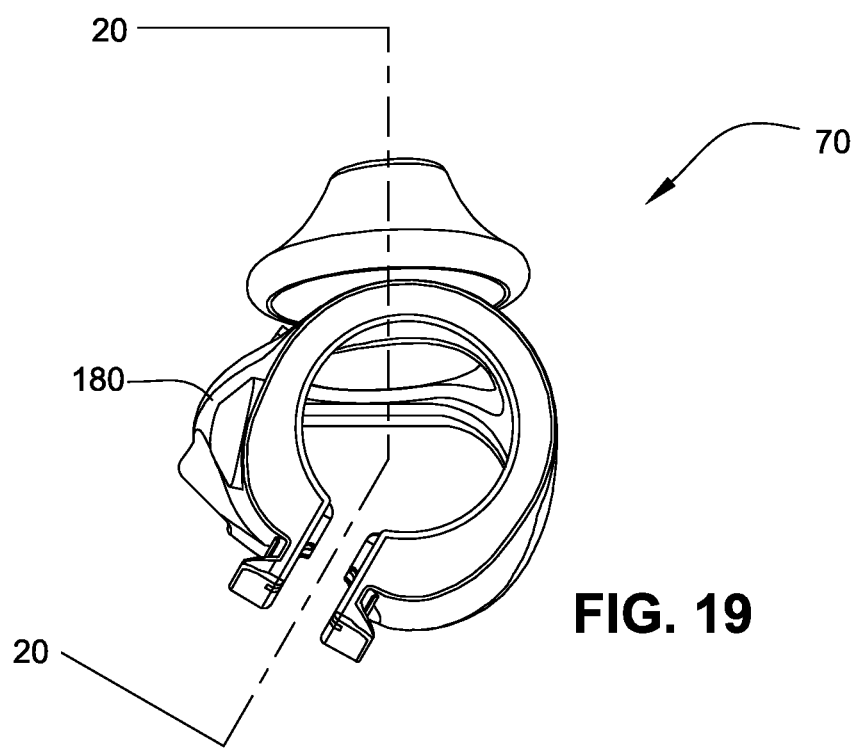
FIG. 19 is a right side view thereof.
Figure 20:
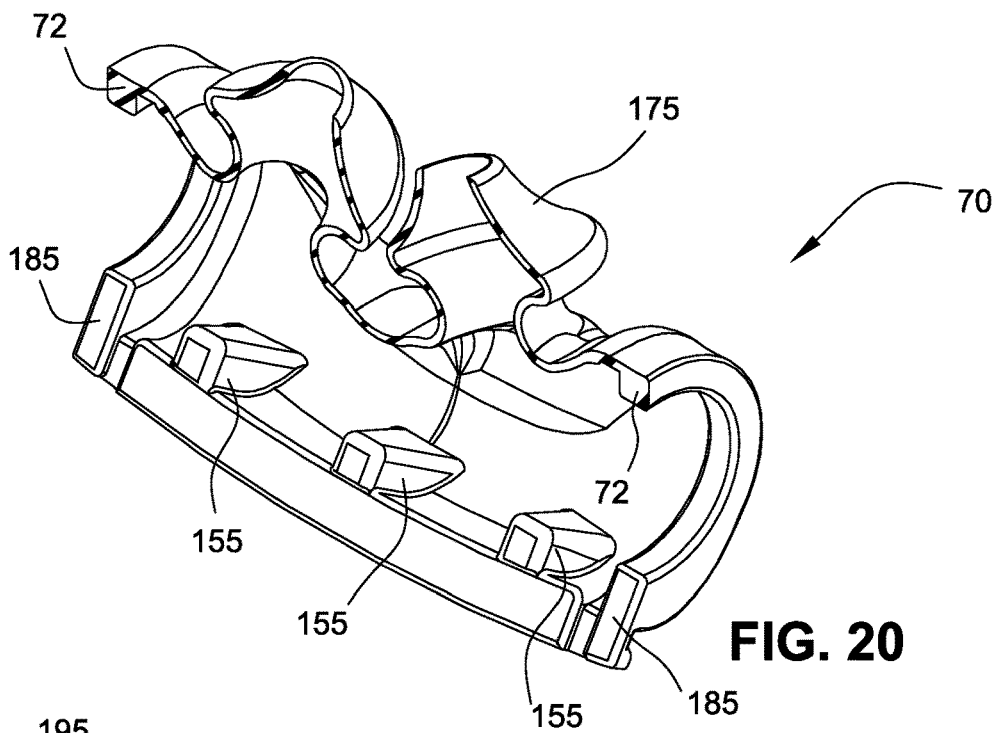
FIG. 20 is a perspective cross-sectional view along line 20-20 in FIG. 19.
Figure 21:
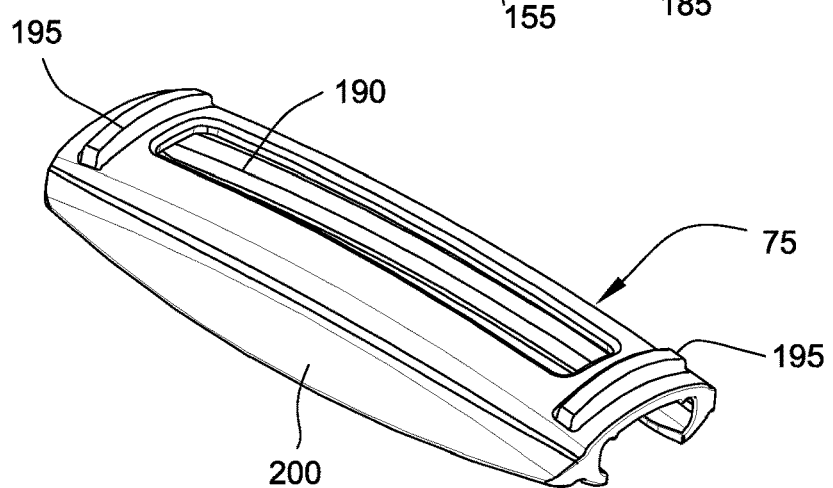
FIG. 21 is a perspective view of a clip according to an embodiment of the present invention.
Figure 22:
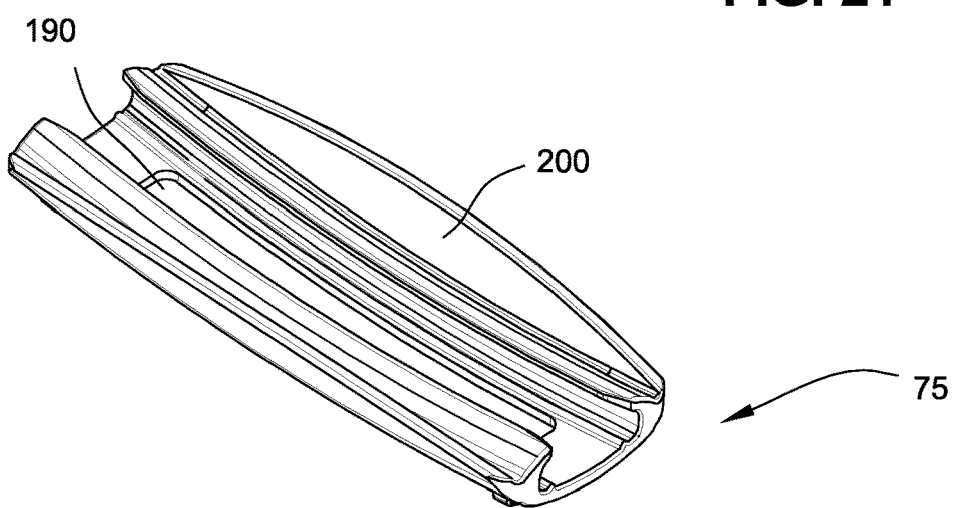
FIG. 22 is a reverse perspective view thereof.
Figure 23:
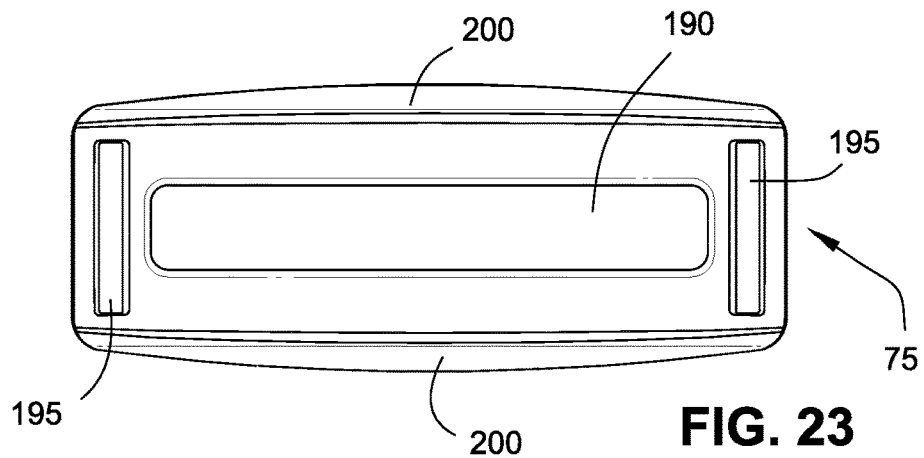
FIG. 23 is a front view thereof.
Figure 24:
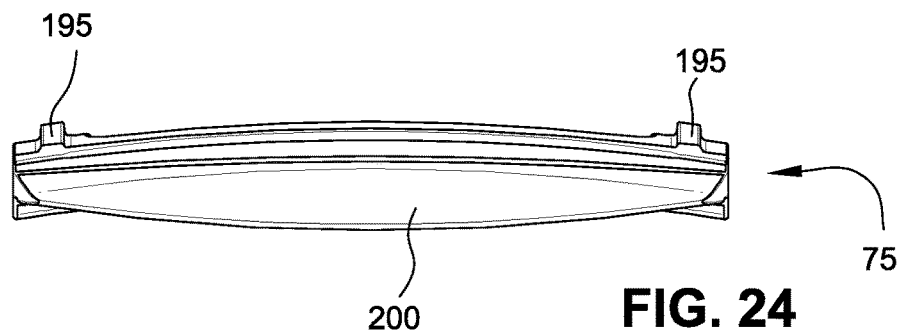
FIG. 24 is a bottom view thereof.
Figure 25:
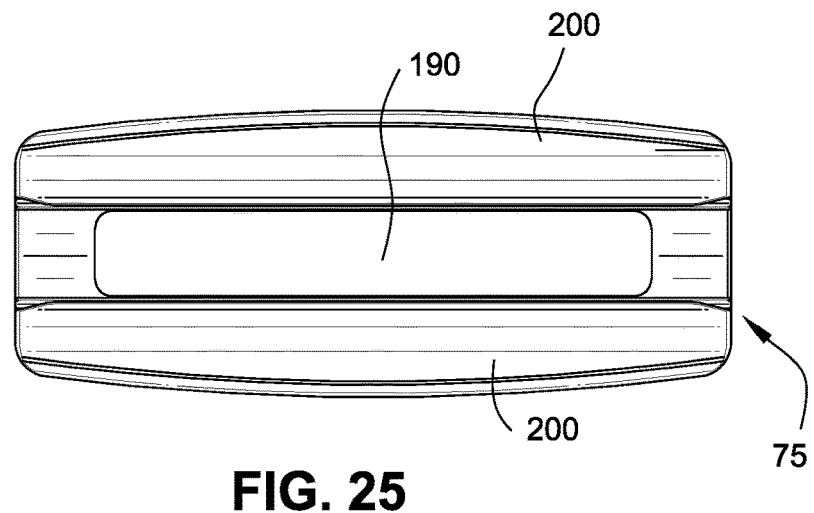
FIG. 25 is a rear view thereof.
Figure 26:
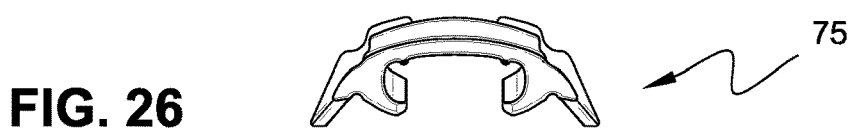
FIG. 26 is a side view thereof.
Figure 27:
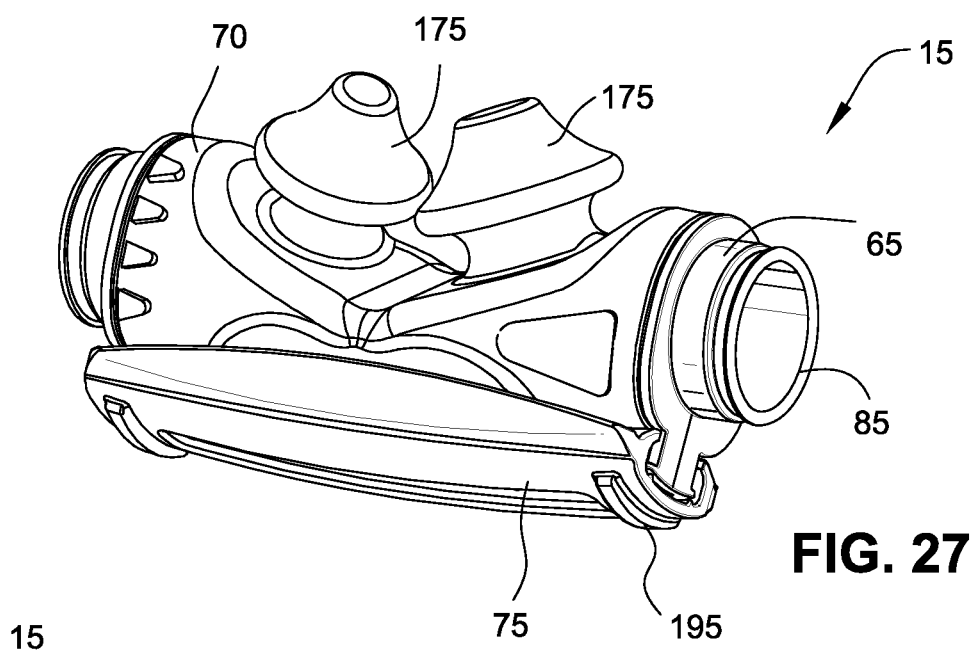
FIG. 27 is a perspective view of a cushion subassembly according to an embodiment of the present invention.
Figure 28:
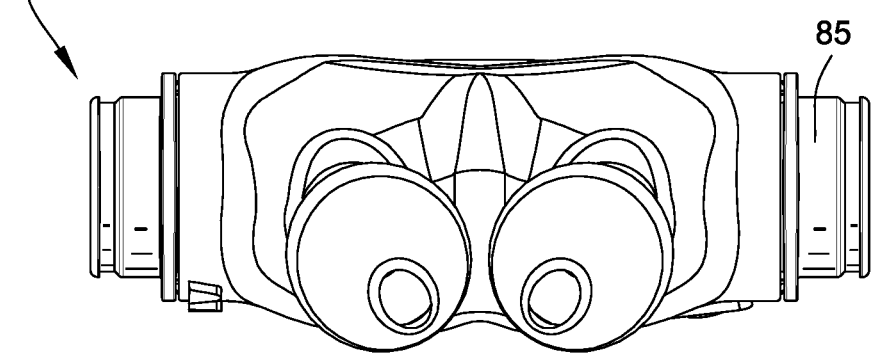
FIG. 28 is a top view thereof.
Figure 29:
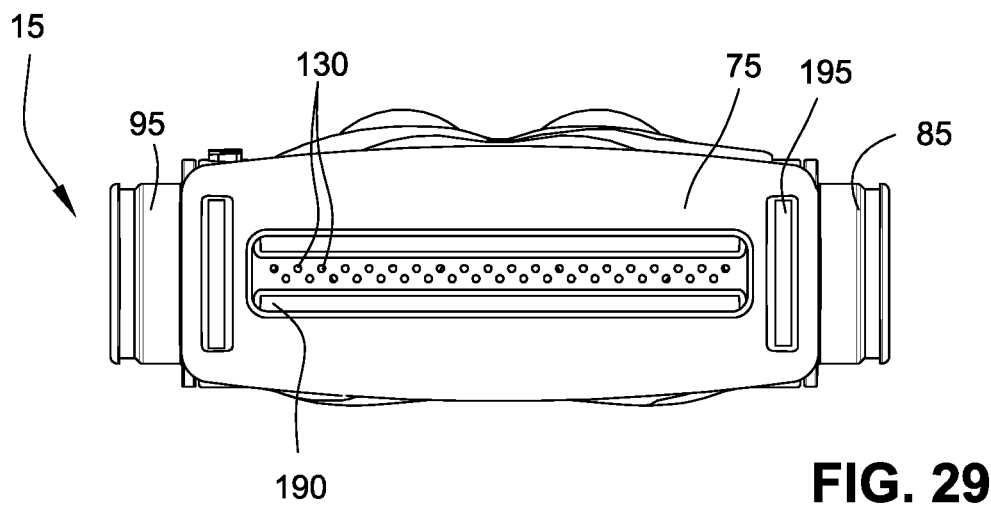
FIG. 29 is a bottom view thereof.
Figure 30:
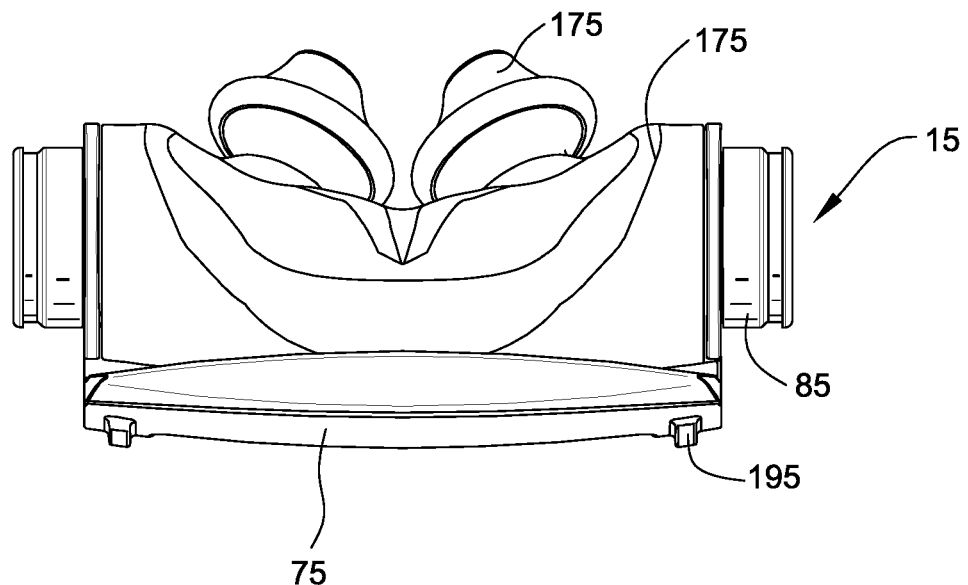
FIG. 30 is a rear view thereof.
Figure 31:
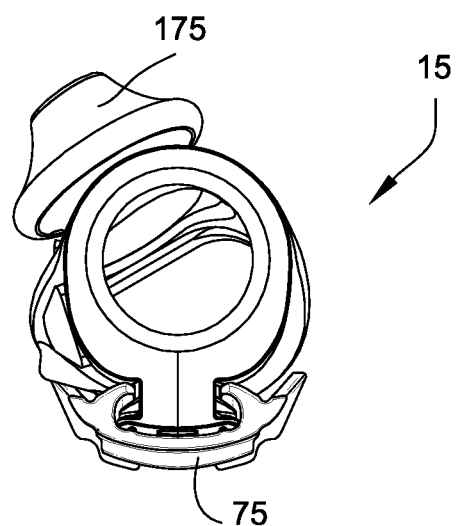
FIG. 31 is a side view thereof.
Figure 32:
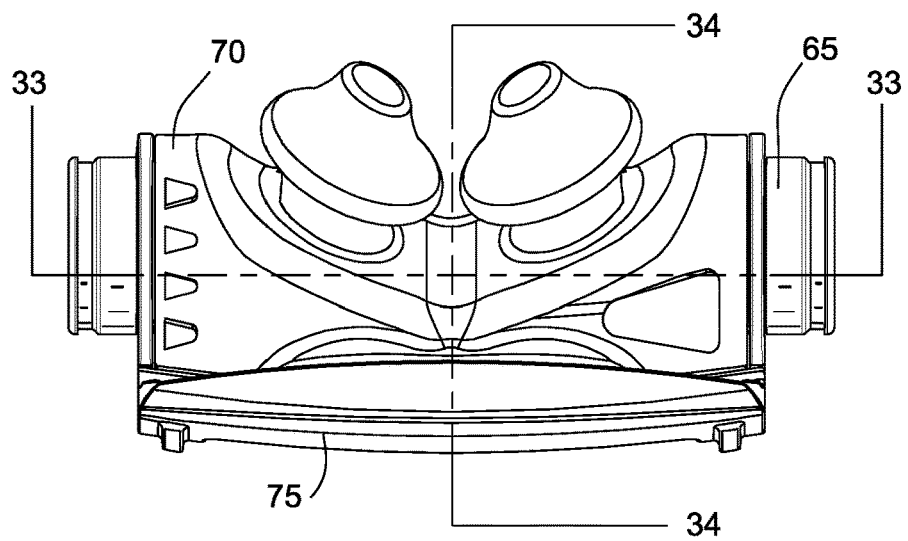
FIG. 32 is a front view thereof.
Figure 33:
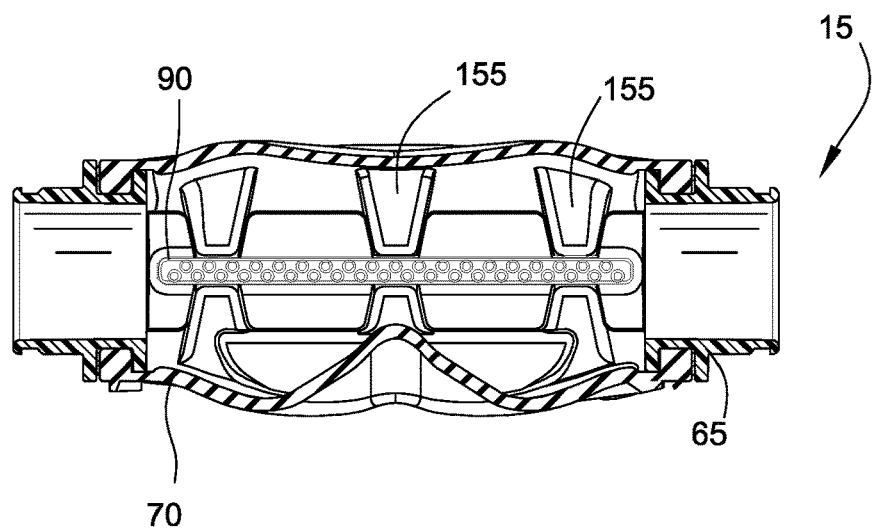
FIG. 33 is a cross-sectional view along line 33-33 of FIG. 32.
Figure 34:
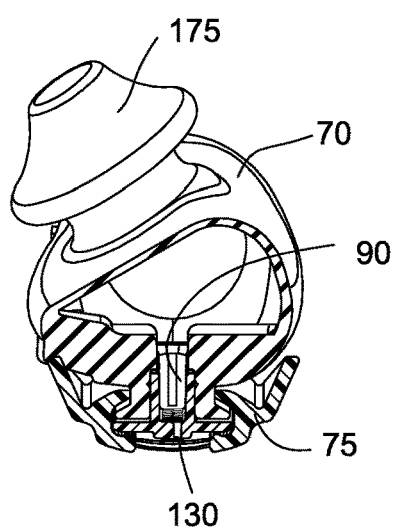
FIG. 34 is a cross-sectional view along line 34-34 of FIG. 32.

As best shown in FIGS. 17 and 20, cushion includes one or more lugs 155 that are fitted snugly relative to cut 150 outs in frame 65. The provision of the matching lugs and cut outs helps prevent the assembly of cushion 70 (that has no vent holes) to a frame (not shown) without a vent. Thus, the situation is avoided where the user inadvertently attempts to couple a ventless frame with a ventless cushion.

2.2.2 No Vent Holes

Cushion 70 has no vent holes, since the vent holes are provided in the frame 65. However, the wall thickness of a portion 180 (FIG. 19) of the cushion remains thickened to support nozzle members 175.

2.2.3 Corner Lugs

As shown in FIG. 20, cushion 70 includes corner lugs 185 to interface with cored portions 160 of frame 15.

2.3.0 Clip

Clip 75 includes a main body having lateral ends, either one of which can be assembled to the cushion/frame subassembly, by sliding action to secure same.

2.3.1 Vent Window

Clip 75 includes a vent window 190 that aligns with the vent holes in vent channel upon assembly of the clip to the cushion/frame subassembly.

2.3.2 Ribs

Clip 75 includes ribs 195 provided on each lateral side thereof. Ribs 195 help with strength and stiffness, as well as provide a grip surface.

2.3.3 Wings

Clip 75 includes wings 200 on each side of the main body. Wings 200 preferably have a compound curved shape, to improve strength and stiffness.

3.0 Alternative Mask Arrangements

Vent configurations, such as those described above, may be incorporated into other mask arrangements. For example, FIGS. 38-44 illustrate an embodiment of a frame 550 for a full-face (nasal-oro) mask. As illustrated, the frame 550 includes an upper support member 560 adapted to support a forehead support, lower headgear clip receptacles 570 adapted to be engaged with clips provided to straps of a headgear assembly, and a lower bore 580 adapted to engage an inlet conduit, e.g., elbow. Also, the perimeter of the frame includes a plurality of slots 590 therethrough, e.g., three slots. The slots 590 are adapted to engage a cushion clip that retains a cushion on the frame 550. Such a frame arrangement is disclosed in PCT Application Nos. PCT/AU2006/000035 and PCT/AU2006/000037, each incorporated herein by reference in its entirety.

As best shown in FIGS. 38, 40, 41, and 44, the upper portion of the frame 550 includes a vent assembly 500 similar to that shown in FIG. 35. The vent assembly 500 is positioned on the frame 550 below spaced-apart side walls 565 of the upper support member 560. The vent assembly 500 includes a plurality of holes 505 arranged in a three column pattern. As illustrated, the columns are aligned or parallel to the longitudinal axis L of the frame, e.g., the center column is aligned with the longitudinal axis and the outside columns are parallel to the longitudinal axis (see FIG. 41). The center column 510 includes 10-20 holes, e.g., 15 holes, and each outside column 515 includes 8-15 holes, e.g., 12 holes. The holes 505 in the outside columns 515 are aligned with the holes 505 in the center column 510, with the center column 510 having one additional hole at the upper end and two additional holes at the lower end. In the illustrated embodiment, each hole 505 has a generally part conic shape, including opposed walls that converge from a larger (inside) diameter (e.g., about 1.28 mm) to a smaller (outside) diameter (e.g., about 0.7 mm), as viewed in the direction of exhausted gas. The included angle of the cone may be about 14°, the height of the cone may be about 2.38 mm, and a radius provided on the inside diameter may be about 0.75 mm. However, the frame 550 may include other vent arrangements, e.g., the vent arrangement shown in FIGS. 36-37. In this arrangement, the first and second center columns may be parallel to and offset from the longitudinal axis of the frame.

FIGS. 45-52 illustrate a vent configuration incorporated into a frame 650 for a nasal and mouth mask. As illustrated, the frame 650 includes a main body 660 having a side frame portion 670 on each lateral side thereof. The main body 660 includes an aperture 662 and a flanged collar member 664 adapted to engage an elbow. Also, the frame 650 includes a channel 680 for retaining a mouth cushion which supports nasal prongs. In addition, each side frame portion 670 includes headgear attachment points, e.g., upper and lower anchors 672, 674, for attaching a headgear assembly. Such a frame arrangement is disclosed in U.S. Provisional Application No. 60/795,562, entitled "Mask System" and filed Apr. 28, 2006, the entirety incorporated herein by reference.

Figure 48:
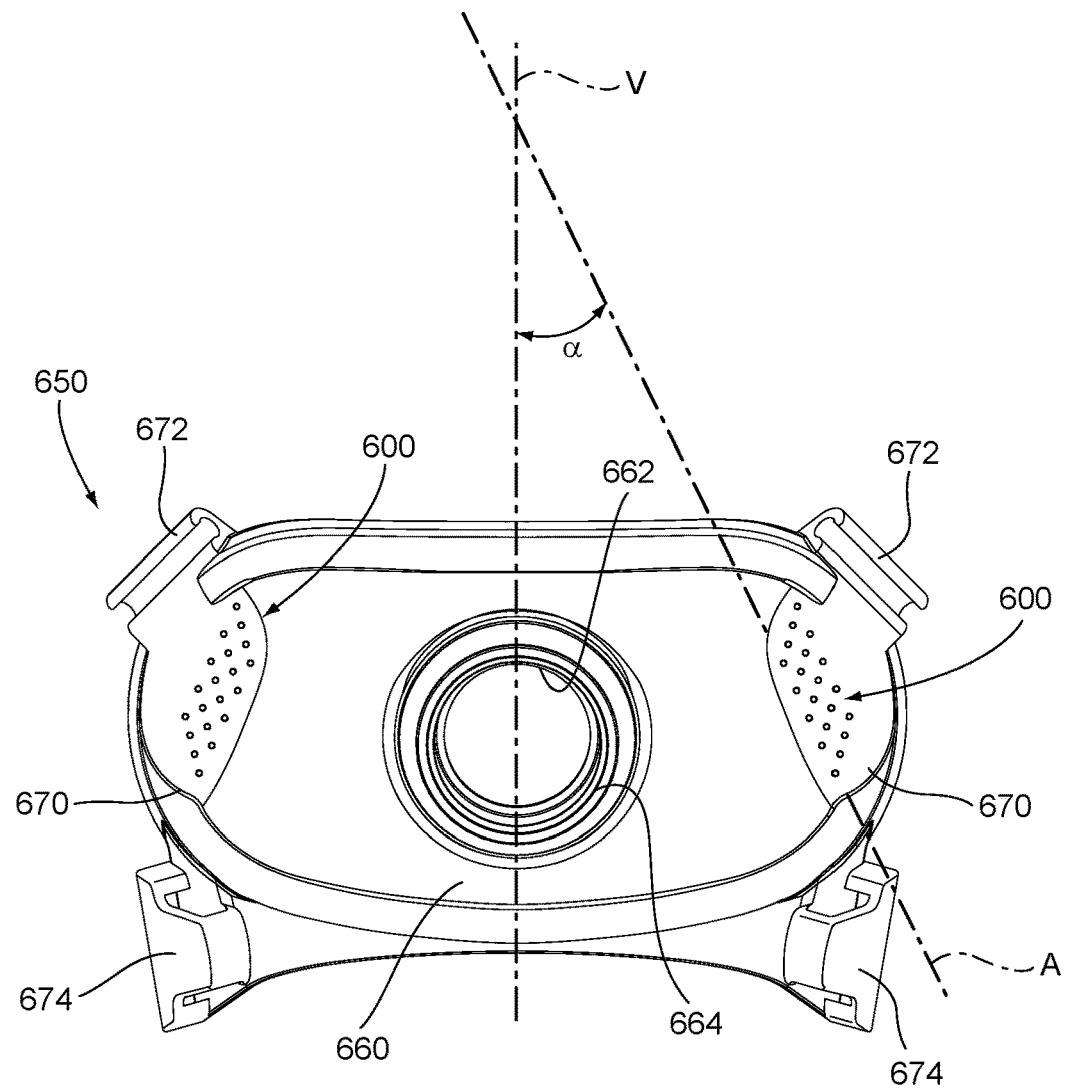
Figure 49:
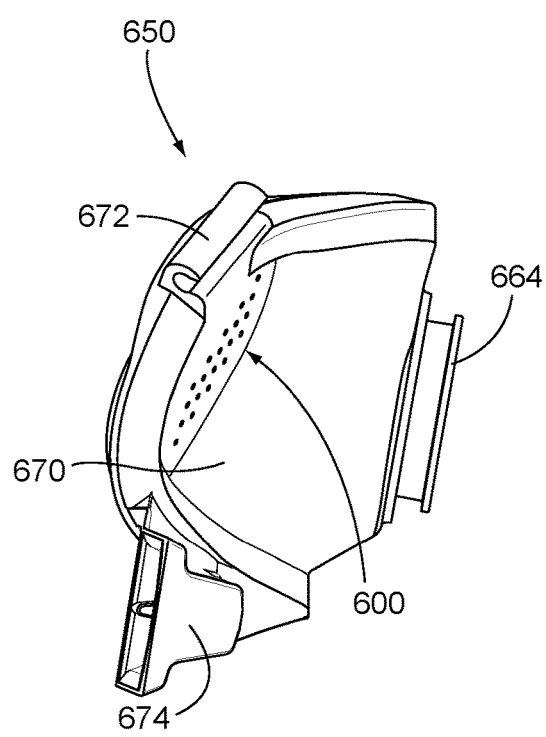
Figure 50:
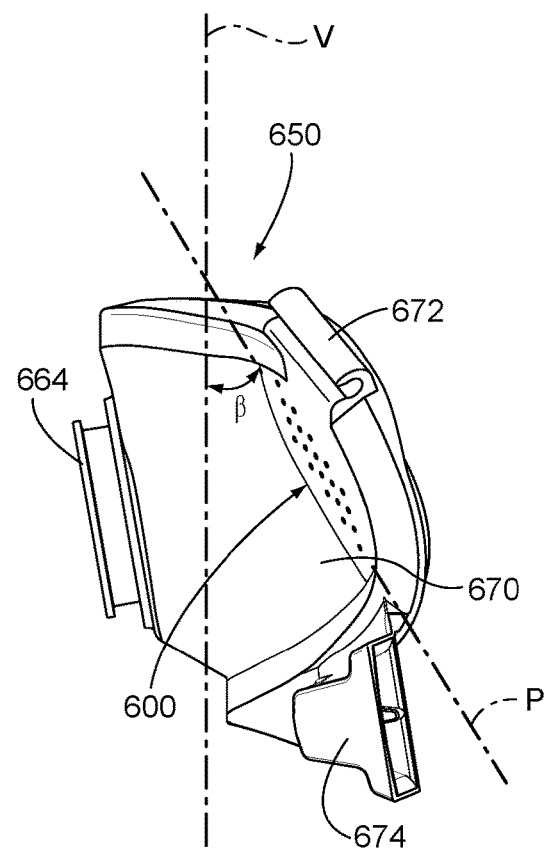
Figure 51:
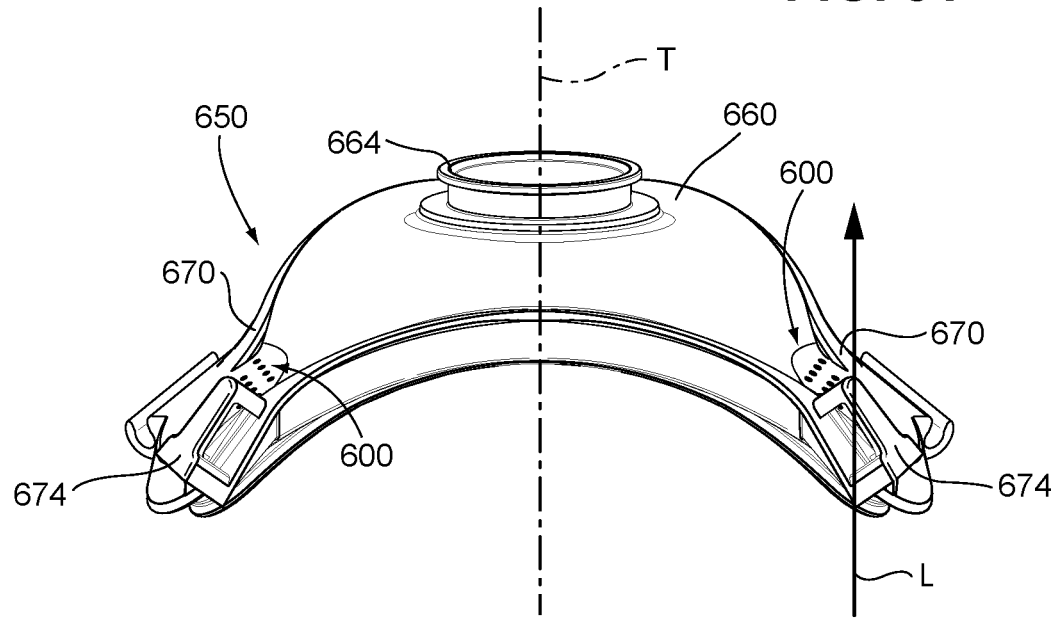
Figure 52:
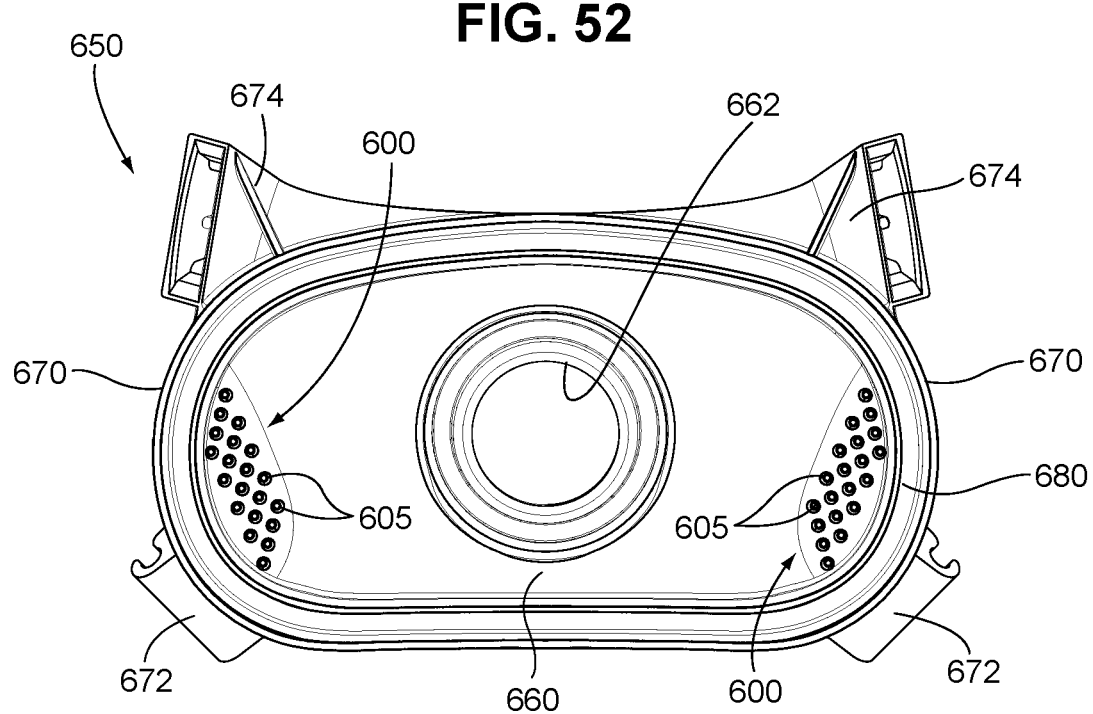

In the illustrated embodiment, a vent assembly 600 is provided in each side frame portion 670 of the frame 650, adjacent the upper anchors 672. Each vent assembly 600 includes an array or pattern of relatively small holes 605 arranged in a plurality of columns, e.g., 3-10 columns, and in the example illustrated, 5 columns. The 5 columns are vertically staggered with respect to one another. Also, the first hole in each column cooperate to form an axis A that is angled at an angle α (when viewed from the front as shown in FIG. 48) of about 15-35°, e.g., 25°, with respect to vertical axis V. As best shown in the side view of FIG. 50, each hole is provided along a plane P (approximate plane shown in FIG. 50 due to frame angle in side view) that forms an angle θ of about 20-40°, e.g., 30°, with respect to vertical axis V. As shown in the bottom view of FIG. 51, each hole has a longitudinal axis L that is angled at an angle of about −10° to about 45°, e.g., 0°, with respect to transverse axis T. Each column includes 2-6 holes, e.g., 4 holes. In the illustrated embodiment, each hole 605 has a generally part conic shape, including opposed walls that converge from a larger diameter to a smaller diameter, as viewed in the direction of exhausted gas. The smaller diameter may be about 0.7 mm, the larger diameter may be about 1 mm, the included angle of the cone may be about 10°, and the height of the cone may be about 1.7 mm. However, other vent arrangements are possible.

As illustrated, the holes 605 are located away from the elbow aperture 662 to avoid air flow interference. Also, the holes 605 are located near headgear attachment points 672 where the frame 650 is relatively flat to the users face for the anchor structures. In addition, the holes 605 are positioned on relatively flat portions of the frame 650 so that air may be vented perpendicularly from the general plane of the patient's face to avoid air jetting towards a bed partner. Thus, this vent arrangement optimizes mask operation and is synergistic in that it utilizes an area of the frame 650 which is relatively flat to the patient's face for two purposes, i.e., anchor structure and perpendicular venting. Aesthetics of the frame 650 are also improved significantly by reducing the number of relatively flat areas that are provided on the frame 650.

4.0 Alternative Embodiment of Cushion Assembly

Figure 53:
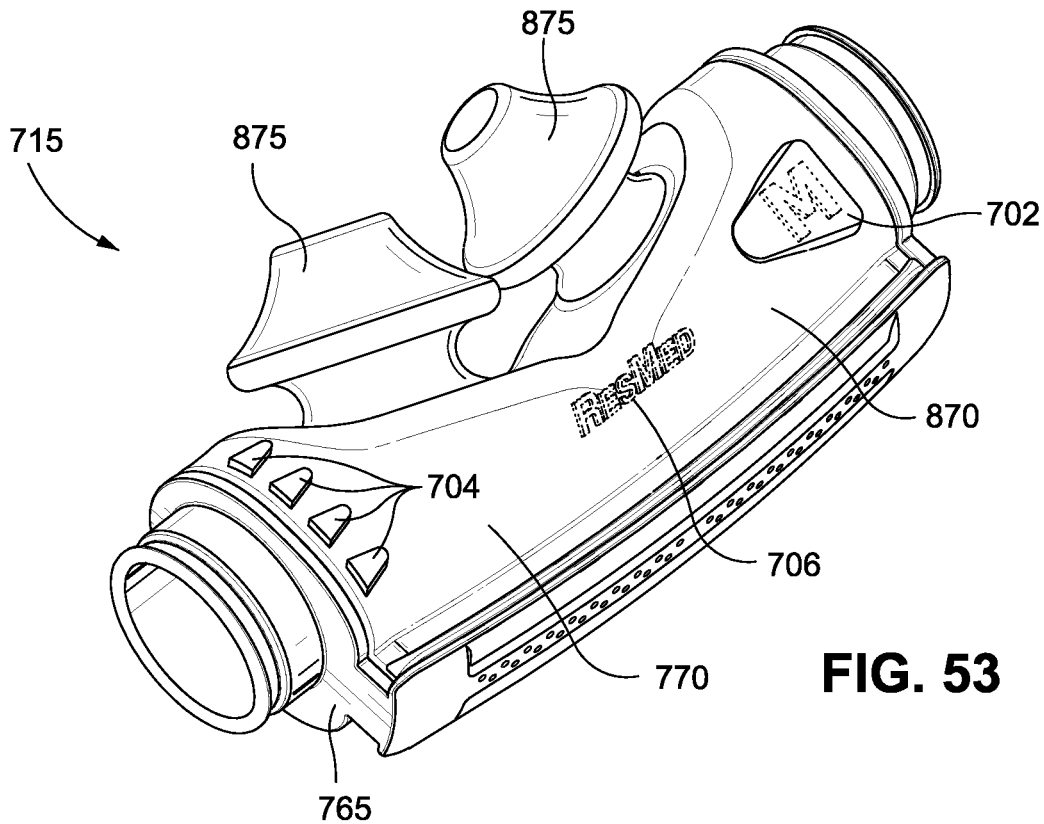
FIGS. 53-55 are various views of a cushion assembly according to another embodiment of the present invention.
Figure 54:
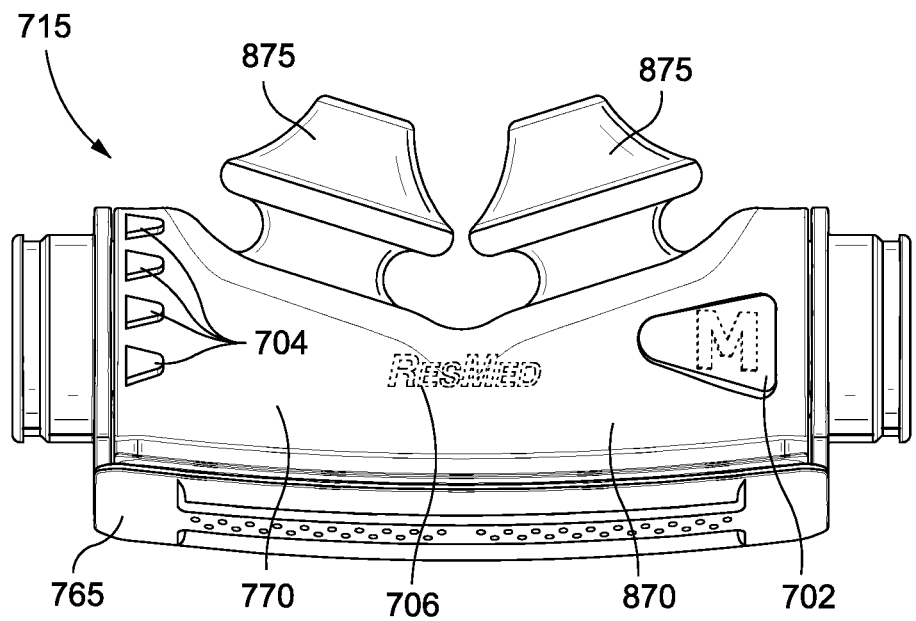
Figure 55:
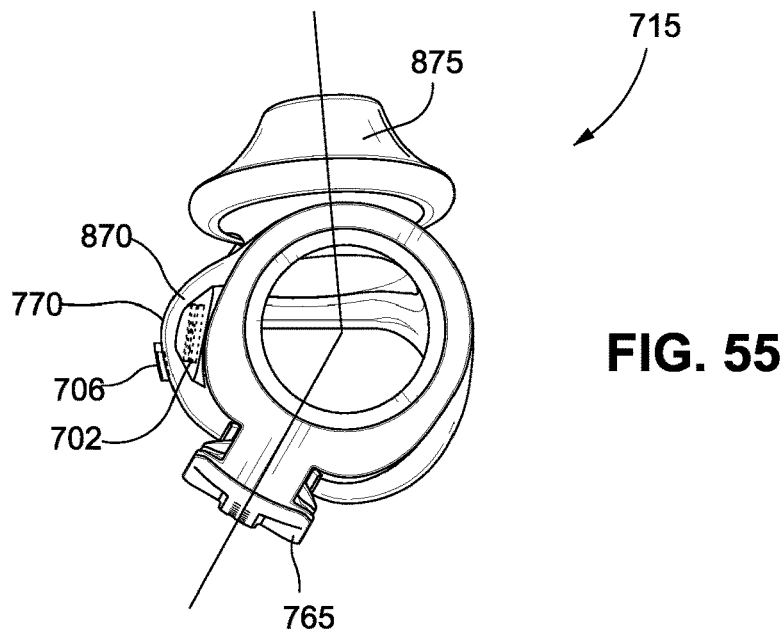
Figure 63:
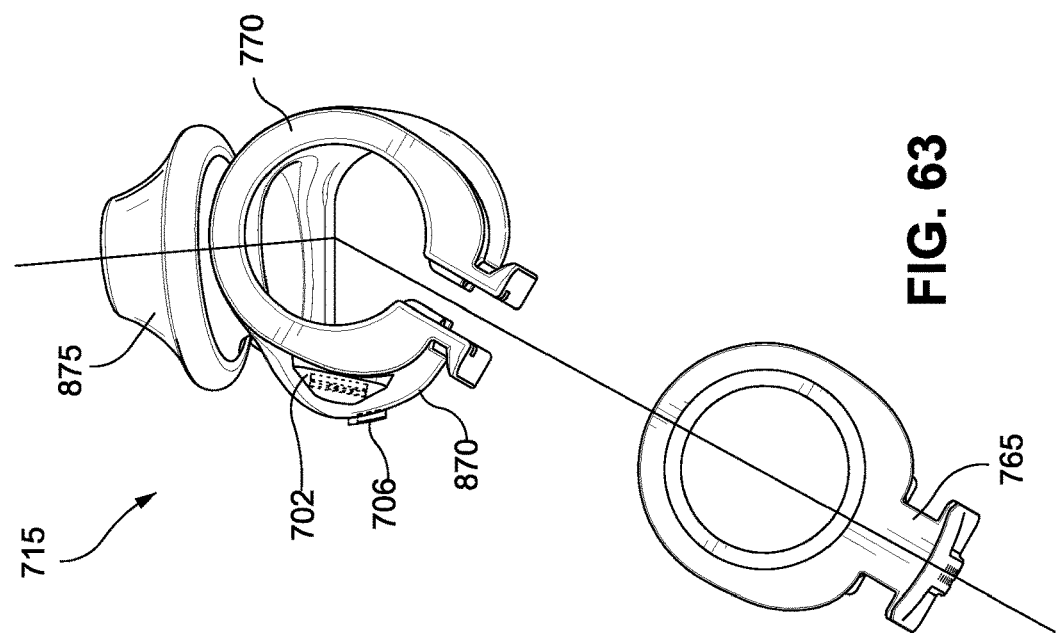
FIGS. 62-64 are various exploded views of the cushion assembly shown in FIGS. 53-55.
Figure 64:
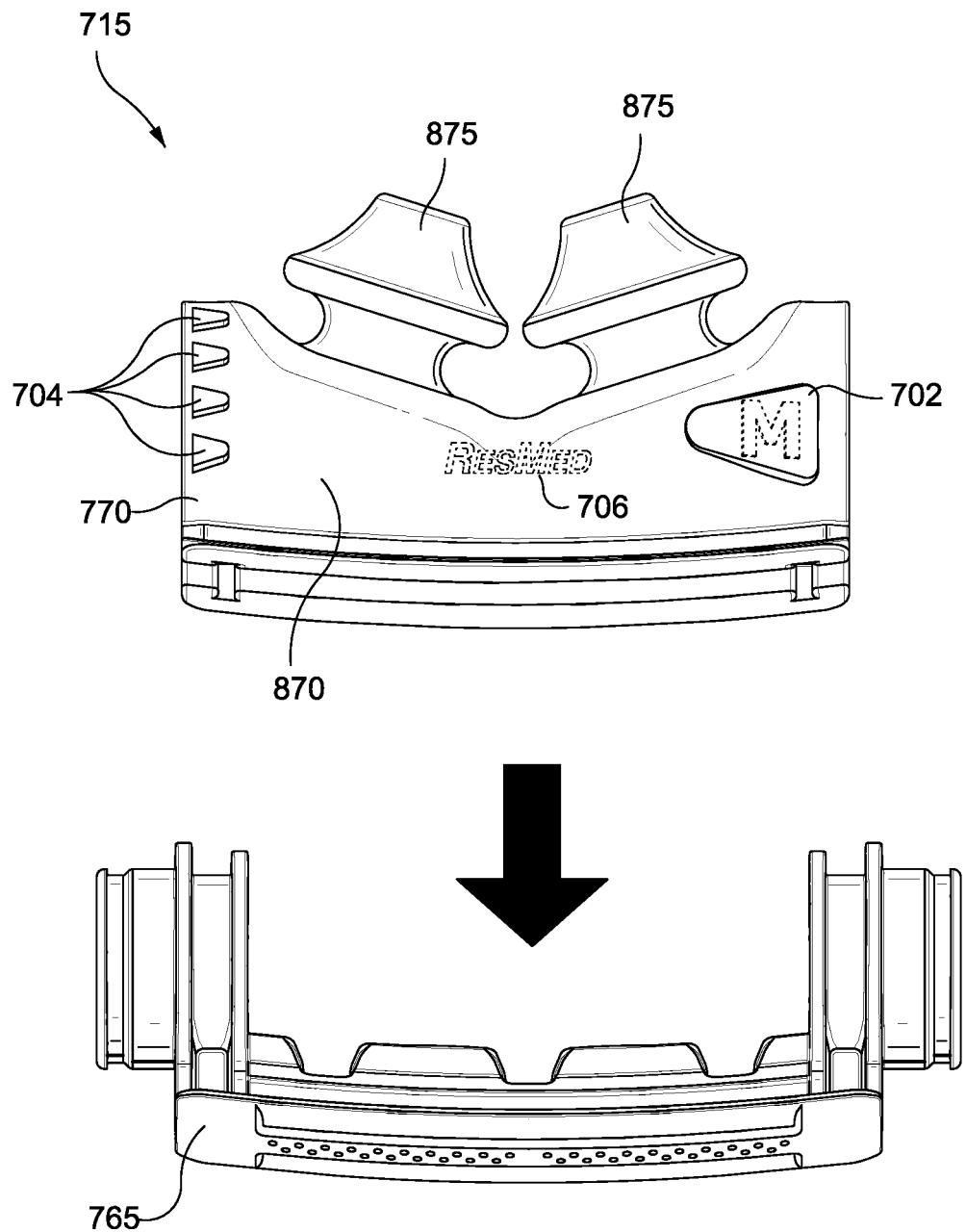
Figure 65:
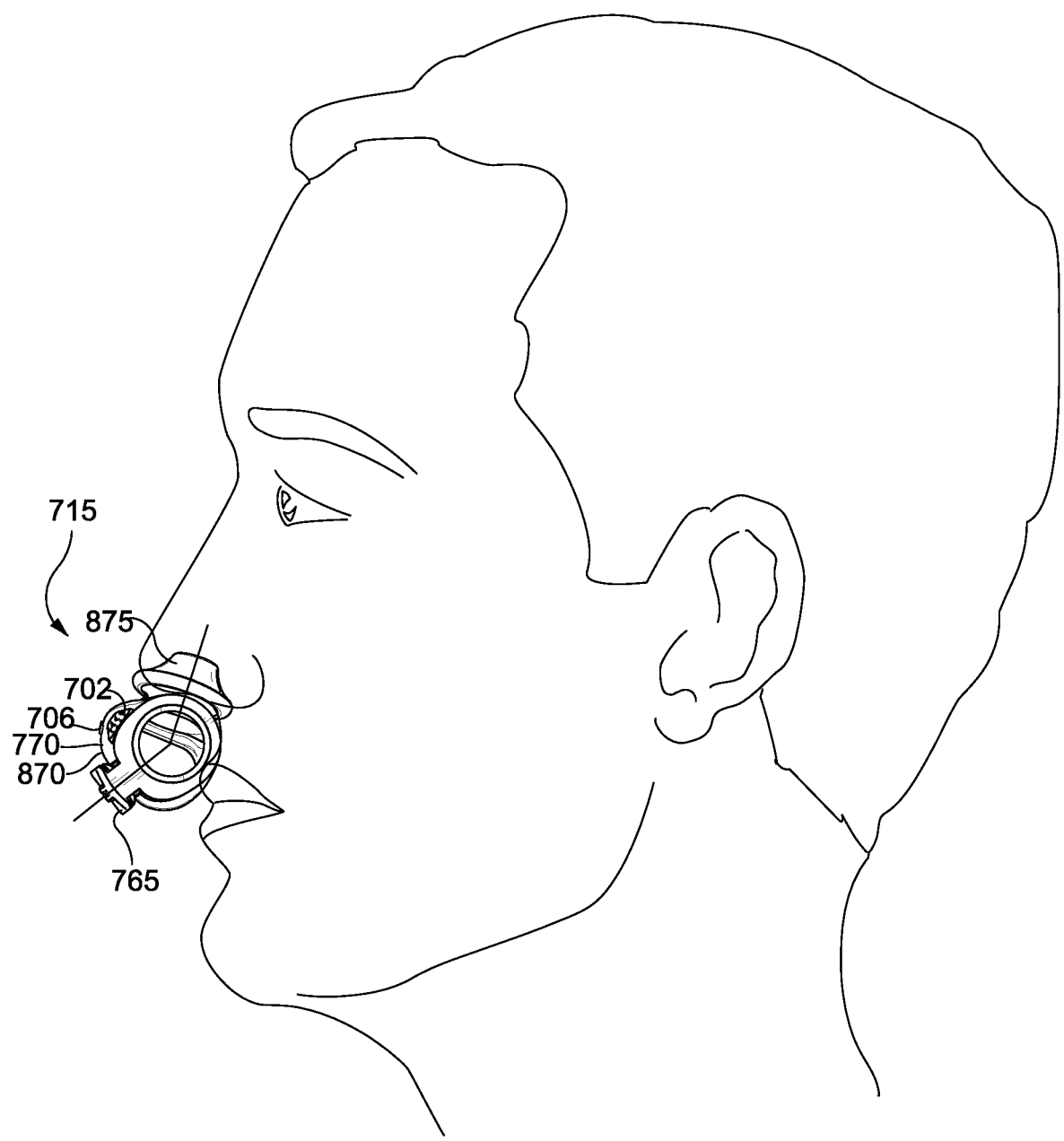
FIG. 65 is a side view illustrating correct orientation of the cushion assembly shown in FIGS. 53-55 on a patient.
Figure 66:
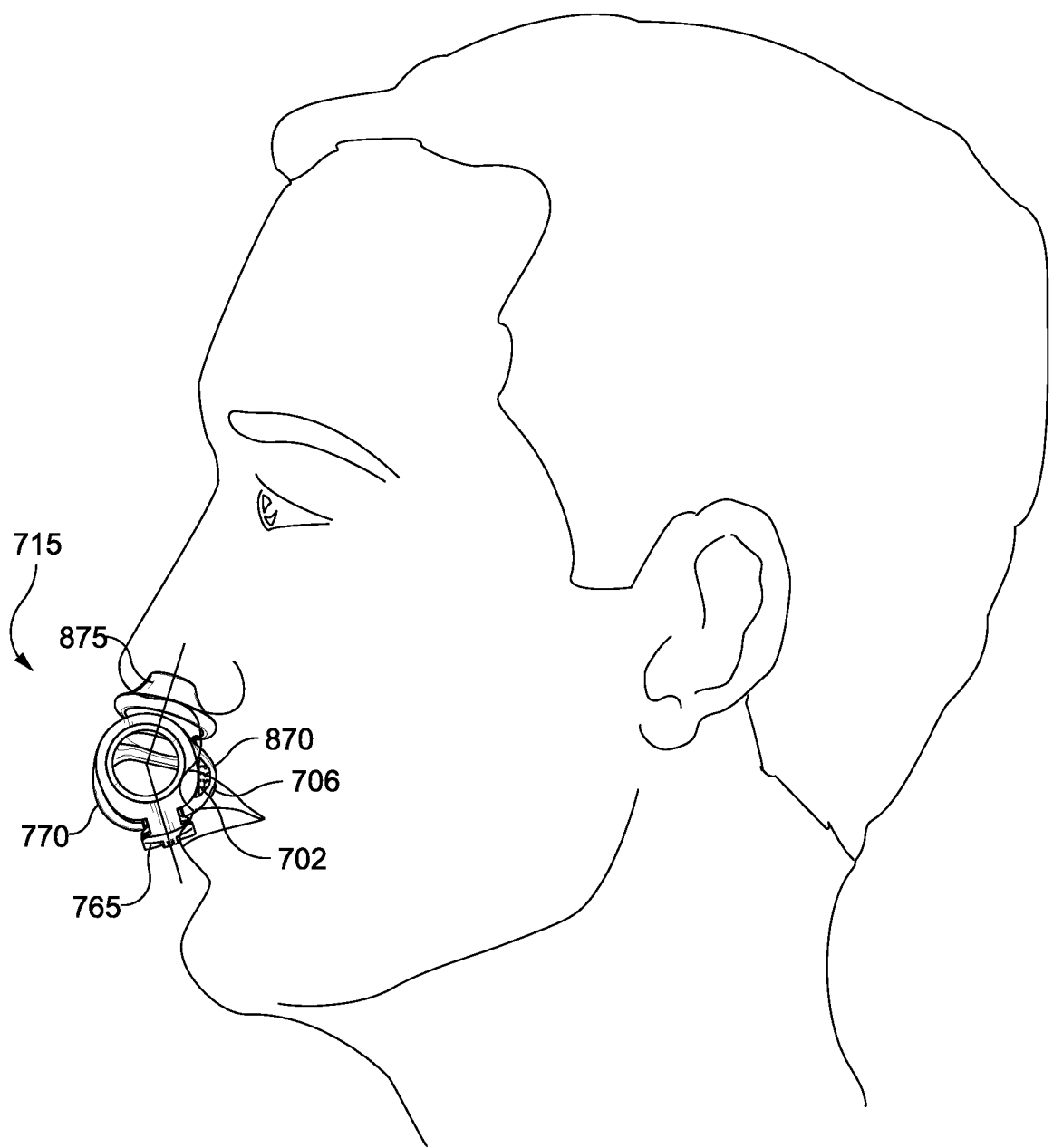
FIG. 66 is a side view illustrating incorrect orientation of the cushion assembly shown in FIGS. 53-55 on a patient.

FIGS. 53-66 illustrate a cushion assembly 715 according to another embodiment of the present invention. As illustrated, the cushion assembly 715 includes a frame 765 and a cushion 770 provided to the frame 765. Although not illustrated, it should be understood that a clip, e.g., clip 75 described above, may be provided to secure the cushion 770 to the frame 765. FIGS. 53-55 show assembled views of the cushion 770 and frame 765, FIGS. 56A-61 show the frame 765 in isolation, FIGS. 62-64 show the assembly of the frame 765 and the cushion 770, and FIGS. 65-66 illustrate orientation of the cushion assembly 715.

4.1.0 Frame

As best shown in FIGS. 56A-61, the frame 765 has a main body 780 and lateral sides. Each lateral side includes a lateral connector portion 785. The frame 765 is preferably made of molded plastic, e.g., polycarbonate and/or polypropylene.

4.1.1 Vent Channel

The main body 780 of the frame 765 is provided with a vent channel 790 defined by a base wall 792 and a pair of side walls 794. The vent channel 790 extends from an inside surface 795 of the main body toward the base wall 792.

4.1.2 Vent Holes

Figure 57:
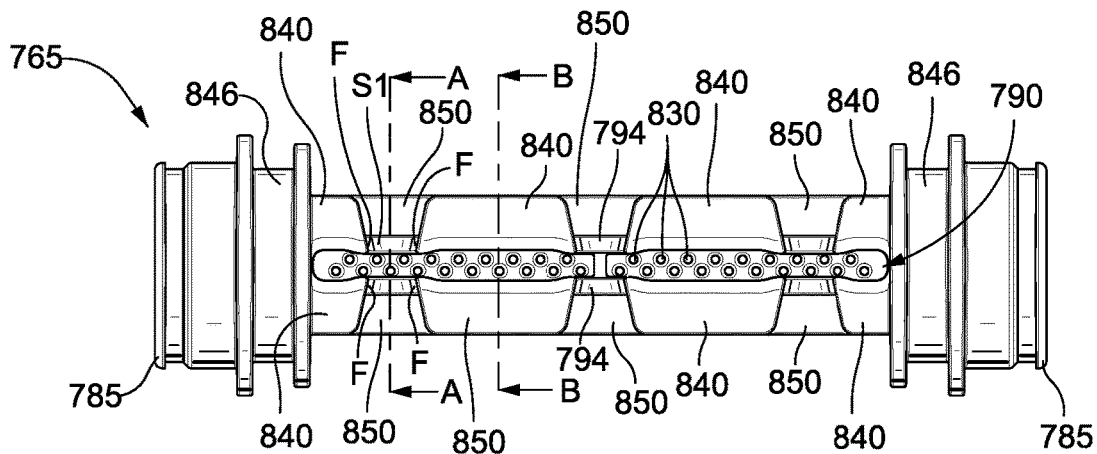

The channel 790 is in communication with a plurality of vent holes 830, e.g., 6-60 vent holes, and preferably about 35-45 vent holes, although there could be more than 60 holes or less than 6 holes, depending on application. In the example of FIG. 57, there are 38 holes. Each vent hole 830 may have a similar conic shape such as vent hole 130 described above. In addition, the vent arrangement includes offset rows of vent holes. However, other arrangements are possible.

4.1.3 Cushion Channels and Cut Outs

The frame 765 includes lugs 840 to help form a longitudinal cushion channel 845 into which an edge portion 771 of the cushion 770 is fitted, to secure the cushion 770 relative to the frame 765 to form a frame/cushion subassembly prior to attachment of the clip. The cushion channel 845 is provided on each side of the vent channel 790 and includes one or more cut outs 850 to receive corresponding lugs of the cushion 770 (as described above with respect to cushion 70 and frame 65). Frame 765 also includes circumferential channels 846 to receive end portions of the cushion 770.

4.1.4 Thickened Side Wall

In the illustrated embodiment, the side walls 794 of the frame 765 are locally thickened at the cut outs 850. Specifically, the wall sections 51 at the cut outs 850 (i.e., between lugs 840) are thickened with respect to the adjacent wall sections S2 supporting lugs 840. This arrangement increases the strength of the side wall 794 to reduce bending stress, which results in an increase in strength of the overall frame 765.

Figure 58:
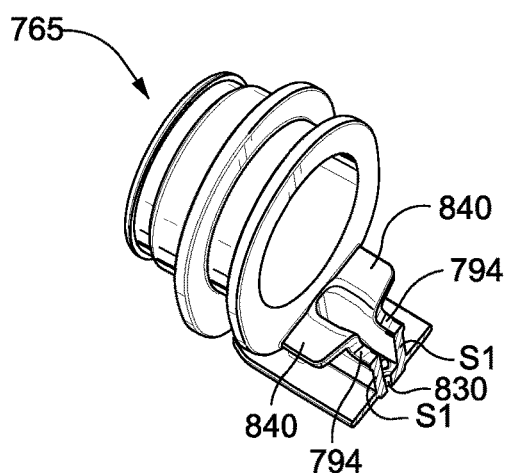
FIGS. 58-59 are cross-sectional views through line A-A of FIG. 57.
Figure 59:
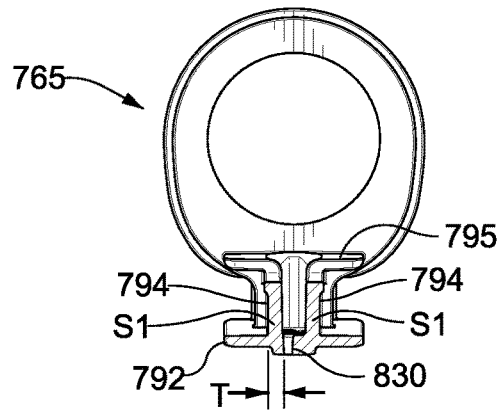
Figure 60:
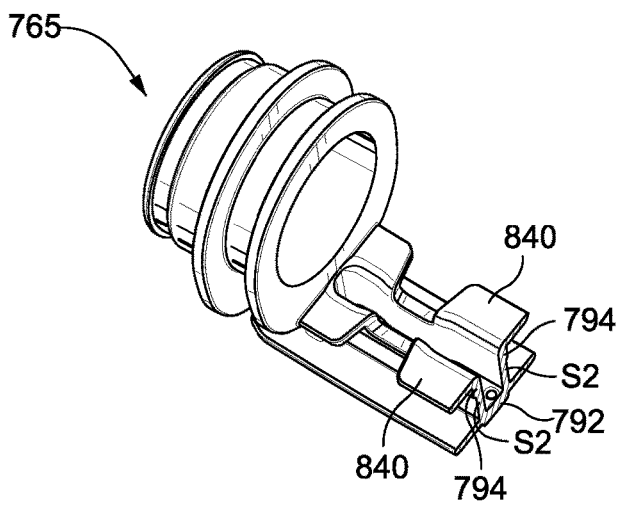
FIGS. 60-61 are cross-sectional views through line B-B of FIG. 57.
Figure 61:
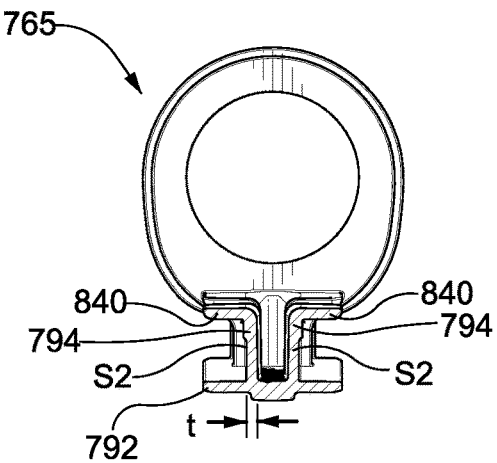
Figure 62:
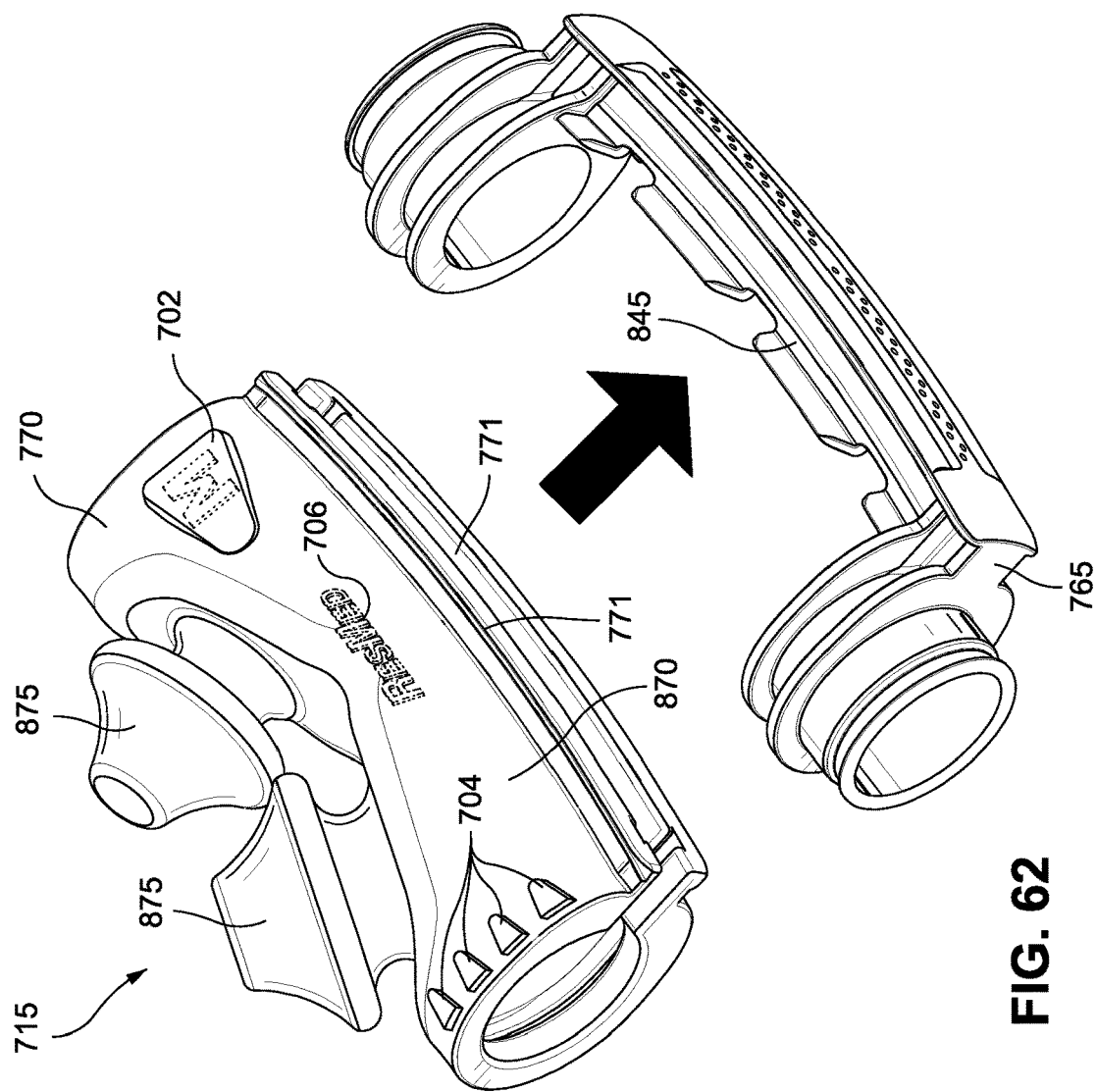

For example, the wall section 51 between lugs 840 shown in FIGS. 58-59 is thicker than the wall section S2 supporting lugs 840 shown in FIGS. 60-61. In an embodiment, the wall section 51 may have a thickness T of about 1.20 mm and the wall section S2 may have a thickness t of about 1.0 mm. However, other thicknesses are possible depending on application. In previous designs, the side walls 794 had a substantially constant wall thickness along its length.

4.1.5 Fillet Size Increase

Figure 56A:
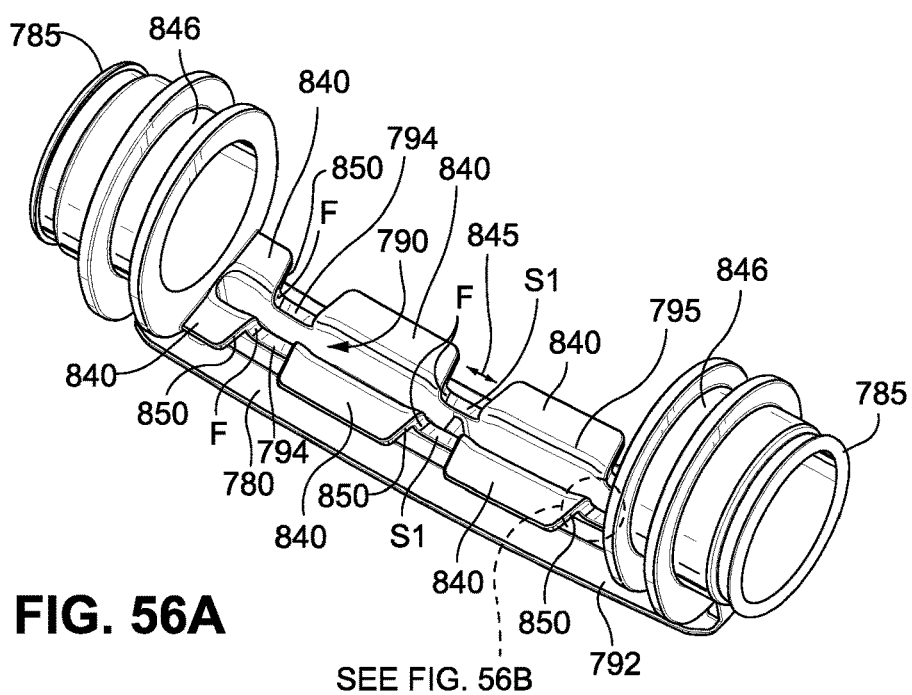
FIGS. 56A, 56B and 57 are various views of a frame of the cushion assembly shown in FIGS. 53-55.
Figure 56B:
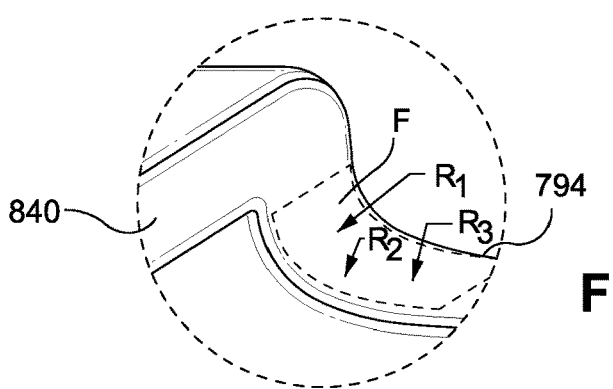

As shown in FIGS. 56A, 56B, and 57, the size of the fillets F between the side walls 794 and the lugs 840 has been increased relative to previous designs. In an embodiment of the fillet F, as shown in FIG. 56B, the radius $R_1$ may be in the range of 0.1-0.95 mm, e.g., preferably 0.6 mm, the radius $R_2$ may be in the range of 0.1-0.95 mm, e.g., preferably 0.5 mm, and the radius $R_3$ may be in the range of 0.1-1.2 mm, e.g., preferably 1.2 mm. Although specific dimensions and ranges of the fillet F are indicated, it is to be understood that these dimensions and ranges are merely exemplary and other dimensions and ranges are possible depending on application. For example, the exemplary dimensions may vary by 10-20% or more or less depending on application.

The fillet size increase provides better stress distribution at the junction between the side walls 794 and the lugs 840. Thus, the fillet size increase (along with the thickened side walls described above) results in overall strength improvement of the frame 765.

4.2.0 Cushion

The cushion 770 is substantially similar to the cushion 70 described above. As illustrated, the cushion 770 includes a main body 870 supporting a pair of nozzle members 875 that are designed to engage with a user's nares in use.

4.2.1 Logo/Indicators

The main body 870 of the cushion 770 includes a size indicator 702, e.g., medium (M) size, and a series of position arrows 704 to facilitate positioning between the headgear and the cushion assembly 715. In addition, the cushion 770 includes text and/or a logo 706, e.g., ResMed logo. As illustrated, the logo 706, the size indicator 702, and the position arrows 704 protrude from the main body 870, e.g., raised configuration, to facilitate recognition.

In the illustrated embodiment, the logo 706, the size indicator 702, and the position arrows 704 are provided on one side of the main body 870. This labeling arrangement provides a visual cue to assist the patient in achieving correct alignment and orientation of the cushion 770 and frame 765 with respect to the patient.

Specifically, the labeling arrangement prevents incorrect assembly of the cushion assembly 715 (i.e., cushion 770 and frame 765) onto the headgear. As shown in FIG. 65, when the cushion assembly 715 is correctly oriented on the headgear (and hence correctly oriented with respect to the patient in use), the logo 706, size indicator 702, and position arrows (not visible in FIG. 65) face outwards or away from the patient in use. However, as shown in FIG. 66, when the cushion assembly 715 is incorrectly oriented on the headgear (and hence incorrectly oriented with respect to the patient in use), the logo 706, size indicator 702, and position arrows (not visible in FIG. 66) face inwards or towards the patient. Thus, the patient may easily determine if the cushion assembly 715 is correctly oriented.

Often, the frame 765 remains attached to the headgear and the cushion 770 is removed from the frame/headgear subassembly, e.g., for cleaning. When the cushion 770 is re-assembled to the frame 765 (e.g., see FIGS. 62-64), the logo 706, size indicator 702, and position arrows 704 may be used as a visual cue to assist the patient in achieving correct alignment and orientation of the cushion 770 onto the frame 765.

In an embodiment, the logo 706, the size indicator 702, and/or the position arrows 704 may be provided to facilitate orientation.

5.0 Alternative Embodiment of Nasal Assembly

Figure 67:
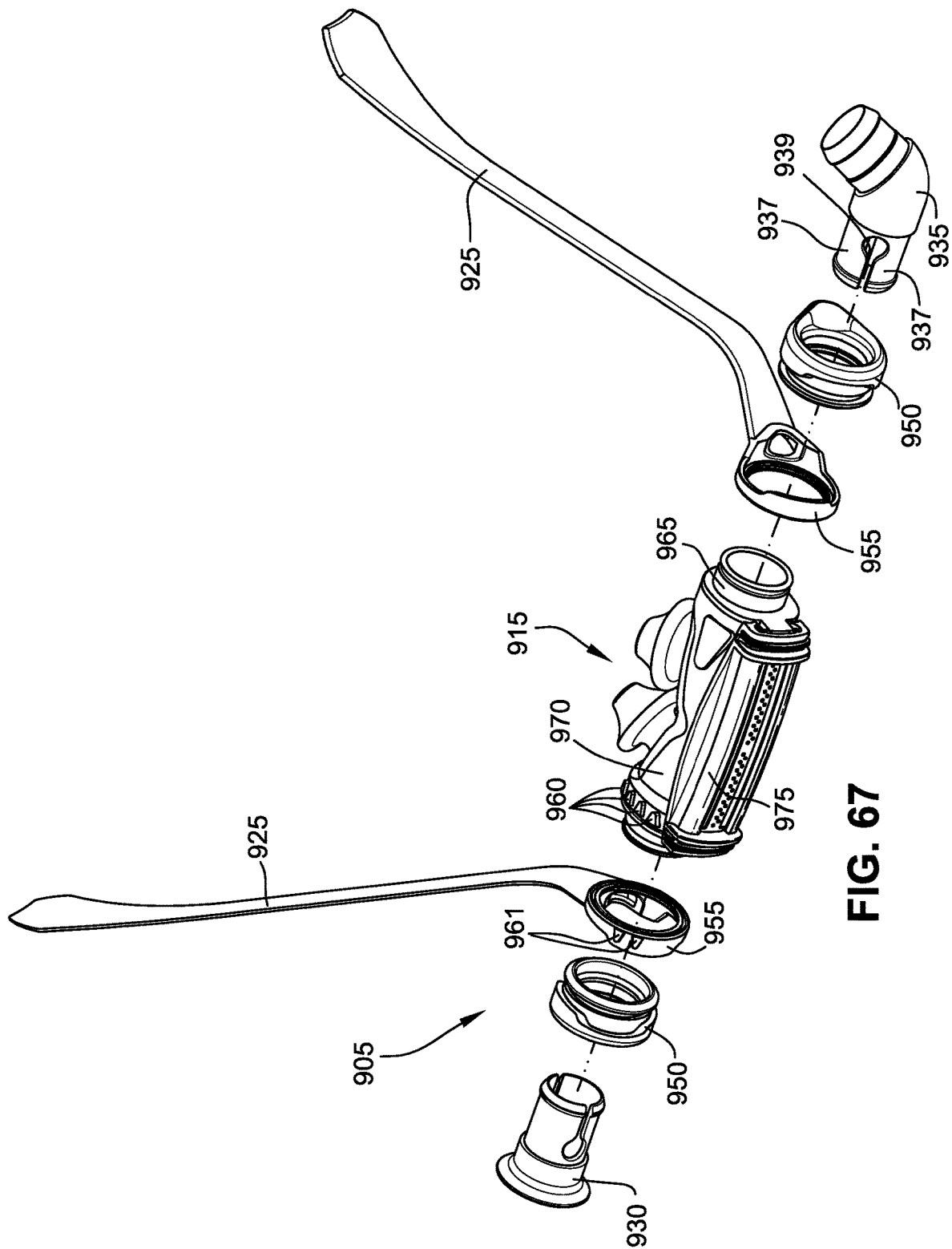
FIG. 67 is an exploded view of a nasal assembly according to another embodiment of the present invention.
Figure 68:
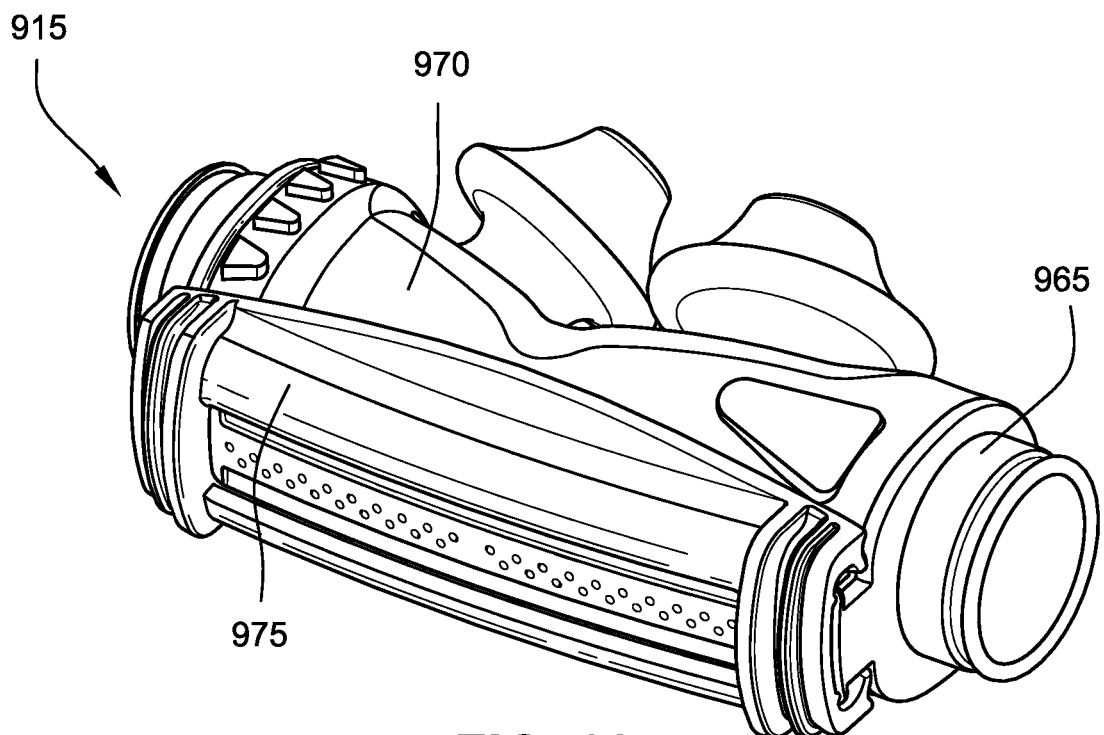
FIGS. 68-75 are various views of a cushion assembly of the nasal assembly shown in FIG. 67.
Figure 69:
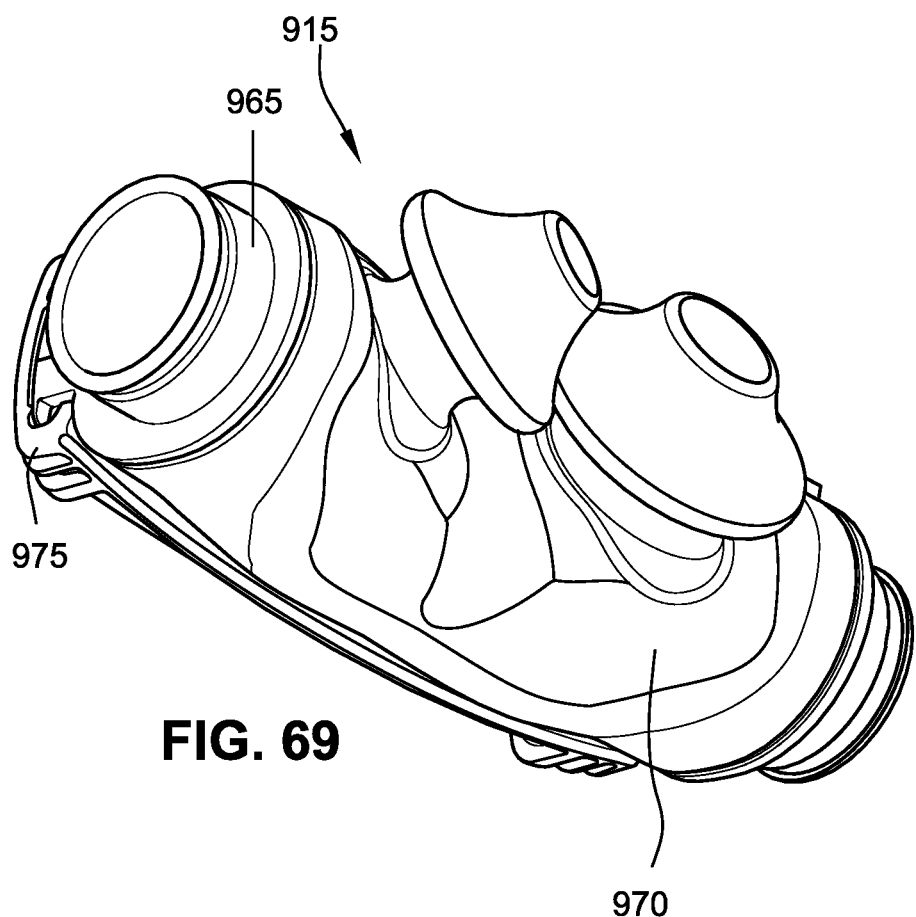
Figure 70:
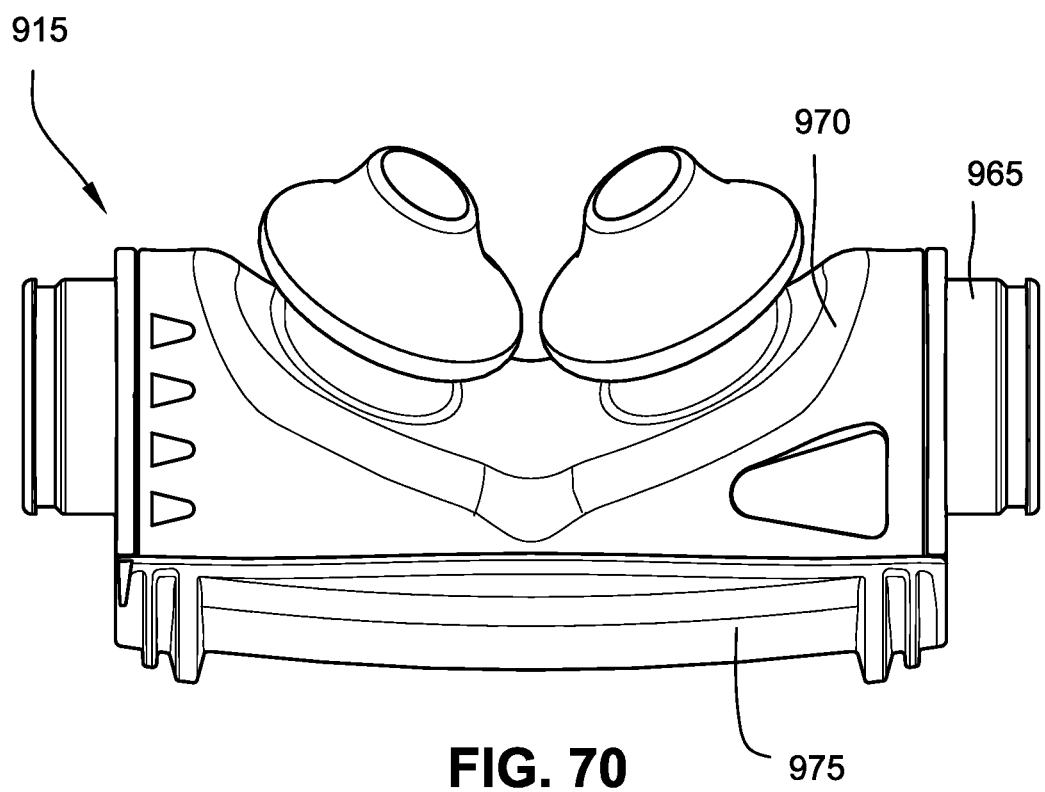
Figure 71:
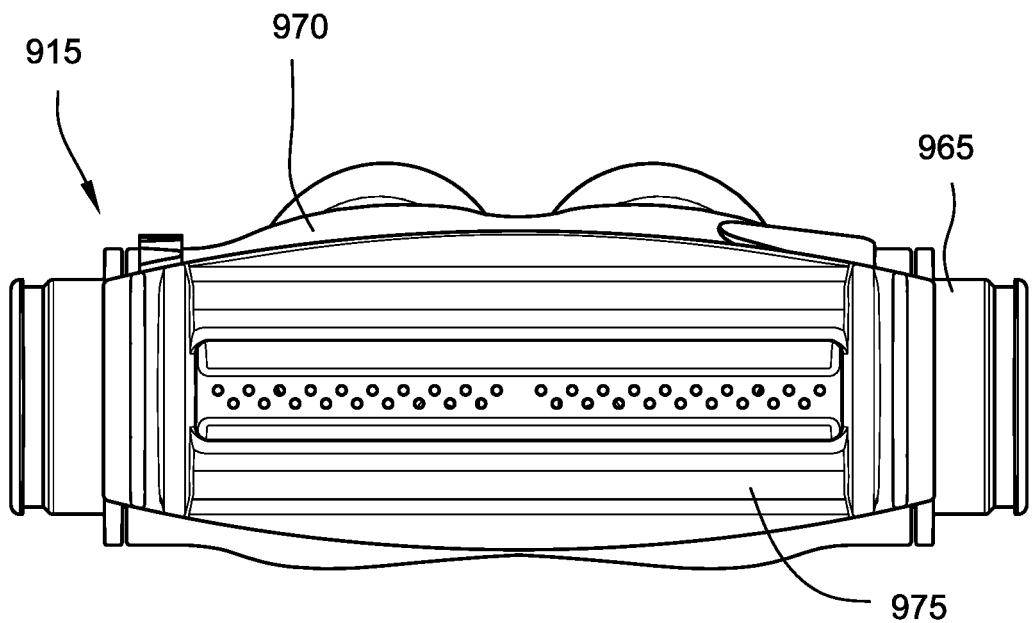
Figure 72:
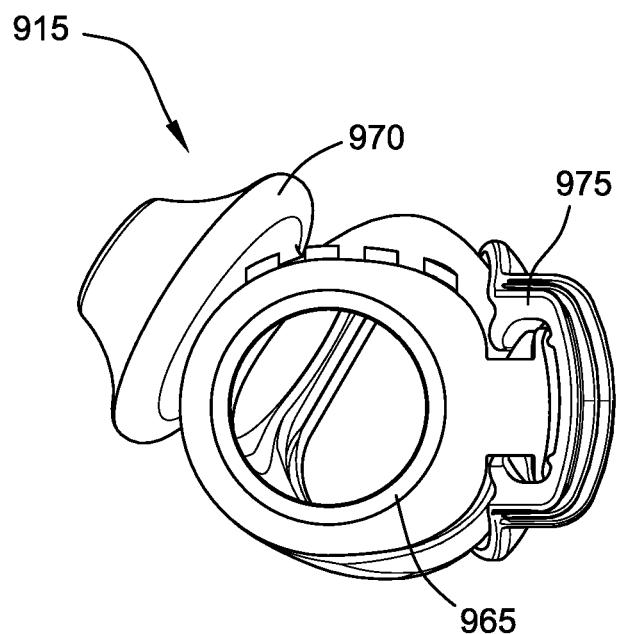
Figure 73:
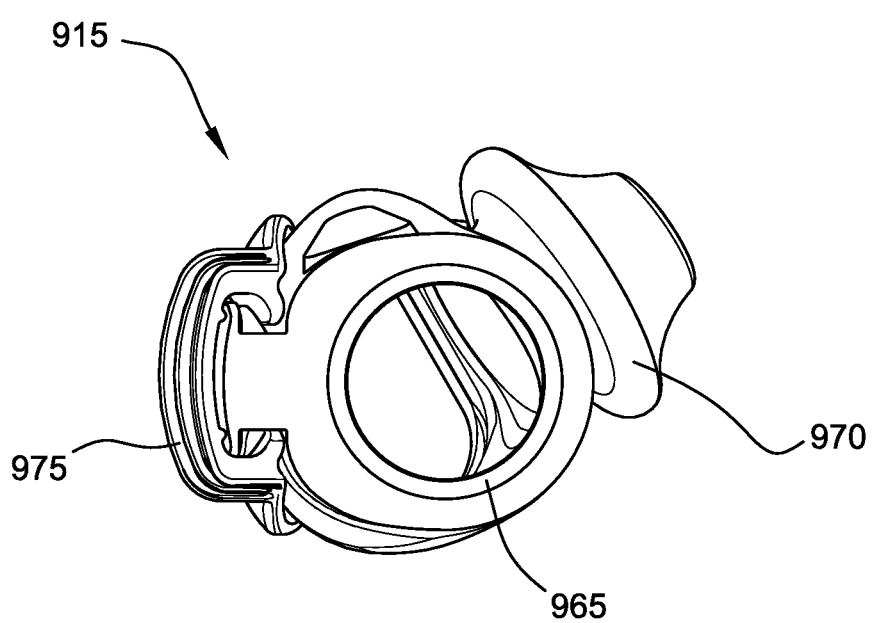
Figure 74:
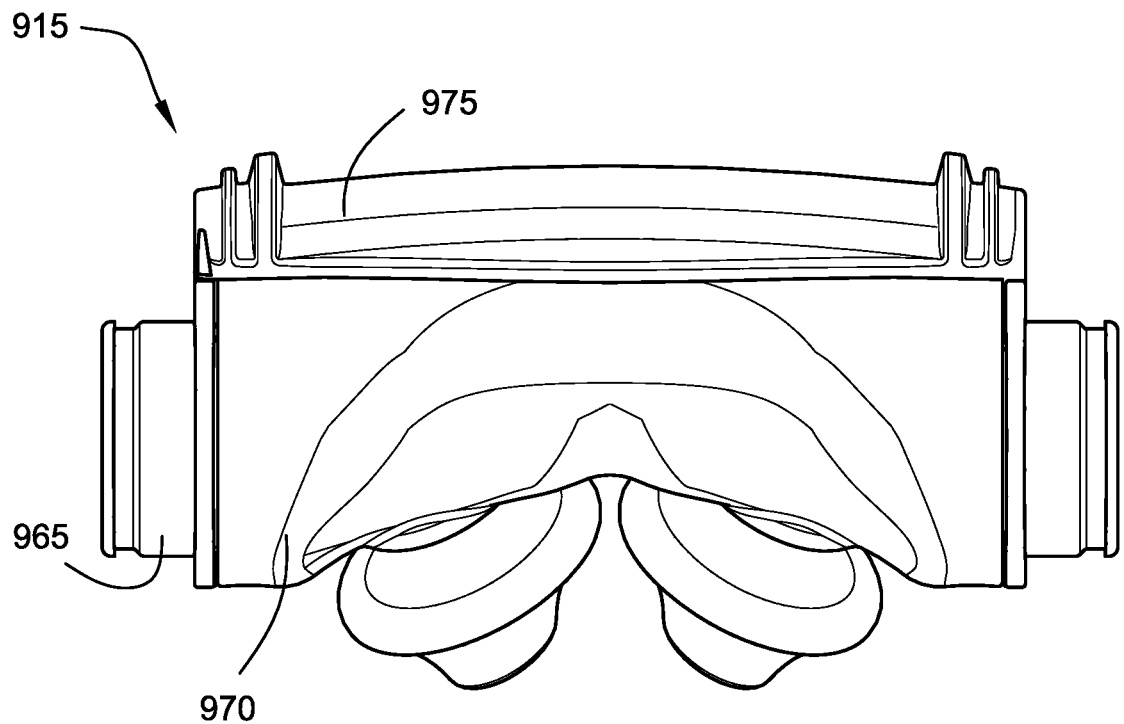
Figure 75:
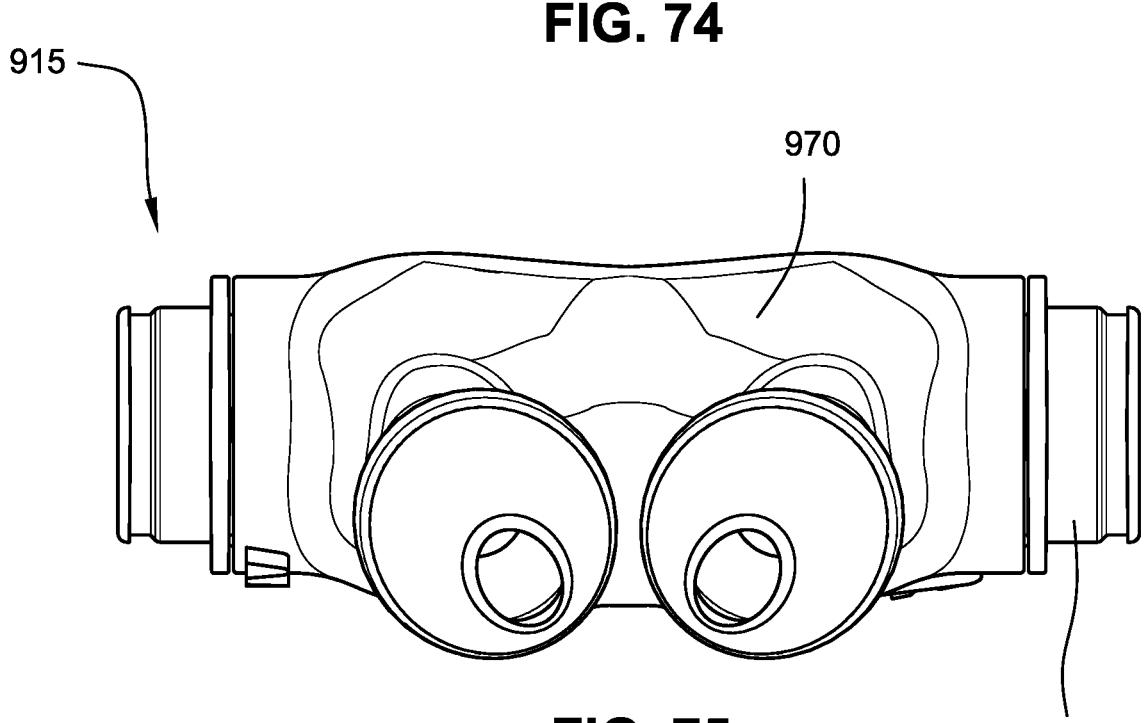
Figure 76:
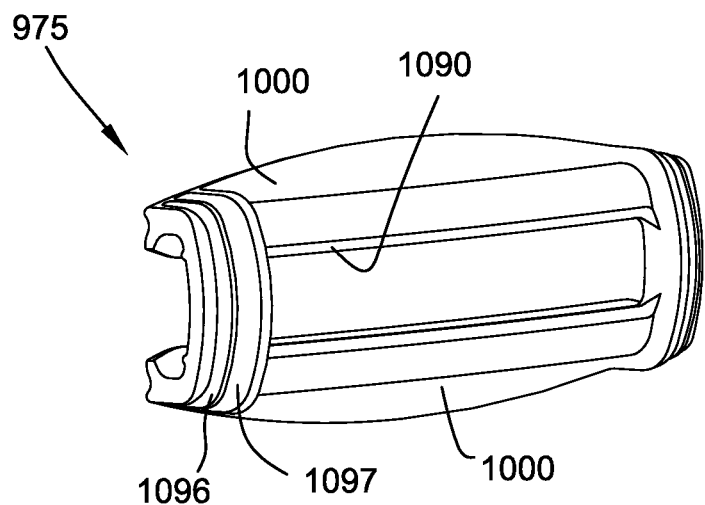
FIGS. 76-83 are various views of a clip of the nasal assembly shown in FIG. 67.
Figure 77:
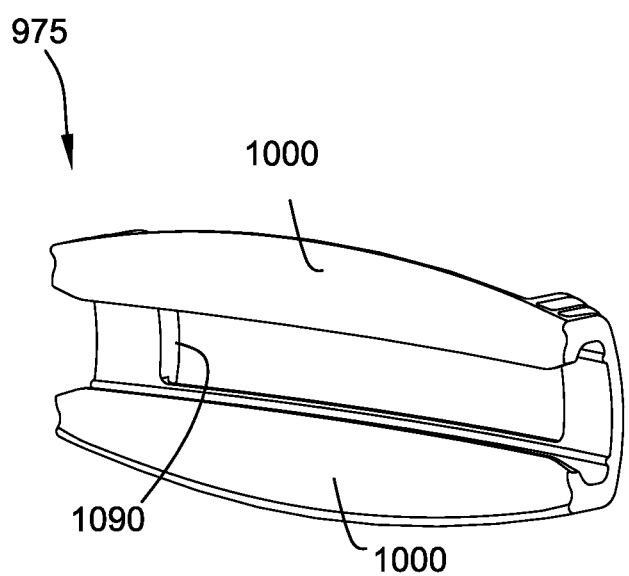
Figure 78:
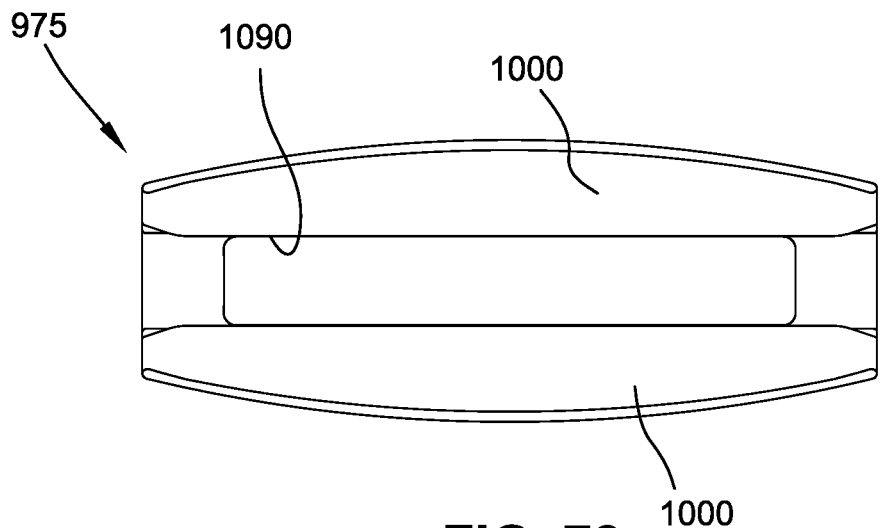
Figure 79:
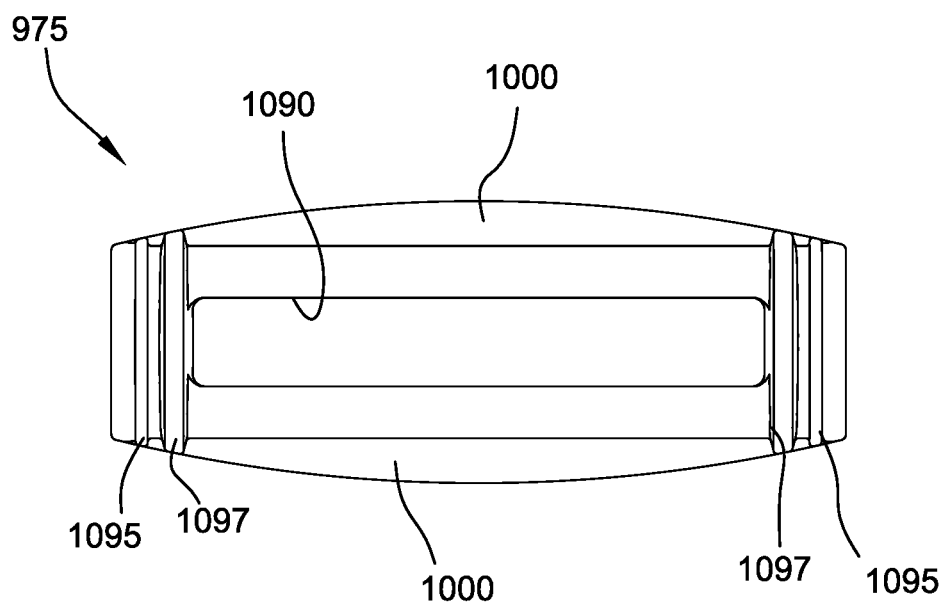
Figure 80:
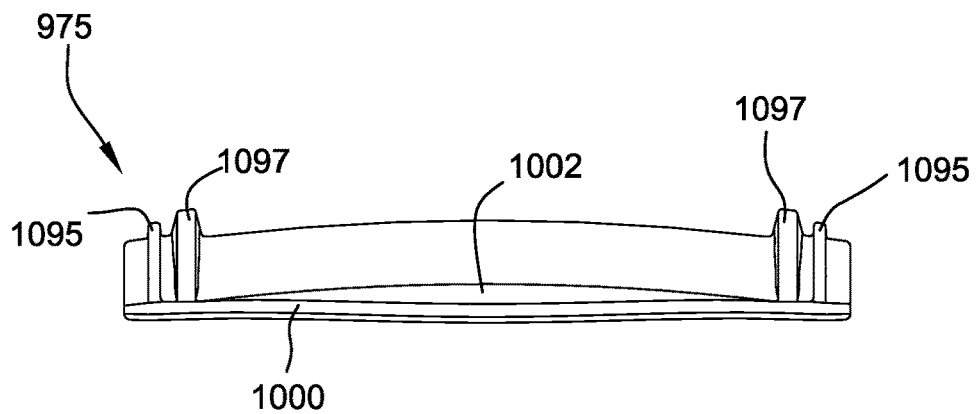
Figure 81:
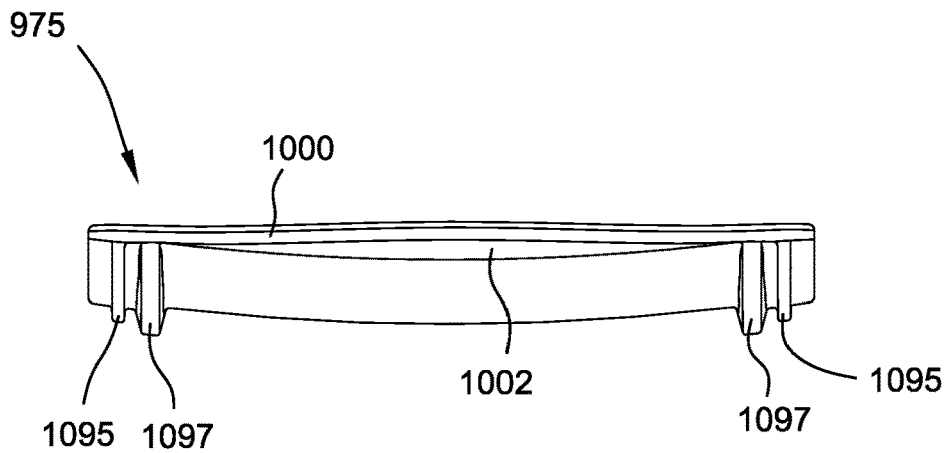
Figure 82:
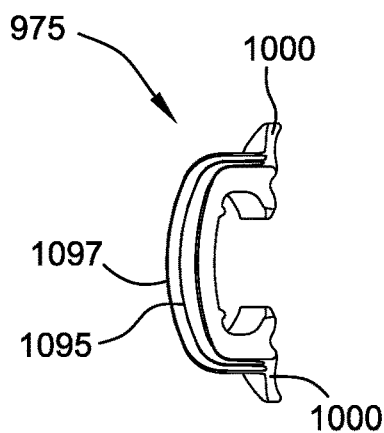
Figure 83:
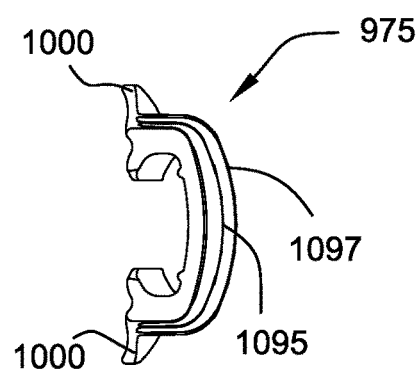

FIGS. 67-83 illustrate a nasal assembly 905 according to another embodiment of the present invention. As shown in FIG. 67, the nasal assembly 905 includes a cushion assembly 915, yokes 925 to provide stability to the sides of the headgear, seal portion 950 and elbow 935 provided to one end of the cushion assembly 915, and seal portion 950 and plug 930 provided to the other end of the cushion assembly 915. The positions of the swivel elbow 935 and the plug 930 may be interchanged, according to preference, e.g., the typical sleeping position of the patient.

The yoke 925 may include a yoke ring 955. The cushion assembly 915 may be adjustably rotated with respect to headgear, to a position which best fits the patient. The ring 955 of the yoke 925 associated with the other side of the headgear may include one or more alignment markers 961 that can be selectively aligned with one of a plurality of alignment markers 960 provided on the cushion.

5.1 Swivel Elbow

The swivel elbow 935 includes one end provided to the cushion assembly 915 and the opposite end provided to an air delivery tube. As illustrated, the end provided to the cushion assembly 915 includes two prongs 937 and a pair of key-shaped apertures 939 (only one aperture being visible) to reduce stress. Such a swivel elbow is disclosed in PCT Application No. PCT/AU2004/000207, filed Feb. 20, 2004, the entirety of which is incorporated herein by reference.

5.2 Cushion Assembly

The cushion assembly 915 includes a frame 965, a cushion 970 and a clip 975. FIGS. 68-75 show the assembly of the frame, cushion, and clip, and FIGS. 76-83 show the clip in isolation.

5.3 Frame

The frame 965 may be similar to one or more of the frames described above. Therefore, the frame 965 will not be described in further detail.

5.4 Cushion

The cushion 970 may be similar to one or more of the cushions described above. Therefore, the cushion 970 will not be described in further detail.

5.5 Clip

The clip 975 includes a main body having lateral ends, either one of which can be assembled to the cushion/frame subassembly, by sliding action to secure the same. Such a clip is disclosed in U.S. Design application No. 29/258,084, filed Apr. 14, 2006, the entirety of which is incorporated herein by reference.

5.5.1 Vent Window

The clip 975 includes a vent window 1090 that aligns with the vent holes in vent channel upon assembly of the clip to the cushion/frame subassembly.

5.5.2 Ribs

The clip 975 includes two ribs 1095, 1097 provided on each lateral side thereof. The two ribs 1095, 1097 increases stiffness to prevent disassembly of the clip 975, thus improving the retention and seal of the cushion 970 to the frame 965. In addition, the two ribs 1095, 1097 improve usability by providing grip during assembly/disassembly.

5.5.3 Wings

The clip 975 includes wings 1000 on each side of the main body. The wings 1000 extend laterally from a bottom of the clip 975 (e.g., in contrast to wings 200 that extend from a top surface of clip 75.

In addition, each wing 1000 has a reinforced section 1002 that increases stiffness in the clamping direction to prevent disassembly of the clip 975, thus improving the retention and seal of the cushion 970 to the frame 965.

6.0 Alternative Vent Arrangement

Figure 84:
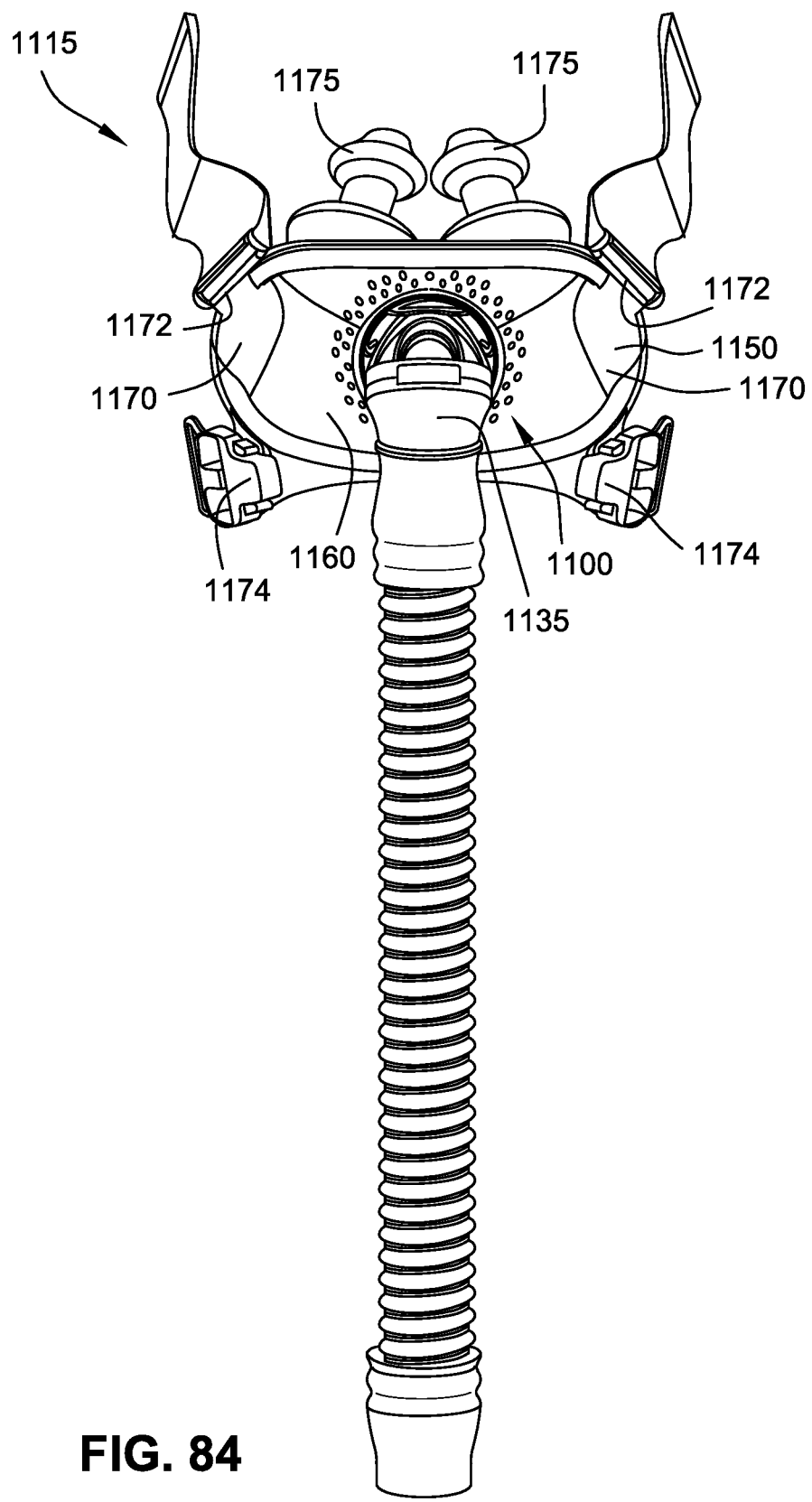
FIG. 84 illustrates a mask including a vent assembly according to another embodiment of the present invention.

FIG. 84 illustrates a nasal and mouth mask 1115 including a frame 1150 having a vent assembly 1100 according to another embodiment of the present invention. The frame 1150 is substantially similar to the frame 650 described above. As illustrated, the frame 1150 includes a main body 1160 having a side frame portion 1170 on each lateral side thereof. The main body 1160 includes an aperture 1162 (e.g., see FIG. 85) adapted to retain an elbow 1135. Also, the frame 1150 is structured to retain a mouth cushion which supports nasal prongs 1175. In addition, each side frame portion 1170 includes headgear attachment points, e.g., upper and lower anchors 1172, 1174, for attaching a headgear assembly.

In contrast to the frame 650, the frame 1150 includes a vent assembly 1100 that extends around the aperture 1162 and hence the elbow 1135 in use. As schematically shown in FIG. 85, the frame 1150 includes a relatively flattened area 1151 around the aperture 1162 (also referred to as an elbow mounting hole) adapted to retain the elbow 1135. The vent assembly 1100 is provided to the relatively flattened area 1151 and includes an array or pattern of relatively small holes 1105 arranged in concentric circles around the aperture 1162. This arrangement directs air directly away from all materials, e.g., pillows and bed linens, to reduce noise, and spreads the holes over a relatively wide area so that the bed partner will not be affected by a concentrated airstream.

In the illustrated embodiment, the holes 1105 are arranged in two concentric circles C1, C2 around the aperture 1162. However, the holes may be arranged in any number of circles around the aperture, e.g., 1-10 concentric circles. Also, each circle may include any suitable number of holes, e.g., 5-50 holes. The holes in adjacent circles may be aligned and/or offset from one another. However, the holes 1105 may be arranged in other suitable arrangements around the aperture 1162. For example, the holes 1105 may be non-concentrically arranged around the aperture 1162, e.g., randomly arranged. In addition, each hole 1105 may include a generally part conic shape as described above.

It should be appreciated that the vent assembly 1100 may be incorporated into other mask arrangements, e.g., nasal mask, full-face mask, etc.

6.1 Noise Reduction

The vent assembly 1100 described above may create noise when flow from the vent holes 1105 engages or blows into the back of the elbow 1135. To prevent this, a "keyed" elbow retaining clip may be used that is structured to mask holes when they are aligned with the elbow 1135.

FIGS. 86-88 illustrate an elbow assembly according to an embodiment of the present invention. The elbow assembly includes an elbow 1135 (FIGS. 86-87) and an elbow retaining clip 1136 (FIG. 88) to retain the elbow 1135 to the frame 1150.

The elbow 1135 includes a mating portion 1141 that is inserted into the aperture 1162 provided in the frame 1150, and the elbow retaining clip 1136 is attached to the mating portion 1141 from an inner side of the frame 1150 so as to prevent withdrawal of the mating portion 1141 and hence the elbow 1135 from the aperture 1162.

As illustrated, the mating portion 1141 includes a key or protrusion 1143 that is adapted to engage within a corresponding keyway or recess 1137 provided to the elbow retaining clip 1136. The engagement between the key 1143 and keyway 1137 ensures that the elbow retaining clip 1136 is correctly oriented with respect to the elbow 1135.

Moreover, the elbow retaining clip 1136 includes a wiper member or tab 1139 that is structured to block, cover, and/or mask one or more vent holes 1105 from the inner side of the frame 1150 which are aligned with the elbow 1135. This arrangement blocks vent flow from blowing into the back of the elbow 1135, which reduces noise in use. Because the elbow retaining clip 1136 is keyed with the elbow 1135, the wiper member 1139 will rotate along the elbow 1135 to block the affected vent holes, i.e. vent holes aligned with the elbow 1135.

This vent and elbow arrangement has several advantages. For example, the relatively small vent holes provides lower mask noise for the patient and bed partner, and the diffuse placement of the vent holes provides a lower risk of the bed partner being affected. Because there are less complaints from the bed partner, the mask provides greater compliance as the patient may be more willing to wear the mask.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike.

What is claimed is:

1. An oro-nasal mask assembly for delivering pressurized breathable air to a patient, comprising:
   a frame having a main body with a lower bore to receive the pressurized air, the frame having an upper support member and a longitudinal axis dividing the lower bore and extending along the upper support member;
   a forehead support supported by the upper support member;
   an elbow in communication with the lower bore; and
   a cushion configured to seal around the nose and mouth of the patient in use, the cushion being coupled with the main body of the frame,
   wherein the frame includes a vent arrangement positioned along the longitudinal axis between the lower bore and the upper support member, the vent arrangement comprising a three column pattern including a center column and a pair of outside columns, the center column being aligned with and fixedly located on the longitudinal axis and each of the outside columns being parallel to but offset from the longitudinal axis, wherein the center column includes 10-20 holes and each said outside column includes 8-15 holes,
   wherein the vent arrangement consists of the three column pattern.

2. The oro-nasal mask assembly according to claim 1, wherein the holes in the outside columns are aligned with the holes in the center column.

3. The oro-nasal mask assembly according to claim 1, wherein the holes in the outside columns are offset relative to the holes in the center column.

4. The oro-nasal mask assembly according to claim 1, wherein each of the holes has a part conic shape, including opposed walls that converge from a larger inside diameter to a smaller outside diameter as viewed in the direction of exhausted air.

5. The oro-nasal mask assembly according to claim 1, wherein the upper support member includes spaced apart side walls and at least an upper part of the center column and an upper part of each said outside column is positioned between the side walls of the upper support member.

6. The oro-nasal mask assembly according to claim 1, wherein the center column has more holes than each of the outside columns.

7. The oro-nasal mask assembly according to claim 1, wherein each said hole has a length of about 1.7 mm.

8. The oro-nasal mask assembly according to claim 1, wherein the frame comprises a molded plastic of polycarbonate and/or polypropylene, and the cushion comprises an elastomeric material.

9. The oro-nasal mask assembly according to claim 1, wherein said frame includes a cushion channel to receive a longitudinal edge of the cushion.

10. The oro-nasal mask assembly according to claim 1, wherein the three column pattern is provided on an oval shaped portion of the main body of the frame.

11. The oro-nasal mask assembly according to claim 1, wherein the holes in the outside columns are offset relative to the holes in the center column,
    each of the holes has a part conic shape, including opposed walls that converge from a larger inside diameter to a smaller outside diameter as viewed in the direction of exhausted air,
    at least an upper part of the center column and each said outside column is positioned between the side walls of the upper support member,
    wherein the center column has more holes than each of the outside columns,
    wherein the frame comprises a molded plastic of polycarbonate and/or polypropylene, and the cushion comprises an elastomeric material,
    wherein said frame includes a cushion channel to receive a longitudinal edge of the cushion,
    the cushion is dimensioned to surround the nose and mouth of the patient,
    the vent arrangement is positioned where interior surfaces of the frame converge, and
    wherein the three column pattern is provided on an oval shaped portion of the main body of the frame.

12. A patient interface for delivering breathable gas to a patient, comprising: aflame including a longitudinal axis configured to align with the patient's sagittal plane in use; a cushion to communicate with a patient's airways in use, the cushion being coupled with the frame; and a vent portion including a plurality of vent holes extending through a rigid material of the frame, said vent holes being provided in at least two columns each being fixed on or parallel to the longitudinal axis and each column having between 8-15 vent holes,
    wherein at least an upper part of each of the at least two columns is recessed between side walls of an upper support member supporting a forehead support.

13. The patient interface according to claim 12, wherein the vent holes are provided directly in the frame.

14. The patient interface according to claim 12, wherein said holes converge towards the outlet side.

15. The patient interface according to claim 12, wherein said cushion is a nasal only cushion.

16. The patient interface according to claim 12, wherein said cushion is a nasal-oro cushion configured to surround the patient's nose and mouth.

17. The patient interface according to claim 12, wherein each of the holes has a part conic shape, including opposed walls that converge from a larger inside diameter to a smaller outside diameter as viewed in the direction of exhausted air.

18. The patient interface according to claim 12, wherein each said hole has a length of about 1.7 mm.

19. The patient interface according to claim 12, wherein the vent holes are arranged in a pattern consisting of three columns.

20. The patient interface according to claim 19, wherein the three columns are provided on an oval shaped portion of the main body of the frame.

21. The patient interface according to claim 12, wherein the frame comprises a molded plastic of polycarbonate and/or polypropylene, and the cushion comprises an elastomeric material.

22. The patient interface according to claim 12, wherein said frame includes a cushion channel to receive a longitudinal edge of the cushion.

23. The patient interface according to claim 12, wherein the vent holes are provided in three columns with a center column and a pair of outside columns, the holes in the outside columns are offset relative to the holes in the center column.

24. The patient interface according to claim 23, wherein at least an upper part of the center column and an upper part of each said outside column are recessed between side walls of an upper support member supporting a forehead support.

25. The patient interface according to claim 23, wherein the center column has more holes than each of the outside columns.

26. The patient interface according to claim 12,
wherein the frame includes a forehead support,
wherein the vent holes are provided directly in the frame,
wherein said holes converge towards the outlet side,
wherein said cushion is a nasal-oro mask,
wherein each of the holes has a part conic shape, including opposed walls that converge from a larger inside diameter to a smaller outside diameter as viewed in the direction of exhausted air,
wherein the frame comprises a molded plastic of polycarbonate and/or polypropylene, and the cushion comprises an elastomeric material,
wherein said frame includes a cushion channel to receive a longitudinal edge of the cushion,
wherein the vent holes are provided in three columns with a center column and a pair of outside columns,
wherein the center column has more holes than each of the outside columns, and
wherein the three columns are provided on an oval shaped portion of the main body of the frame.

27. A mask assembly for delivering breathable gas to a patient for treatment of sleep disordered breathing, comprising:
a frame having a longitudinal axis configured to be aligned with the patient's sagittal plane in use; and
a cushion adapted to form a seal with a patient's airways, the cushion being coupled with the frame and forming a breathing chamber,
wherein the frame includes a base wall with a plurality of vent holes arranged in a plurality of columns structured to allow washout of exhaled gases from the breathing chamber,
the plurality of columns including a center column fixedly located on the longitudinal axis and an adjacent flanking column flanking each side of the center column, each said column having at least 5 holes and the total number of holes for all the columns is at least 35 holes+/−10-20%, and
each said flanking column including holes being laterally aligned with or offset from holes in the center column, wherein the holes in the flanking columns are laterally aligned with one another,
wherein the holes converge towards an outlet side.

28. A mask assembly according to claim 27,
wherein there are only three columns,
wherein each column includes at least 8+/−10-20% vent holes,
wherein the center column includes more holes than each of the flanking columns, and
wherein said cushion is a pillows cushion, a nasal only cushion or a nasal-oro cushion.

29. System for treating sleep disordered breathing, comprising:
a mask assembly according to claim 27;
a blower to supply breathable gas at positive pressure; and
a conduit to pass the breathable gas from the blower to the mask assembly.

* * * * *

UNITED STATES PATENT AND TRADEMARK OFFICE
CERTIFICATE OF CORRECTION

| | |
|---|---|
| PATENT NO. | : 11,478,597 B2 |
| APPLICATION NO. | : 17/537557 |
| DATED | : October 25, 2022 |
| INVENTOR(S) | : Judson et al. |

It is certified that error appears in the above-identified patent and that said Letters Patent is hereby corrected as shown below:

In the Claims

Claim 12, Column 16, Line 56, delete "aflame" and insert --a frame--.

Claim 27, Column 18, Line 29, delete "holes+/-10-20%, and" and insert --holes +/- 10 20%, and--.

Claim 28, Column 18, Line 37, delete "8+/-10-20%" and insert --8 +/- 10-20%--.

Signed and Sealed this
Seventh Day of March, 2023

Katherine Kelly Vidal
*Director of the United States Patent and Trademark Office*